(12) United States Patent
Piatesi et al.

(10) Patent No.: US 9,080,191 B2
(45) Date of Patent: Jul. 14, 2015

(54) METHOD FOR BIOCATALYTIC PRODUCTION OF NITRILES FROM OXIMES AND OXIME DEHYDRATASES USABLE THEREIN

(71) Applicant: BASF SE, Ludwigshafen (DE)

(72) Inventors: Andrea Piatesi, Mannheim (DE); Wolfgang Siegel, Limburgerhof (DE); Kai-Uwe Baldenius, Heidelberg (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/798,365

(22) Filed: Mar. 13, 2013

(65) Prior Publication Data

US 2013/0244298 A1   Sep. 19, 2013

Related U.S. Application Data

(60) Provisional application No. 61/609,999, filed on Mar. 13, 2012.

(51) Int. Cl.
*C12P 13/00* (2006.01)
*C12N 9/88* (2006.01)

(52) U.S. Cl.
CPC .............. *C12P 13/002* (2013.01); *C12N 9/88* (2013.01); *C12Y 499/01007* (2013.01)

(58) Field of Classification Search
None
See application file for complete search history.

(56) References Cited

U.S. PATENT DOCUMENTS

| 5,294,602 | A | 3/1994 | Brunke et al. |
| 6,596,520 | B1 | 7/2003 | Friedrich et al. |
| 7,057,030 | B2 * | 6/2006 | Bramucci et al. ............ 536/23.7 |
| 2008/0177100 | A1 | 7/2008 | Eberhardt et al. |
| 2012/0135477 | A1 | 5/2012 | Breuer et al. |

FOREIGN PATENT DOCUMENTS

| DE | 3139358 A1 | 4/1983 |
| EP | 0491127 A1 | 6/1992 |
| EP | 1 069 183 A2 | 1/2001 |
| EP | 1149849 A1 | 10/2001 |
| WO | WO-2006106141 A1 | 10/2006 |
| WO | WO-2010139719 A2 | 12/2010 |

OTHER PUBLICATIONS

Xie et al. Biosci. Biotechnol. Biochem. (2001) 65(12) 2666-2672.*
Nishihara et al. Appl. Envornm. Microbiol. (1998) 64(5) 1694-1699.*
Keto et al. (2000) Biochemistry 39, 800-809.*

* cited by examiner

*Primary Examiner* — Nashaat Nashed
(74) *Attorney, Agent, or Firm* — Drinker Biddle & Reath LLP

(57) ABSTRACT

The present invention relates to novel methods for biocatalytic production of nitriles from oximes using oxime dehydratases and novel mutants with oxime dehydratase activity and use thereof in a process for biocatalytic production of nitriles, such as in particular for the production of citral nitrile, neral nitrile, geranial nitrile or citronellyl nitrile from citral oxime, neral oxime, geranial oxime or citronellal oxime; and oxime dehydratases usable therefor, nucleotide sequences therefor and expression constructs or microorganisms comprising these.

17 Claims, 2 Drawing Sheets

METHOD FOR BIOCATALYTIC PRODUCTION OF NITRILES FROM OXIMES AND OXIME DEHYDRATASES USABLE THEREIN

RELATED APPLICATIONS

This application claims the benefit of U.S. Provisional Application 61/609,999, filed Mar. 13, 2012, which is incorporated herein by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13111_00247_US. The size of the text file is 79 KB and the text file was created on Mar. 12, 2013.

The present invention relates to novel methods for biocatalytic production of nitriles from oximes using oxime dehydratases and novel mutants with oxime dehydratase activity and use thereof in a process for biocatalytic production of nitriles, such as in particular for the production of citral nitrile, neral nitrile, geranial nitrile or citronellyl nitrile from citral oxime, neral oxime, geranial oxime or citronellal oxime; and oxime dehydratases usable therefor, nucleotide sequences therefor and expression constructs or microorganisms comprising them.

BACKGROUND OF THE INVENTION

Terpenes are organic compounds that are derived from the isoprene skeleton and occur in nature in particular as secondary substances present in organisms, in particular as secondary substances in plants. Terpenes are often odoriferous or flavoring substances, and can for example be obtained from plant-derived essential oils. Accordingly, terpenes and terpene derivatives are used as ingredients for products in the area of cosmetics, body care or for cleaning products, for instance as admixtures of odoriferous substances or aromas in perfumes, body lotions, shower gels, soaps, detergents or cleaning agents. Depending on the compound used, a variety of odor notes can be produced, for instance spicy, fresh, citrus-like or flowery fragrances of the corresponding products.

The corresponding starting products, which are offered by the chemical industry for admixture to the corresponding products, are often nitriles of terpenes or terpene derivatives. Examples are geranyl nitrile, which has an intense fresh, citrus-like odor, or citronellyl nitrile, which has a rose-like fragrance.

The corresponding nitriles are either isolated as natural products or are synthesized chemically from suitable precursors. Thus, the applicant's WO 2006/106141 describes the production of saturated nitriles from unsaturated nitriles as precursors. EP 0 491 127 describes the addition of unsaturated nitriles onto hexenols, obtaining modified nitriles. In both cases starting compounds are used that already comprise the nitrile group. Accordingly, methods are desirable by which precursors other than nitriles can also be used. DE 3139358 describes a process of production of odorants by chemical reaction of oximes to corresponding nitriles. In the context of this process, the necessary dehydration requires extreme reaction conditions, in particular caustic dehydrating agents and boiling temperatures.

There is therefore a demand for alternative methods for production of nitriles from oximes, in particular methods that take place under milder reaction conditions. Furthermore, there is a demand for suitable reagents for carrying out such a process.

SUMMARY OF THE INVENTION

The first problem mentioned above is solved by a biocatalytic process for producing nitriles of general formula I,

(I)

in which
R stands for a linear or singly or multiply branched, saturated or singly or multiply unsaturated, optionally singly or multiply substituted aliphatic hydrocarbon residue with 4 to 19 carbon atoms; and
n stands for 1 or 2;
wherein
a) an oxime of general formula II

(II)

in which R and n have the meanings given above, wherein the compound of formula II is in stereoisomerically pure form or as a mixture of stereoisomers,
is reacted in the presence of an aliphatic aldoxime dehydratase (4.99.1.5), a phenylacetaldoxime dehydratase (PAOx) (EC 4.99.1.7) or an indoleacetaldoxime dehydratase (4.99.1.6) to a compound of formula I, wherein the compound of formula I is in stereoisomerically pure form or as a mixture of stereoisomers, and
b) optionally the reaction product is then purified further.

The second problem mentioned above was solved by providing nucleic acid sequences defined herein, which code for proteins that can be used in the context of the process according to the invention.

DETAILED DESCRIPTION OF THE INVENTION

A. General Definitions

Figure 1:
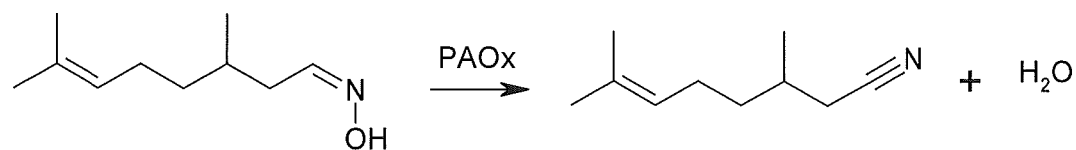
FIG. 1 shows schematically the conversion of citronellal oxime to citronellyl nitrile.

"Aldoxime dehydratases" in the sense of the present invention are generally enzymes or enzyme mutants that catalyze the elimination of water from oximes of general formula $R^1R^2C=N-OH$, wherein $R^1$ stands for any organic residue and $R^2$ stands for hydrogen. The term aldoxime dehydratases comprises other, more precisely specified aldoxime dehydratases, such as aliphatic aldoxime dehydratase (EC 4.99.1.5, according to the EC Nomenclature of the "Nomenclature Committee of the International Union of Biochemistry and Molecular Biology"), phenylacetaldoxime dehydratase (PAOx) (EC 4.99.1.7) or indoleacetaldoxime dehydratase (EC 4.99.1.6).

Owing to the reversibility of enzymatic reactions, the present invention relates to the enzymatic reactions described herein in both reaction directions.

"Functional mutants" of an aldoxime dehydratase comprise the "functional equivalents" of said enzymes defined hereunder.

The term "biocatalytic process" relates to any process carried out in the presence of catalytic activity of an "aldoxime dehydratase" according to the invention or of an enzyme with "aldoxime dehydratase activity", i.e. processes in the presence of raw, or purified, dissolved, dispersed or immobilized enzyme, or in the presence of whole microbial cells, which have or express said enzyme activity. Biocatalytic processes therefore comprise enzymatic as well as microbial processes.

The term "stereoisomerically pure" means that one of several possible stereoisomers of a compound mentioned in the context of the invention with at least one asymmetry center is present at high "enantiomeric excess" or high "enantiomeric purity", e.g. at least 90% ee, in particular at least 95% ee, or at least 98% ee, or at least 99% ee. The ee % value is calculated from the following formula:

$$ee \% = [X_A - X_B]/[X_A + X_B] * 100,$$

in which $X_A$ and $X_B$ stand for the mole fraction of the enantiomers A and B respectively.

An "aldoxime dehydratase activity", which was determined with a "reference substrate under standard conditions", means for example an enzyme activity that describes the formation of a nitrile product from an oxime substrate. Standard conditions are e.g. substrate concentrations from 10 mM to 0.2 M, in particular 15 to 100 mM, e.g. about 20 to 25 mM; at pH 4 to 8, and at temperatures of e.g. 15 to 30 or 20 to 25° C. The determination can be performed with recombinant aldoxime dehydratase-expressing cells, lysed aldoxime dehydratase-expressing cells, fractions thereof or enriched or purified aldoxime dehydratase enzyme. In particular, the reference substrate is an oxime of formula (II); in particular citronellal oxime, or a citronellal oxime racemate, as is also described in more detail in the examples. A specific standard assay for detecting aldoxime dehydratase activity is described for example by Kato, Y. et al. in Biochemistry 2000, 39, 800-809. According to this, a standard preparation contains 50 µmol potassium phosphate buffer, pH 7.0, 125 nmol FMN, 2.5 µmol enzyme. The reaction is stopped after 10 min by adding 500 µL of 0.5 M $H_3PO_4$, and the supernatant obtained by centrifugation (18 000 g, 10 min) is then analyzed for the product formed.

"Terpenes" are hydrocarbons that are made up of isoprene units ($C_5$ units), in particular noncyclic terpenes, e.g. squalene, with number of carbons divisible by 5.

"Terpenoids" are substances that are derived from terpenes, in particular noncyclic terpenes, e.g. by additional insertion of carbon atoms and/or heteroatoms, for example citronellal.

"Terpenelike" compounds in the sense of the present invention comprise in particular such compounds that come under general structural formula (IV), as defined hereunder.

In general, according to the invention all isomeric forms of the compounds described herein are included, such as constitutional isomers and in particular stereoisomers and mixtures thereof, e.g. optical isomers or geometric isomers, such as E and Z isomers, and combinations thereof. If several asymmetry centers are present in a molecule, the invention comprises all combinations of different conformations of these asymmetry centers, e.g. enantiomeric pairs.

Unless stated otherwise, the following general chemical definitions apply herein:

Aliphatic hydrocarbon residues comprise residues that are derived from acyclic or cyclic, saturated or unsaturated carbon compounds with the exception of aromatic compounds. Aliphatic hydrocarbon residues comprise in particular linear or branched alkyl residues and linear or branched alkenyl residues. Nonlimiting examples are listed below:

Alkyl and all alkyl moieties in residues derived therefrom, e.g. hydroxyalkyl: saturated, linear or singly or multiply, e.g. 1-, 2-, 3- or 4-fold branched hydrocarbon residues with 1 to 4, 1 to 6, 1 to 8, 1 to 10 or 4 to 10 carbon atoms, e.g.

$C_1$-$C_{10}$-alkyl or $C_1$-$C_6$-alkyl or $C_4$-$C_{10}$-alkyl: such as methyl, ethyl, propyl, 1-methylethyl, butyl, 1-methylpropyl, 2-methylpropyl, and 1,1-dimethylethyl as typical representatives of $C_1$-$C_4$-alkyl; and pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, such as in particular the meanings of R given in Table 4, e.g. hexyl Hydroxy-$C_1$-$C_{10}$-alkyl, e.g. hydroxy-$C_1$-$C_6$-alkyl, or hydroxy-$C_1$-$C_4$-alkyl, or hydroxy-$C_4$-$C_{10}$-alkyl: e.g. hydroxymethyl, 1- or 2-hydroxyethyl, 1-, 2- or 3-hydroxypropyl, 1-hydroxymethylethyl, 1-, 2-, 3- or 4-hydroxybutyl, 1-hydroxymethylpropyl and 2-hydroxymethylpropyl; or other hydroxy-substituted analogs of the above alkyl residues, such as in particular the meanings of R given in Table 4, e.g. 6-hydroxy-6-methylhept-1-yl.

Alkenyl stands for singly or multiply, in particular singly or doubly unsaturated, linear or singly or multiply, e.g. 1-, 2-, 3- or 4-fold branched hydrocarbon residues with 2 to 4, 2 to 6, 2 to 8, 2 to 10, 4 to 10, 2 to 20 or 4 to 20 carbon atoms and a double bond in any position, or 2 non-cumulative, conjugated or in particular non-conjugated double bonds, e.g. $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, such as in particular the meanings of R given in Table 4, such as 2,6-dimethylhepta-1,5-dien-1-yl, 2,6-dimethylhept-5-en-1-yl, 2,6-dimethylocta-1,5-dien-1-yl, octa-1,5-dien-1-yl, 1,5-dimethylhexa-4-en-1-yl, 1,5,9-trimethylnon-8-en-1-yl.

"Oxo" stands e.g. for a residue that forms, together with the carbon atom to which it is bound, a keto group (C=O). Accordingly, for example derived residues of the aforementioned hydrocarbon residues are those bearing one or more keto groups.

"Methylene" (=CH$_2$) stands e.g. for a residue that forms, together with the carbon atom to which it is bound, a vinyl residue (—CH=CH$_2$).

B. Special Embodiments of the Invention

The present invention relates in particular to the following special embodiments:

1. Biocatalytic Process for Producing Nitriles of General Formula I

R─[─C≡N]$_n$  (I)

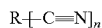

in which
    R stands for a linear or singly or multiply branched, saturated or singly or multiply unsaturated, optionally singly or multiply substituted aliphatic hydrocarbon residue with 4 to 19 carbon atoms, such as in particular linear or branched $C_1$-$C_{10}$-alkyl, or linear or branched hydroxy-$C_1$-$C_{10}$-alkyl, or linear or branched $C_2$-$C_{10}$-alkenyl, or linear or branched, doubly unsaturated $C_4$-$C_{10}$-alkenyl; and
    n stands for 1 or 2, in particular 1;
    wherein an oxime of general formula II R─[─CH=N—OH]$_n$  (II)

in which R and n have the meanings given above, wherein the compound of formula II is in stereoisomerically pure form or as a mixture of stereoisomers,
    is reacted in the presence of an aliphatic aldoxime dehydratase (4.99.1.5), a phenylacetaldoxime dehydratase (PAOx) (EC 4.99.1.7) or an indoleacetaldoxime dehydratase (4.99.1.6), for example an enzyme comprising an amino acid sequence selected from SEQ ID NO: 1 and 4 to 28, or has an amino acid sequence identical to one of these sequences to at least 60%, e.g. at least 65, 70, 75, 80, 85, 90, 91, 92, 93, 94, 95, 96, 97, 98, or 99%; in particular a phenylacetaldoxime dehydratase (PAOx) (EC 4.99.1.7), in particular an enzyme comprising SEQ ID NO:1 or has an amino acid sequence identical to this to at least 60%, e.g. at least 65, 70, 75, 80, 85, 90, 91, 92, 93, 94, 95, 96, 97, 98, or 99%; to a compound of formula I, wherein the compound of formula I is in stereoisomerically pure form or as a mixture of stereoisomers, and
    b) optionally the reaction product is then purified further.

2. Process according to embodiment 1, wherein the PAOx is an enzyme from *Rhodococcus* sp., *Gibberella zeae* or in particular *Bacillus* sp.

3. Process according to one of the aforementioned embodiments, wherein the PAOx has an amino acid sequence according to SEQ ID NO: 1 or an amino acid sequence identical to this to at least 60%, e.g. at least 65, 70, 75, 80, 85, 90, 91, 92, 93, 94, 95, 96, 97, 98, or 99%; or wherein up to 25%, e.g. up to 20, 15, 10, 9, 8, 7, 6, 5, 4, 3, 2 or 1% of the amino acid residues are altered relative to SEQ ID NO:1 by addition, deletion, insertion, substitution, inversion or a combination thereof, and which still has at least 50%, e.g. at least 60, 65, 70, 75, 80, 85, 90 or 95% of the enzymatic activity of SEQ ID NO:1.

4. Process according to one of the aforementioned embodiments, wherein an oxime of formula II is reacted, in which the residue R, together with the carbon atom to which it is bound, is derived from a noncyclic terpene residue, selected from hemiterpene ($C_5$), monoterpene ($C_{10}$), sesquiterpene ($C_{15}$), diterpene ($C_{20}$), sesterterpene ($C_{25}$), triterpene ($C_{30}$) or tetraterpene ($C_{40}$) residues (in particular by partial or complete hydrogenation), or from corresponding terpene residues that are shortened by 1 to 3 carbon atoms.

5. Process according to one of the aforementioned embodiments, wherein an oxime of formula II is reacted, in which n stands for 1 and residue R has one of the meanings given above.

6. Process according to one of the aforementioned embodiments, wherein a compound of formula II, selected from citral oxime, neral oxime, geranial oxime, citronellal oxime and partially or fully hydrogenated analogs thereof, such as 6,7-dihydrocitronellyl oxime, is converted to the corresponding nitrile.

7. Process according to embodiment 6, wherein citronellal oxime of formula IIa

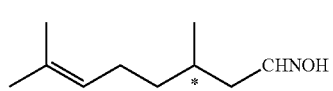
(IIa)

is converted to citronellyl nitrile of formula Ia

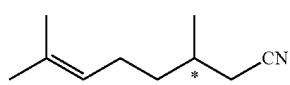
(Ia)

wherein the compound of formula IIa is used in stereoisomerically pure form or as stereoisomeric mixture, such as in particular as R/S and/or E/Z mixture, in particular an R/S and E/Z mixture.

8. Process according to one of the aforementioned embodiments, wherein the reaction takes place enzymatically, in the presence of PAOx, a PAOx-containing protein mixture, or in the presence of a recombinant microorganism functionally expressing PAOx, a PAOx-containing cell homogenate derived therefrom or a PAOx-containing fraction thereof.

9. Process according to one of the aforementioned embodiments, wherein PAOx or the microorganism functionally expressing PAOx is present in the reaction mixture in free or in immobilized form.

10. Process according to one of the embodiments 8 and 9, wherein the recombinant microorganism is a bacterial strain functionally expressing PAOx, in particular a strain of *E. coli*.

11. Process according to embodiment 10, wherein the recombinant microorganism carries an expression construct, which has the nucleotide sequence coding for PAOx, optionally adapted to the codon usage of the microorganism.

12. Process according to one of the embodiments 8 to 11, wherein the microorganism additionally expresses at least one chaperone supporting the functional expression (in particular correct folding) of PAOx.

13. Process according to embodiment 12, wherein the recombinant microorganism is a bacterial strain, which in addition to PAOx expresses one or more chaperones selected from GroEL and GroES.

14. Process according to one of the preceding embodiments, wherein the reaction is carried out in, in particular pure substrate, i.e. without further addition of usual additives, such as water, or buffer, as reaction medium, wherein in particular whole cells expressing the dehydratase enzyme are used.
15. Nucleotide sequence according to SEQ ID NO: 2 or 3, coding for PAOx, wherein the nucleotide sequence is adapted to the codon usage of the microorganism *Escherichia coli*.
16. Expression construct according to the definition in one of the embodiments 11 to 14 or comprising a nucleotide sequence according to embodiment 15.
17. Recombinant microorganism according to the definition in one of the aforementioned embodiments 8 to 14, or comprising a nucleotide sequence according to embodiment 15 or an expression construct according to embodiment 16.

C. Further Embodiments of the Invention

1. Proteins/Enzyme Mutants According to the Invention

The present invention is not limited to the enzymes with aldoxime dehydratase activity concretely disclosed herein, but rather also extends to functional equivalents thereof.

"Functional equivalents" or analogs of the concretely disclosed enzymes and enzyme mutants are, in the context of the present invention, various polypeptides thereof, which moreover possess the desired biological activity, e.g. aldoxime dehydratase activity.

Thus, for example "functional equivalents" means enzymes and mutants that have, in an assay for "aldoxime dehydratase activity" used in the sense of the invention (i.e. with a reference substrate under standard conditions), an activity of an enzyme, comprising an amino acid sequence defined concretely herein (e.g. a mutant derived from SEQ ID NO:1 or derived from one of the sequences according to SEQ ID NO: 4 to 28), that is higher or lower by at least 1%, in particular by at least about 5 to 10%, e.g. at least 10% or at least 20%, e.g. at least 50% or 75% or 90%.

The data on activity for functional equivalents refer herein, unless stated otherwise, to activity determinations performed by means of a reference substrate under standard conditions, as defined herein.

The "aldoxime dehydratase activity" in the sense of the invention can be detected by means of various known assays. Without being restricted to this, we may mention an assay using a reference substrate, e.g. citronellal oxime or citronellal oxime racemate, under standard conditions, as described above (cf. Kato et al., Biochemistry, 2000, 39, 800-809; described for PAOx; and similarly applicable or adaptable to other aldoxime dehydratases) and explained in the experimental section.

Functional equivalents are moreover for example stable between pH 4 to 11 and advantageously possess a pH optimum in the range from pH 5 to 10, such as in particular 6.5 to 9.5 or 7 to 8 or at about 7.5, and a temperature optimum in the range from 15° C. to 80° C. or 20° C. to 70° C., e.g. about 30 to 60° C. or about 35 to 45° C., such as at 40° C.

"Functional equivalents" comprise the mutants obtainable by one or more, e.g. 1 to 50, 2 to 30, 2 to 15, 4 to 12 or 5 to 10 "additional mutations", such as amino acid additions, substitutions, deletions and/or inversions, wherein the stated changes can occur in any sequence position, provided they lead to a mutant with the property profile according to the invention. Functional equivalence in particular also obtains when the patterns of reactivity between mutant and unaltered polypeptide coincide qualitatively, i.e. for example identical substrates are converted at a different rate.

"Additional mutations" of this kind can occur at any position whatsoever of the respective amino acid sequence.

Nonlimiting examples of suitable amino acid substitutions are presented in the following table:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described as well as "functional derivatives" and "salts" of the polypeptides.

"Precursors" are natural or synthetic precursors of the polypeptides with or without the desired biological activity.

The expression "salts" means both salts of carboxyl groups and salts of acid addition of amino groups of the protein molecules according to the invention. Salts of carboxyl groups can be produced in a manner known per se and comprise inorganic salts, for example sodium, calcium, ammonium, iron and zinc salts, and salts with organic bases, for example amines, such as triethanolamine, arginine, lysine, piperidine and the like. Salts of acid addition, for example salts with mineral acids, such as hydrochloric acid or sulfuric acid and salts with organic acids, such as acetic acid and oxalic acid are also covered by the invention.

"Functional derivatives" of polypeptides according to the invention can also be produced on functional amino acid side groups or at their N- or C-terminal end by known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxyl groups, produced by reaction with acyl groups.

"Functional equivalents" naturally also comprise polypeptides that are accessible from other organisms, and naturally occurring variants. For example, ranges of homologous sequence regions can be established by sequence comparison and equivalent enzymes can be determined on the basis of the concrete specifications of the invention.

"Functional equivalents" also comprise fragments, preferably individual domains or sequence motifs, of the polypeptides according to the invention, which for example have the desired biological function.

"Functional equivalents" are moreover fusion proteins, which have one of the aforementioned polypeptide sequences or functional equivalents derived therefrom and at least one further heterologous sequence, functionally different therefrom, in functional N- or C-terminal linkage (i.e. without mutual substantial functional impairment of the fusion protein moieties). Nonlimiting examples of heterologous sequences of this kind are e.g. signal peptides, histidine anchors or enzymes.

"Functional equivalents" included according to the invention are homologs of the concretely disclosed proteins. These possess at least 60%, preferably at least 75%, in particular at least 85%, e.g. 90, 91, 92, 93, 94, 95, 96, 97, 98 or 99%, homology (or identity) with one of the concretely disclosed amino acid sequences, calculated using the algorithm of Pearson and Lipman, Proc. Natl. Acad. Sci. (USA) 85(8), 1988, 2444-2448. A percentage homology or identity of a homologous polypeptide according to the invention means in particular percentage identity of the amino acid residues relative to the total length of one of the amino acid sequences concretely described herein.

The percentage identity values can also be determined on the basis of BLAST alignments, the blastp algorithm (protein-protein BLAST), or using the Clustal settings given below.

In the case of a possible protein glycosylation, "functional equivalents" according to the invention comprise proteins of the type stated above in deglycosylated or glycosylated form and modified forms obtainable by altering the glycosylation pattern.

Homologs of the proteins or polypeptides according to the invention can be produced by mutagenesis, e.g. by point mutation, lengthening or shortening of the protein.

Homologs of the proteins according to the invention can be identified by screening combinatorial banks of mutants, e.g. shortened mutants. For example, a variegated bank of protein variants can be produced by combinatorial mutagenesis at the nucleic acid level, e.g. by enzymatic ligation of a mixture of synthetic oligonucleotides. There are a large number of methods that can be used for the production of banks of potential homologs from a degenerated oligonucleotide sequence. The chemical synthesis of a degenerated gene sequence can be carried out in an automated DNA synthesizer, and the synthetic gene can then be ligated into a suitable expression vector. The use of a degenerated set of genes makes it possible to provide all sequences, in one mixture, that code for the desired set of potential protein sequences. Methods for the synthesis of degenerated oligonucleotides are known by a person skilled in the art (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

Several techniques for screening gene products of combinatorial banks, that have been produced by point mutations or shortening, and for screening cDNA banks for gene products with a selected property, are known in the prior art. These techniques can be adapted to the rapid screening of gene banks that have been produced by combinatorial mutagenesis of homologs according to the invention. The techniques used most often for screening large gene banks, which form the basis of high-throughput analysis, comprise the cloning of the gene bank into replicatable expression vectors, transforming the suitable cells with the resultant vector bank and expressing the combinatorial genes in conditions in which detection of the desired activity facilitates the isolation of the vector that encodes the gene whose product was detected. Recursive ensemble mutagenesis (REM), a technology that increases the frequency of functional mutants in the banks, can be used in combination with the screening tests, in order to identify homologs (Arkin and Yourvan (1992) PNAS 89:7811-7815; Delgrave et al. (1993) Protein Engineering 6(3):327-331).

2. Nucleic Acids and Constructs 2.1 Nucleic Acids

The invention also relates to nucleic acid sequences that code for an enzyme as described above or a mutant thereof described above with aldoxime dehydratase activity.

The present invention also relates to nucleic acids with a specified degree of identity with the concrete sequences described herein.

"Identity" between two nucleic acids means the identity of the nucleotides over the total nucleic acid length in each case, in particular the identity that is calculated by comparison by means of the Vector NTI Suite 7.1 software from the company Informax (USA) using the Clustal technique (Higgins D G, Sharp P M. Fast and sensitive multiple sequence alignments on a microcomputer. Comput Appl. Biosci. 1989 April; 5(2): 151-1) after setting the following parameters:

Multiple Alignment Parameters:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighting | 0 |

Pairwise alignment parameters:

| | |
|---|---|
| FAST algorithm | on |
| K-tuple size | 1 |
| Gap penalty | 3 |
| Window size | 5 |
| Number of best diagonals | 5 |

As an alternative, the identity can also be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, according to Internet address: http://www.e-bi.ac.uk/Tools/clustalw/index.html# and with the following parameters:

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All nucleic acid sequences mentioned herein (single-stranded and double-stranded DNA and RNA sequences, e.g. cDNA and mRNA) can be produced in a manner known per se by chemical synthesis from the nucleotide building blocks, for example by fragment condensation of individual overlapping, complementary nucleic acid building blocks of the double helix. The chemical synthesis of oligonucleotides can for example take place, in a known manner, by the phosphoroamidite method (Voet, Voet, 2nd edition, Wiley Press New York, pages 896-897). The addition of synthetic oligonucleotides and filling of gaps by means of the Klenow fragment of DNA polymerase and ligation reactions and general cloning techniques are described in Sambrook et al. (1989), Molecular Cloning: A Laboratory Manual, Cold Spring Harbor Laboratory Press.

The invention also relates to nucleic acid sequences (single-stranded and double-stranded DNA and RNA sequences, e.g. cDNA and mRNA), coding for one of the above polypeptides and functional equivalents thereof, which are accessible e.g. by using artificial nucleotide analogs.

The invention relates both to isolated nucleic acid molecules, which code for polypeptides or proteins according to the invention or biologically active segments thereof, and to nucleic acid fragments, which can be used for example as hybridization probes or primers for the identification or amplification of coding nucleic acids according to the invention.

The nucleic acid molecules according to the invention can moreover contain untranslated sequences from the 3'- and/or 5'-end of the coding gene region.

The invention further comprises the nucleic acid molecules complementary to the concretely described nucleotide sequences or a segment thereof.

The nucleotide sequences according to the invention make it possible to produce probes and primers that can be used for the identification and/or cloning of homologous sequences in other cell types and organisms. Said probes or primers usually comprise a nucleotide sequence region that hybridizes under "stringent" conditions (see below) to at least about 12, preferably at least about 25, e.g. about 40, 50 or 75 successive nucleotides of a sense strand of a nucleic acid sequence according to the invention or a corresponding antisense strand.

An "isolated" nucleic acid molecule is separated from other nucleic acid molecules that are present in the natural source of the nucleic acid and can moreover be essentially free from other cellular material or culture medium, when it is produced by recombinant techniques, or free from chemical precursors or other chemicals, when it is synthesized chemically.

A nucleic acid molecule according to the invention can be isolated by means of standard techniques of molecular biology and the sequence information provided according to the invention. For example, cDNA can be isolated from a suitable cDNA bank, using one of the concretely disclosed complete sequences or a segment thereof as hybridization probe and standard hybridization techniques (as described for example in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, N.Y., 1989). Moreover, a nucleic acid molecule, comprising one of the disclosed sequences or a segment thereof, can be isolated by polymerase chain reaction, using the oligonucleotide primers that were prepared on the basis of this sequence. The nucleic acid thus amplified can be cloned into a suitable vector and can be characterized by DNA sequence analysis. The oligonucleotides according to the invention can furthermore be produced by standard methods of synthesis, e.g. with an automated DNA synthesizer.

Nucleic acid sequences according to the invention or derivatives thereof, homologs or portions of these sequences, can be isolated for example with usual hybridization techniques or PCR technology from other bacteria, e.g. via genomic or cDNA banks. These DNA sequences hybridize to the sequences according to the invention under standard conditions.

"Hybridize" means the ability of a poly- or oligonucleotide to bind to an almost complementary sequence under standard conditions, whereas nonspecific binding between non-complementary partners does not occur in these conditions. For this, sequences can be complementary to 90-100%. The property of complementary sequences of being able to bind specifically to one another is utilized, for example, in Northern or Southern Blotting or during primer binding in PCR or RT-PCR.

Advantageously, short oligonucleotides of the conserved regions are used for hybridization. However, longer fragments of the nucleic acids according to the invention or the complete sequences can also be used for hybridization. These standard conditions vary depending on the nucleic acid used (oligonucleotide, longer fragment or complete sequence) or depending on which type of nucleic acid, DNA or RNA, is used for hybridization. For example, the melting temperatures for DNA:DNA hybrids are approx. 10° C. lower than those of DNA:RNA hybrids of the same length.

Standard conditions mean, for example, depending on the nucleic acid, temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide such as for example 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids the hybridization conditions are advantageously 0.1× SSC and temperatures between about 30° C. to 55° C., preferably between about 45° C. to 55° C. These stated temperatures for hybridization are, for example, calculated values of melting temperature for a nucleic acid with a length of approx. 100 nucleotides and a G+C content of 50% in the absence of formamide. The experimental conditions for DNA hybridization are described in relevant genetics textbooks, for example Sambrook et al., "Molecular Cloning", Cold Spring Harbor Laboratory, 1989, and can be calculated using formulas known by a person skilled in the art, for example depending on the length of the nucleic acids, the type of hybrids or the G+C content. A person skilled in the art can obtain further information on hybridization from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

The "hybridization" can in particular take place under stringent conditions. Said hybridization conditions are described for example by Sambrook, J., Fritsch, E. F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions mean in particular: incubation at 42° C. overnight in a solution consisting of 50% formamide, 5×SSC (750 mM NaCl, 75 mM trisodium citrate), 50 mM sodium phosphate (pH 7.6), 5×Denhardt solution, 10% dextran sulfate and 20 g/ml denatured, sheared salmon sperm DNA, followed by a filter washing step with 0.1×SSC at 65° C.

The invention also relates to derivatives of the concretely disclosed or derivable nucleic acid sequences.

Thus, further nucleic acid sequences according to the invention, coding for aldoxime dehydratase, can be derived e.g. from SEQ ID NO:2 or SEQ ID NO:3 and differ from them by addition, substitution, insertion or deletion of single or several nucleotides, but furthermore code for polypeptides with the desired property profile.

The invention also comprises nucleic acid sequences that comprise so-called silent mutations or are altered corresponding to the codon usage of a special original or host organism, compared to a concretely stated sequence, such as SEQ ID NO:3, which is optimized with respect to the codon usage of *E. coli* starting from SEQ ID NO:2, as well as naturally occurring variants, e.g. splice variants or allele variants, thereof.

The invention also relates to sequences obtainable by conservative nucleotide substitutions (i.e. the amino acid in question is replaced with an amino acid of the same charge, size, polarity and/or solubility).

The invention also relates to the molecules derived from the concretely disclosed nucleic acids by sequence polymorphisms. These genetic polymorphisms can exist between individuals within a population owing to natural variation. These natural variations usually produce a variance of 1 to 5% in the nucleotide sequence of a gene.

Derivatives of the nucleic acid sequences according to the invention, coding for aldoxime dehydratase, derived from sequence SEQ ID NO: 3 or from one of the coding sequences for SEQ ID NO:1, mean for example allele variants that have at least 60% homology at the derived amino acid level, preferably at least 80% homology, quite especially preferably at least 90% homology over the whole sequence region (regarding homology at the amino acid level, reference should be made to the above account concerning polypeptides). In partial regions of the sequences, the homologies can advantageously be higher.

Furthermore, derivatives are also to be understood as homologs of the nucleic acid sequences according to the invention, for example fungal or bacterial homologs, shortened sequences, single-stranded DNA or RNA of the coding and noncoding DNA sequence.

Moreover, derivatives mean for example fusions with promoters. The promoters that are joined onto the stated nucleotide sequences can be altered by at least one nucleotide exchange, at least one insertion, inversion and/or deletion, but without impairing the functionality or effectiveness of the promoters. Moreover, the promoters can be increased in effectiveness by altering their sequence, or can be exchanged completely for more effective promoters even of alien organisms.

2.2 Generation of Functional Mutants

Furthermore, methods of production of functional mutants of enzymes according to the invention are known by a person skilled in the art.

Depending on the technology used, a person skilled in the art can introduce completely random or also more targeted mutations into genes or also noncoding nucleic acid regions (which for example are important for the regulation of expression) and then prepare gene banks. The required methods of molecular biology are known by a person skilled in the art and for example are described in Sambrook and Russell, Molecular Cloning. 3rd edition, Cold Spring Harbor Laboratory Press 2001.

Methods for altering genes and therefore for altering the protein encoded by them have long been familiar to a person skilled in the art, for example site-directed mutagenesis, in which individual or several nucleotides of a gene are intentionally exchanged (Trower M K (ed.) 1996; In vitro mutagenesis protocols. Humana Press, New Jersey), saturation mutagenesis, in which a codon for any desired amino acid can be exchanged or added at any desired site of a gene (Kegler-Ebo D M, Docktor C M, DiMaio D (1994) Nucleic Acids Res 22:1593; Barettino D, Feigenbutz M, Valcárel R, Stunnenberg H G (1994) Nucleic Acids Res 22:541; Barik S (1995) Mol Biotechnol 3:1), error-prone polymerase chain reaction (error-prone PCR), in which nucleotide sequences are mutated by defectively working DNA polymerases (Eckert K A, Kunkel T A (1990) Nucleic Acids Res 18:3739);

the SeSaM method (Sequence Saturation Method), in which preferred exchanges are prevented by the polymerase. Schenk et al., Biospektrum, Vol. 3, 2006, 277-279;

the passaging of genes in mutator strains, in which there is an increased mutation rate of nucleotide sequences, for example owing to defective DNA repair mechanisms (Greener A, Callahan M, Jerpseth B (1996) An efficient random mutagenesis technique using an *E. coli* mutator strain. In: Trower M K (ed.) In vitro mutagenesis protocols. Humana Press, New Jersey), or DNA shuffling, in which a pool of closely related genes is formed and digested and the fragments are used as templates for a polymerase chain reaction, in which, by repeated strand separation and reassembly, finally mosaic genes of full length are produced (Stemmer W P C (1994) Nature 370:389; Stemmer W P C (1994) Proc Natl Acad Sci USA 91:10747).

Using so-called directed evolution (described inter alia in Reetz M T and Jaeger K-E (1999), Topics Curr Chem 200:31; Zhao H, Moore J C, Volkov A A, Arnold F H (1999), Methods for optimizing industrial enzymes by directed evolution, In: Demain A L, Davies J E (ed.) Manual of industrial microbiology and biotechnology. American Society for Microbiology), a person skilled in the art can also produce functional mutants in a directed manner and on a large scale. In this, in a first step, firstly gene banks of the respective proteins are produced, for example using the methods given above. The gene banks are expressed in a suitable manner, for example by bacteria or by phage display systems.

The relevant genes of host organisms, which express functional mutants with properties that largely correspond to the desired properties, can be submitted to another round of mutation. The steps of mutation and of selection or screening can be repeated iteratively, until the functional mutants that are present display the desired properties to a sufficient extent. With this iterative procedure, a limited number of mutations, e.g. 1, 2, 3, 4 or 5 mutations, can be performed stepwise, and can be assessed and selected for their influence on the enzyme property in question. The selected mutant can then be submitted to another mutation step in the same way. This can significantly reduce the number of individual mutants to be investigated.

The results according to the invention also provide important information regarding the structure and sequence of the relevant enzymes, which is necessary for directed generation of further enzymes with desired modified properties. In particular, so-called "hot spots" can be defined, i.e. sequence segments that are potentially suitable for modifying an enzyme property through the introduction of directed mutations.

Information can also be derived relating to amino acid sequence positions, in the region of which mutations can be carried out, which should probably have little influence on enzyme activity, and can be designated as potential "silent mutations".

2.3 Constructs

The invention further relates, in particular, to recombinant expression constructs, containing, under the genetic control of regulatory nucleic acid sequences, a nucleic acid sequence coding for a polypeptide according to the invention; and, in particular recombinant, vectors, comprising at least one of these expression constructs.

An "expression unit" means, according to the invention, a nucleic acid with expression activity, which comprises a promoter, as defined herein, and after functional coupling with a nucleic acid to be expressed or a gene, regulates the expression, i.e. the transcription and the translation of this nucleic acid or of this gene. Therefore, in this context we also talk of a "regulatory nucleic acid sequence". In addition to the promoter, other regulatory elements, e.g. enhancers, may also be contained.

An "expression cassette" or "expression construct" means, according to the invention, an expression unit that is linked functionally to the nucleic acid to be expressed or to the gene to be expressed. In contrast to an expression unit, an expression cassette therefore comprises not only nucleic acid sequences that regulate transcription and translation, but also the nucleic acid sequences that should be expressed as protein as a result of transcription and translation.

The terms "expression" or "overexpression" describe, in the context of the invention, the production or increase of the intracellular activity of one or more enzymes in a microorganism, which are encoded by the corresponding DNA. For this it is possible for example to introduce a gene into an organism, replace an existing gene with another gene, increase the copy number of the gene or genes, use a strong promoter or use a gene that codes for a corresponding enzyme with high activity, and these measures can optionally be combined.

Preferably, these constructs according to the invention comprise, 5' upstream of the respective coding sequence, a promoter and 3' downstream a terminator sequence and optionally further usual regulatory elements, in each case operatively coupled to the coding sequence.

A "promoter", a "nucleic acid with promoter activity" or a "promoter sequence" means, according to the invention, a nucleic acid which, functionally coupled to a nucleic acid to be transcribed, regulates the transcription of this nucleic acid.

"Functional" or "operative" coupling means in this context for example the sequential arrangement of one of the nucleic acids with promoter activity and a nucleic acid sequence to be transcribed and optionally other regulatory elements, for example nucleic acid sequences that ensure the transcription of nucleic acids, and for example a terminator, so that each of the regulatory elements can fulfill its function during transcription of the nucleic acid sequence. This does not necessarily require direct coupling in the chemical sense. Genetic control sequences, for example enhancer sequences, can exert their function on the target sequence even from more remote positions or even from other DNA molecules. Arrangements are preferred in which the nucleic acid sequence to be transcribed is positioned behind (i.e. at the 3'-end of) the promoter sequence, so that the two sequences are joined together covalently. Moreover, the distance between the promoter sequence and the nucleic acid sequence to be expressed transgenically can be smaller than 200 base pairs, or smaller than 100 base pairs or smaller than 50 base pairs.

In addition to promoters and terminator, as examples of other regulatory elements we may mention targeting sequences, enhancers, polyadenylation signals, selectable markers, amplification signals, replication origins and the like. Suitable regulatory sequences are described e.g. in Goeddel, Gene Expression Technology: Methods in Enzymology 185, Academic Press, San Diego, Calif. (1990).

Nucleic acid constructs according to the invention comprise in particular a sequence coding for an aldoxime dehydratase mutant, in particular one derived from the nucleic acid sequence coding for a PAOx according to SEQ ID NO:1 and to the codon usage of E. coli SEQ ID NO: 3 or derivatives and homologs thereof, and the nucleic acid sequences derivable therefrom, which are coupled operatively or functionally with one or more regulatory signals advantageously for controlling, e.g. increasing, gene expression.

In addition to these regulatory sequences, the natural regulation of these sequences can still be present before the actual structural genes and optionally can be genetically altered, so that the natural regulation is switched off and expression of the genes is increased. The nucleic acid construct can, however, also be of simpler construction, i.e. without inserting any additional regulatory signals before the coding sequence and without removing the natural promoter with its regulation. Instead, the natural regulatory sequence is mutated so that regulation no longer takes place and gene expression is increased.

A preferred nucleic acid construct advantageously also contains one or more of the "enhancer" sequences already mentioned, functionally coupled to the promoter, which make increased expression of the nucleic acid sequence possible. Additional advantageous sequences, such as other regulatory elements or terminators, can also be inserted at the 3'-end of the DNA sequences. The nucleic acids according to the invention can be contained in one or more copies in the construct. The construct can contain yet other markers, such as antibiotic resistances or auxotroph-complementary genes, optionally for selection on the construct.

Examples of suitable regulatory sequences are contained in promoters such as cos, tac, trp, tet, trp-tet, lpp, lac, lpp-lac, lacI$^{q-}$, T7, T5, T3, gal, trc, ara, rhaP (rha$_{BAD}$)SP6, lambda-P$_R$ or in the lambda-P$_L$ promoter, which find application advantageously in Gram-negative bacteria. Further advantageous regulatory sequences are contained for example in the Gram-positive promoters amy and SPO2, in the yeast or fungus promoters ADC1, MFalpha, AC, P-60, CYC1, GAPDH, TEF, rp28, ADH. Artificial promoters can also be used for regulation.

For expression in a host organism, advantageously the nucleic acid construct is inserted into a vector, for example a plasmid or a phage, which makes optimal expression of the genes in the host possible. Apart from plasmids and phages, vectors are also to be understood as all other vectors known by a person skilled in the art, e.g. viruses, such as SV40, CMV, baculovirus and adenovirus, transposons, IS elements, phasmids, cosmids, and linear or circular DNA. These vectors can replicate autonomously in the host organism or can be replicated chromosomally. These vectors represent a further embodiment of the invention.

Suitable plasmids are for example in E. coli pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCl, in Streptomyces pIJ101, pIJ364, pIJ702 or pIJ361, in Bacillus pUB110, pC$_{194}$ or pBD214, in Corynebacterium pSA77 or pAJ667, in fungi pALS1, pIL2 or pBB116, in yeasts 2alphaM, pAG-1, YEp6, YEp13 or pEMBLYe23 or in plants pLGV23, pGHlac+, pBIN19, pAK2004 or pDH51. The plasmids mentioned represent a small selection of the possible plasmids. Further plasmids are certainly known by a person skilled in the art and can for example be found in the book Cloning Vectors (Eds. Pouwels P. H. et al. Elsevier, Amsterdam-New York-Oxford, 1985, ISBN 0 444 904018).

In another embodiment of the vector, the vector containing the nucleic acid construct according to the invention or the nucleic acid according to the invention can also advantageously be introduced in the form of a linear DNA into the microorganisms and be integrated by heterologous or homologous recombination into the genome of the host organism. This linear DNA can consist of a linearized vector such as a plasmid or only of the nucleic acid construct or the nucleic acid according to the invention.

For optimal expression of heterologous genes in organisms, it is advantageous to alter the nucleic acid sequences corresponding to the specific "codon usage" used in the organism. The "codon usage" can easily be determined on the basis of computer evaluations of other, known genes of the organism in question.

An expression cassette according to the invention is prepared by fusion of a suitable promoter with a suitable coding nucleotide sequence and a terminator signal or polyadenylation signal. Common recombination and cloning techniques are used for this, such as are described for example in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector, which makes optimal expression of the genes in the host possible. Vectors are certainly known by a person skilled in the art and can be found for example in "Cloning vectors" (Pouwels P. H. et al., Ed., Elsevier, Amsterdam-New York-Oxford, 1985).

3. Microorganisms

Depending on context, the term "microorganism" can mean the wild-type microorganism or a genetically modified, recombinant microorganism, or both.

By means of the vectors according to the invention, recombinant microorganisms can be produced, which for example are transformed with at least one vector according to the invention and can be used for production of the polypeptides according to the invention. Advantageously, the recombinant constructs according to the invention, described above, are introduced into a suitable host system and expressed. Cloning and transfection methods are used that are familiar to a person skilled in the art, for example co-precipitation, protoplast fusion, electroporation, retroviral transfection and the like, for expressing the stated nucleic acids in the respective expression system. Suitable systems are described for example in Current Protocols in Molecular Biology, F. Ausubel et al., Ed., Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, N.Y., 1989.

In principle, all prokaryotic or eukaryotic organisms may be considered as recombinant host organisms for the nucleic acid according to the invention or the nucleic acid construct. Advantageously, microorganisms such as bacteria, fungi or yeasts are used as host organisms. Advantageously, Gram-positive or Gram-negative bacteria are used, preferably bacteria of the families Enterobacteriaceae, Pseudomonadaceae, Rhizobiaceae, Streptomycetaceae or Nocardiaceae, especially preferably bacteria of the genera *Escherichia, Pseudomonas, Streptomyces, Nocardia, Burkholderia, Salmonella, Agrobacterium, Clostridium* or *Rhodococcus*. The genus and species *Escherichia coli* is quite especially preferred. Other advantageous bacteria are to be found, moreover, in the group of alpha-proteobacteria, beta-proteobacteria or gamma-proteobacteria.

The host organism or the host organisms according to the invention preferably contain at least one of the nucleic acid sequences, nucleic acid constructs or vectors described in this invention, which code for an enzyme with phenylethanol dehydrogenase activity according to the above definition.

The organisms used in the process according to the invention are, depending on the host organism, grown or cultured in a manner known by a person skilled in the art. Microorganisms are as a rule grown in a liquid medium that contains a carbon source generally in the form of sugars, a nitrogen source generally in the form of organic nitrogen sources such as yeast extract or salts such as ammonium sulfate, trace elements such as iron, manganese, magnesium salts and optionally vitamins, at temperatures between 0° C. and 100° C., preferably between 10° C. and 60° C. with oxygen aeration. During this, the pH of the nutrient liquid can be held at a fixed value, i.e. may or may not be regulated during culture. Culture can be batchwise, semi-batchwise or continuous. Nutrients can be supplied at the start of fermentation or can be fed in semicontinuously or continuously.

4. Recombinant Production of Enzymes According to the Invention

The invention further relates to methods for recombinant production of polypeptides according to the invention or functional, biologically active fragments thereof, wherein a polypeptide-producing microorganism is cultivated, optionally the expression of the polypeptides is induced and these are isolated from the culture. The polypeptides can also be produced in this way on an industrial scale, if desired.

The microorganisms produced according to the invention can be cultivated continuously or discontinuously in a batch process or in a fed-batch or repeated fed-batch process. A review of known culture techniques can be found in Chmiel's textbook (Bioprocess Technology 1. Introduction to bioprocess engineering (Gustav Fischer Verlag, Stuttgart, 1991)) or in the textbook by Storhas (Bioreactors and Peripheral Equipment (Vieweg Verlag, Braunschweig/Wiesbaden, 1994)).

The culture medium to be used has to satisfy the requirements of the respective strains in a suitable manner. Descriptions of culture media for various microorganisms are given in "Manual of Methods for General Bacteriology" of the American Society for Bacteriology (Washington D.C., USA, 1981).

These media for use according to the invention usually comprise one or more carbon sources, nitrogen sources, inorganic salts, vitamins and/or trace elements.

Preferred carbon sources are sugars, such as mono-, di- or polysaccharides. Very good carbon sources are for example glucose, fructose, mannose, galactose, ribose, sorbose, ribulose, lactose, maltose, sucrose, raffinose, starch or cellulose. Sugars can also be added to the media via complex compounds, such as molasses, or other by-products of sugar refining. It may also be advantageous to add mixtures of various carbon sources. Other possible carbon sources are oils and fats e.g. soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Nitrogen sources are usually organic or inorganic nitrogen compounds or materials that contain these compounds. Examples of nitrogen sources comprise ammonia gas or ammonium salts, such as ammonium sulfate, ammonium chloride, ammonium phosphate, ammonium carbonate or ammonium nitrate, nitrates, urea, amino acids or complex nitrogen sources, such as corn-steep liquor, soya flour, soya protein, yeast extract, meat extract and others. The nitrogen sources can be used individually or as a mixture.

Inorganic salt compounds that can be contained in the media comprise the chloride, phosphorus or sulfate salts of calcium, magnesium, sodium, cobalt, molybdenum, potassium, manganese, zinc, copper and iron.

The source of sulfur used can be inorganic sulfur-containing compounds, for example sulfates, sulfites, dithionite, tetrathionate, thiosulfates, sulfides but also organic sulfur compounds, such as mercaptans and thiols.

Phosphoric acid, potassium dihydrogen phosphate or dipotassium hydrogen phosphate or the corresponding sodium-containing salts can be used as the source of phosphorus.

Chelating agents can be added to the medium in order to keep the metal ions in solution. Especially suitable chelating agents comprise dihydroxyphenols, such as catechol or protocatechuate, or organic acids, such as citric acid.

The fermentation media used according to the invention usually also contain other growth factors, such as vitamins or growth promoters, including for example biotin, riboflavin, thiamine, folic acid, nicotinic acid, pantothenate and pyridoxine. Growth factors and salts often originate from complex components of the media, such as yeast extract, molasses, corn-steep liquor and the like. Moreover, suitable precursors can be added to the culture medium. The precise composition of the compounds in the media depends largely on the particular experiment and is decided individually for each specific case. Information on optimization of the media can be found in the textbook "Applied Microbiol. Physiology, A Practical Approach" (ed. P. M. Rhodes, P. F. Stanbury, IRL Press (1997) p. 53-73, ISBN 0 19 963577 3). Growing media can also be obtained from commercial suppliers, such as Standard 1 (Merck) or BHI (brain heart infusion, DIFCO) and the like.

All components of the media are sterilized, either with heat (20 min at 1.5 bar and 121° C.) or by sterile filtration. The components can be sterilized either together, or separately if necessary. All components of the media can be present at the start of culture or optionally are added continuously or batchwise.

The culture temperature is normally between 15° C. and 45° C., preferably 25° C. to 40° C. and can be kept constant or can be varied during the experiment. The pH of the medium should be in the range 5 to 8.5, preferably around 7.0. The culture pH can be controlled during culture by adding basic compounds such as sodium hydroxide, potassium hydroxide, ammonia or ammonia water or acidic compounds such as phosphoric acid or sulfuric acid. Antifoaming agents, such as fatty acid polyglycol esters, can be used for controlling foam formation. To maintain the stability of plasmids, suitable substances with selective action, e.g. antibiotics, can be added to the medium. To maintain aerobic conditions, oxygen or oxygen-containing gas mixtures, e.g. ambient air, are fed into the culture. The culture temperature is normally 20° C. to 45° C. Culture is continued until a maximum of the desired product has formed. This target is normally reached within 10 hours to 160 hours.

The fermentation broth is then processed further. Depending on requirements, the biomass can be removed from the fermentation broth completely or partially by separation techniques, e.g. centrifugation, filtration, decanting or a combination of these methods, or can be left in it completely.

If the polypeptides are not secreted into the culture medium, the cells can also be lysed and the product can be obtained from the lysate by known methods for protein isolation. The cells can optionally be lysed by high-frequency ultrasound, by high pressure, such as in a French pressure cell, by osmolysis, by the action of detergents, lytic enzymes or organic solvents, by means of homogenizers or by combining several of the methods listed.

The polypeptides can be purified by known chromatographic techniques, such as molecular-sieve chromatography (gel filtration), such as Q-sepharose chromatography, ion exchange chromatography and hydrophobic chromatography, and with other usual methods such as ultrafiltration, crystallization, salting out, dialysis and native gel electrophoresis. Suitable methods are described for example in Cooper, T. G., Biochemical Procedures, Verlag Walter de Gruyter, Berlin, New York or in Scopes, R., Protein Purification, Springer Verlag, New York, Heidelberg, Berlin.

For isolating the recombinant protein, it may be advantageous to use vector systems or oligonucleotides, which extend the cDNA by defined nucleotide sequences and therefore code for altered polypeptides or fusion proteins, which serve for example for simpler purification. Suitable modifications of this kind are for example so-called "Tags" functioning as anchors, e.g. the modification known as hexa-histidine anchor or epitopes, which can be recognized as antigens by antibodies (described for example in Harlow, E. and Lane, D., 1988, Antibodies: A Laboratory Manual. Cold Spring Harbor (N.Y.) Press). These anchors can serve for attaching the proteins to a solid carrier, e.g. a polymer matrix, which can for example be filled in a chromatography column, or can be used on a microtiter plate or on some other carrier.

At the same time, these anchors can also be used for recognition of the proteins. For recognition of the proteins, it is moreover possible to use usual markers, such as fluorescent dyes, enzyme markers, which after reaction with a substrate form a detectable reaction product, or radioactive markers, alone or in combination with the anchors for derivatization of the proteins.

5. Enzyme Immobilization

The enzymes according to the invention can be used free or immobilized in the process described herein. An immobilized enzyme is to be understood as an enzyme that is fixed to an inert carrier. Suitable carrier materials and the enzymes immobilized thereon are known from EP-A-1149849, EP-A-1 069 183 and DE-OS 100193773 and from the literature references cited therein. Reference is made to the relevant disclosure of these documents in its entirety. Suitable carrier materials include for example clays, clay minerals, such as kaolinite, diatomaceous earth, perlite, silicon dioxide, aluminum oxide, sodium carbonate, calcium carbonate, cellulose powder, anion exchanger materials, synthetic polymers, such as polystyrene, acrylic resins, phenol-formaldehyde resins, polyurethanes and polyolefins, such as polyethylene and polypropylene. For production of the supported enzymes, the carrier materials are usually employed in a finely-divided, particulate form, porous forms being preferred. The particle size of the carrier material is usually not more than 5 mm, in particular not more than 2 mm (particle-size distribution curve). Similarly, when using dehydrogenase as whole-cell catalyst, a free or immobilized form can be selected. Carrier materials are e.g. Ca-alginate, and carrageenan. Enzymes as well as cells can also be crosslinked directly with glutaraldehyde (crosslinking to CLEAs). Corresponding and further immobilization techniques are described for example in J. Lalonde and A. Margolin "Immobilization of enzymes" in K. Drauz and H. Waldmann, Enzyme Catalysis in Organic Synthesis 2002, Vol. III, 991-1032, Wiley-VCH, Weinheim. Further information on biotransformations and bioreactors for carrying out methods according to the invention are also given for example in Rehm et al. (Ed) Biotechnology, 2nd Edn, Vol 3, Chapter 17, VCH, Weinheim.

6. Biocatalytic Production of Nitriles

The biocatalytic process according to the invention for producing nitriles from corresponding oximes is carried out in the presence of an aldoxime dehydratase, in particular an aliphatic aldoxime dehydratase (4.99.1.5), a phenylacetaldoxime dehydratase (PAOx) (EC 4.99.1.7) or an indoleacetaldoxime dehydratase (4.99.1.6). Examples of said enzymes comprise at least one amino acid sequence according to SEQ ID NO: 1 or 4 to 28, or an amino acid sequence identical to this to at least 60%, e.g. at least 65, 70, 75, 80, 85, 90, 91, 92, 93, 94, 95, 96, 97, 98, or 99%; or wherein up to 25%, e.g. up to 20, 15, 10, 9, 8, 7, 6, 5, 4, 3, 2 or 1% of the amino acid residues are altered relative to one of the sequences according to SEQ ID NO:1 or 4 to 28 by addition, deletion, insertion, substitution, inversion or a combination thereof, and which still has at least 50%, e.g. at least 60, 65, 70, 75, 80, 85, 90 or 95% of the enzymatic activity of SEQ ID NO:1.

In particular, the process according to the invention is carried out in the presence of an enzyme, wherein the enzyme has the protein sequence according to SEQ ID NO:1. In particular, the enzyme is encoded by a nucleic acid sequence according to SEQ ID NO:2 or a functional equivalent thereof, in particular a functional equivalent according to SEQ ID NO:3, which represents a nucleic acid sequence codon-optimized for expression in the *E. coli* microorganism. Moreover, the nucleic acid sequence is in particular a constituent of a gene construct or vector. These gene constructs or vectors are described in detail in international application PCT/EP2010/057696 on pages 16 to 20, which is expressly referred to herein.

The host cell, which contains a gene construct or a vector, which contains the nucleic acid sequence that codes for the enzyme with the desired activity, is also designated as transgenic organism. The production of said transgenic organisms is known in principle and is discussed for example in international application PCT/EP2010/057696 on page 20, which is expressly referred to herein.

Cells selected from the group consisting of bacteria, cyanobacteria, fungi and yeasts are preferred as transgenic organisms. Preferably the cell is selected from fungi of the genus *Pichia* or bacteria of the genera *Escherichia*, *Corynebacterium*, *Ralstonia*, *Clostridium*, *Pseudomonas*, *Bacillus*, *Zymomonas*, *Rhodobacter*, *Streptomyces*, *Burkholderia*, *Lactobacillus* or *Lactococcus*. Especially preferably, the cell is selected from bacteria of the species *Escherichia coli*, *Pseudomonas putida*, *Burkholderia glumae*, *Streptomyces lividans*, *Streptomyces coelicolor* or *Zymomonas mobilis*.

A process according to the invention is preferred that is characterized in that the enzyme with the activity of an aldoxime dehydratase, in particular of an aliphatic aldoxime dehydratase (EC 4.99.1.5), a phenylacetaldoxime dehydratase (also designated as PAOx herein) (EC 4.99.1.7) or an indoleacetaldoxime dehydratase (EC 4.99.1.6), is encoded by a gene that was isolated from a microorganism selected from *Zymomonas mobilis*, *Methylococcus capsulatus*, *Rhodopseudomonas palustris*, *Bradyrhizobium japonicum*, *Frankia* spec, *Streptomyces coelicolor*, *Acetobacter pasteurianus* and *Absidia* sp., such as *A. corymbifera*; *Agrobacterium* sp., such as *A. radiobacter*; *Alcaligenes* sp., such as *A. faecalis*; *Arthrobacter* sp., such as *A. crystallopoietes* or *A. ramosus*; *Aspergillus* sp., such as *A. amstelodami*, *A. celluosae*; *A. candidus* or *A. pulverulentus*; *Aureobacterium* sp., such as *A. testaceum*; *Aureobasidium* sp., such as *A. pullulans*; *Bacillus* sp., such as *B. coagulans*, *B. megaterium*, *B.* sp. OxB-1 or *B. subtilis*; *Botryotinia* sp., such as *Botryotinia fuckeliana*; *Brevibacterium* sp., such as *B. butanicum*; *Cellulomonas* sp., such as *C. fimi*; *Coprinus* sp., such as *C. phlyctidosporus*; *Corynebacterium* sp, such as *C. paurometabolum* or *C. rathavi*; *Cunninghamella* sp., such as *C. echinulata* var. *Elegans*; *Flammulina* sp., such as *F.* sp. strain TPU 4675 or *F. velutipes*; *Flavobacterium* sp., such as *F. aquatile*, *F. lutescens*, *F. rigense* or *F. suaveolens*; *Fusarium* sp., such as *F. culmorum*, *F. oxysporum* f. sp. *Nicotianae* or *F. solani* var. *martii*; *Gibberella* sp., such as *Gibberella fujikuori* or *Gibberella zeae*; *Keratinomyces* sp., such as *K. ajelloi*; *Klebsiella* sp., such as *K. pneumoniae*; *Leptosphaeria* sp., such as *Leptosphaeria maculans*; *Micrococcus* sp.; such as *M. luteus* or *M. ureae*; *Mortierella* sp., such as *M. isabellina*; *M. ramanniana* var. *Angulispora* or *M.* sp. TPU 4801; *Mucor* sp., such as *M. fragilis*; *Neosartorya* sp. such as *N. fisheri*; *Nocardia* sp., such as *N. asteroides*; *Phycomyces* sp., such as *P. nitens*; *Proteus* sp., such as *P. vulgaris*; *Pseudomonas* sp., such as *Pseudomonas chloraphis* or *P. fluorescens*; *Pycnoporos* sp., such as *P. coccineus*; *Rhizoctonia* sp., such as *Rhizoctonia solani*; *Rhizopus*, such as *R. nigricans* or *R. oryzae*; *Rhodococcus* sp., such as *R. erythropolis* or *R. rhodochrous*; *Schizophyllum* sp., such as *S. commune* or *S.* sp. strain TPU 4435; *Sclerotinia* sp., such as *Sclerotinia sclerotiorum*; *Talaromyces* sp., such as *T. flavus*; *Serratia* sp., such as *S. marcescens*; *Stenotrophomonas* sp., such as *S. maltophilia*; *Xanthomonas* sp., such as *X. flavus*. The relevant genes, in particular the gene for PAOx, isolated from *Rhodococcus* sp., *Gibberella zeae* or in particular *Bacillus* sp., are especially preferred.

Examples of aliphatic acetaldoxime dehydratases that are suitable for use in the context of a process according to the invention or whose sequences are suitable as a starting point for the production of functional equivalents are shown in Table 1 below. The access numbers refer to the specialist databases REFSEQ and UNIPROT, wherein a person skilled in the art can readily access the sequence entries identified by access numbers via Internet-based services as well as other databases such as GeneBank or SwissProt.

TABLE 1

| SEQ ID NO: | Access number | Description | EC No. | Organism |
|---|---|---|---|---|
| 4 | YP_947647 (NCIB) | Aldoxime dehydratase | 4.99.1.5 | *Arthrobacter aurescens* TC1 |
| 5 | Q6FBU3 | Aldoxime dehydratase | 4.99.1.5 | *Acinetobacter* sp. strain ADP1 |

Examples of phenylacetaldoxime dehydratases that are suitable for use in the context of a process according to the invention or whose sequences are suitable as the starting point for the production of functional equivalents are shown in Table 2 below:

TABLE 2

| SEQ ID NO: | Access number | Description | EC No. | Organism |
|---|---|---|---|---|
| 6 | F0QD95_ACIAP | Phenylacetaldoxime dehydratase | 4.99.1.7 | *Acidovorax avenae*-strain ATCC 19860 |

TABLE 2-continued

| SEQ ID NO: | Access number | Description | EC No. | Organism |
|---|---|---|---|---|
| | | | | DSM 7227 JCM 20985 NCPPB 1011 |
| 7 | YP_003097901 | Phenylacetaldoxime dehydratase | 4.99.1.7 | *Actinosynnema mirum* DSM 43827 |
| 8 | YP_001240697 | Presumed phenylacetaldoxime dehydratase | 4.99.1.7 | *Bradyrhizobium* sp. BTAi1 |
| 9 | ZP_02891657 | Phenylacetaldoxime dehydratase | 4.99.1.7 | *Burkholderia ambifaria* iOP40-10 |
| 10 | YP_001816246 | Phenylacetaldoxime dehydratase [*Burkholderia ambifaria* MC40-6]. | 4.99.1.7 | *Burkholderia ambifaria* MC40-6 |
| 11 | YP_001776877 | Phenylacetaldoxime dehydratase [*Burkholderia cenocepacia* MC0-3]. | 4.99.1.7 | *Burkholderia cenocepacia* MC0-3 |
| 12 | YP_004119277 | Phenylacetaldoxime dehydratase [*Pantoea* sp. At-9b]. | 4.99.1.7 | *Pantoea* sp. At-9b |
| 13 | ZP_07774756 | Phenylacetaldoxime dehydratase [*Pseudomonas fluorescens* WH6]. | 4.99.1.7 | *Pseudomonas fluorescens* WH6 |
| 14 | ZP_07774757 | Phenylacetaldoxime dehydratase [*Pseudomonas fluorescens* WH6]. | 4.99.1.7 | *Pseudomonas fluorescens* WH6 |
| 15 | YP_001268042 | Phenylacetaldoxime dehydratase [*Pseudomonas putida* F1]. | 4.99.1.7 | *Pseudomonas putida* F1 |
| 16 | E4RFH2_PSEPB | Phenylacetaldoxime dehydratase | 4.99.1.7 | *Pseudomonas putida* strain BIRD-1 |
| 17 | YP_001758607 | Phenylacetaldoxime dehydratase [*Shewanella woodyi* ATCC 51908]. | 4.99.1.7 | *Shewanella woodyi* ATCC 51908 |
| 18 | YP_001261493 | Phenylacetaldoxime dehydratase [*Sphingomonas wittichii* RW1]. | 4.99.1.7 | *Sphingomonas wittichii* RW1 |
| 19 | YP_004155682 | Phenylacetaldoxime dehydratase [*Variovorax paradoxus* EPS]. | 4.99.1.7 | *Variovorax paradoxus* EPS |
| 20 | YP_002942593 | Phenylacetaldoxime dehydratase [*Variovorax paradoxus* S110]. | 4.99.1.7 | *Variovorax paradoxus* S110 |
| 21 | YP_002944432 | Phenylacetaldoxime dehydratase [*Variovorax paradoxus* S110]. | 4.99.1.7 | *Variovorax paradoxus* S110 |
| 22 | YP_001416464 | Phenylacetaldoxime dehydratase [*Xanthobacter autotrophicicus* Py2]. | 4.99.1.7 | *Xanthobacter autotrophicicus* Py2 |

An example of an indoleacetaldoxime dehydratase that is suitable for use in the context of a process according to the invention or whose sequence is suitable as the starting point for the production of functional equivalents is shown in Table 3 below:

TABLE 3

| SEQ ID NO: | Access number | Description | EC No. | Organism |
|---|---|---|---|---|
| 28 | O49342 | Indoleacetaldoxime dehydratase; EC 4.99.1.6 | 4.99.1.6 | *Arabidopsis thaliana* |

According to another embodiment, the enzyme has an amino acid sequence that is derived from one of the aldoxime dehydratases given in Tables 1 to 3 as starting sequence and has, compared to the relevant starting sequence, an amino acid sequence that is identical to at least 60%, for instance at least 75%, at least 80%, at least 90%, at least 95%, at least 96%, at least 97%, at least 98% or at least 99%. An especially preferred embodiment of the process envisages, as enzyme, a PAOx according to SEQ ID NO:1 (Kato, Y. et al., Biochemistry (2000), 39, 800-809 and Xie, S-X. et al., Biosci. Biotechnol. Biochem. (2001), 65(12), 2666-2672), or a PAOx with an amino acid sequence identical to SEQ ID NO:1 to at least 60%, for instance at least 75%, at least 80%, at least 90%, at least 95%, at least 96%, at least 97%, at least 98% or at least 99%.

In one embodiment of the process according to the invention, an oxime of formula II is reacted, in which the residue R together with the carbon atom to which it is bound is derived from a noncyclic terpene residue, selected from hemiterpene ($C_5$), monoterpene ($C_{10}$), sesquiterpene ($C_{15}$), diterpene ($C_{20}$), sesterterpene ($C_{26}$), triterpene ($C_{30}$) or tetraterpene ($C_{40}$) residues (in particular by partial or complete hydrogenation), or is derived from corresponding terpene residues that are shortened by 1 to 3 carbon atoms.

In another preferred embodiment of the process, an oxime of formula II is reacted, in which n stands for 1 and the residue R stands for a linear or singly or multiply branched, saturated or singly or multiply unsaturated, optionally singly or multiply substituted aliphatic hydrocarbon residue with 4 to 19 carbon atoms.

In special embodiments of a process according to the invention, we have an oxime of general formula II, i.e. an aldoxime, wherein n stands for 1 and the oxime is selected from compounds shown in the following Table 4, which differ by different residues R linked to the oxime group:

TABLE 4

$$R{-}[C{=}N{-}OH]_n$$
$$(II)$$
$$n = 1$$

| | Structure | Name |
|---|---|---|
| 1 | | Citral oxime (3,7-dimethyl-octa-2,6-dienal oxime) |
| 2 | | Neral oxime |
| 3 | | Geranial oxime |
| 4 | | Ethylgeranial oxime |
| 5 | | Melonal oxime |
| 6 | | Nonadienal oxime |
| 7 | | Hydroxycitronellal oxime |
| 8 | | Heptanal oxime |

TABLE 4-continued

R—[C=N—OH]$_n$
(II)
n = 1

| | | Name |
|---|---|---|
| 9 | 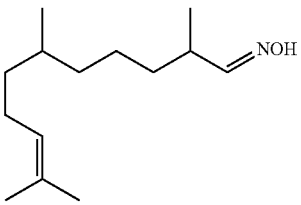 | 2,6,10-Trimethyl-9-undecenal oxime |
| 10 | 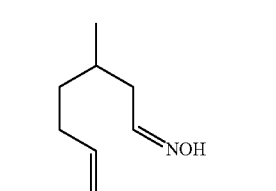 | Citronellal oxime |

The residue R can moreover be selected from analogs of compounds 1-6, 9 and 10 in Table 4, wherein the residue R is hydrogenated. In special embodiments the oxime is selected from compound 1 (citral oxime), compound 2 (neral oxime), compound 3 (geranial oxime) and compound 10 (citronellal oxime) and partially or fully hydrogenated analogs thereof. An example of a compound with hydrogenated residue R is compound 10 (citronellal oxime) in hydrogenated form (i.e. 6,7-dihydrocitronellyl oxime, which is reacted in the context of the process according to the invention to 6,7-dihydrocitronellyl nitrile).

In the process according to the invention, two or more oximes of formula II in each case with different residues R and/or different indices n can be present simultaneously, so that a product mixture of corresponding nitriles of formula I is formed. Preferably, however, exactly one oxime of a corresponding formula II is used.

According to a special embodiment of the process according to the invention, citronellal oxime of formula IIa

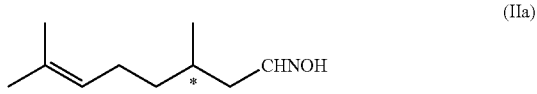

(IIa)

is reacted to citronellyl nitrile of formula Ia

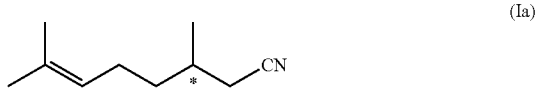

(Ia)

using the compound of formula IIa, in stereoisomerically pure form or as stereoisomeric mixture, such as in particular as R/S-E/Z mixture.

A reaction according to the invention in the presence of an oxime dehydratase, in particular an aliphatic aldoxime dehydratase (EC 4.99.1.5), a phenylacetaldoxime dehydratase (PAOx) (EC 4.99.1.7) or an indoleacetaldoxime dehydratase (EC 4.99.1.6) can in particular take place as follows:

a) Reaction in the presence of the aldoxime dehydratase
b) Reaction in the presence of a protein mixture containing the aldoxime dehydratase
c) Reaction in the presence of a recombinant microorganism functionally expressing the aldoxime dehydratase, an aldoxime dehydratase-containing cell homogenate derived therefrom or an aldoxime dehydratase-containing fraction thereof.

Preferably the aldoxime dehydratase is PAOx, optionally together with other aldoxime dehydratases. On expression in recombinant microorganisms, surprisingly high yields are achieved, for example yields of more than 70% and up to essentially quantitative yields, relative to the substrate used. The reactions can, among other things, even take place at low temperatures, for example at 15° C.-60° C., preferably 25° C.-45° C., for instance at temperatures of about 30° C.

The reaction in the presence of the aldoxime dehydratase can for example relate to
  i. free, optionally purified or partially purified polypeptide
  ii. immobilized polypeptide, and/or
  iii. polypeptide isolated from cells.

In a reaction according to the aforementioned option c) in the presence of microorganisms that functionally express an aldoxime dehydratase, they are whole cells, which can be in any phase of cell culture, for example dormant or growing, and contain at least one aldoxime dehydratase polypeptide.

In preferred embodiments the aldoxime dehydratase is a PAOx, or a mixture of aldoxime dehydratase comprises, besides other aldoxime dehydratases, a PAOx.

In the context of a process according to the invention, the enzyme with aldoxime dehydratase activity can in particular be generated by a microorganism that overproduces the enzyme. The microorganism can in particular be selected from the group of microorganisms consisting of the genera *Leptosphaeria*, such as *Leptosphaeria maculans*; *Rhizoctonia*, such as *Rhizoctonia solani*; *Sclerotinia*, such as *Sclerotinia sclerotiorum*; *Botryotinia*, such as *Botryotinia fuckeliana*; *Pseudomonas*, such as *Pseudomonas chloraphis*; *Rhodococcus*; *Gibberella*, such as *Gibberella fujikuroi* or *Gibberella zeae*; *Escherichia*, *Pichia*, *Aspergillus*, *Trichoderma* or *Bacillus*, such as *Escherichia coli* or *Pichia pastoris*; and *Saccharomyces*, such as *Saccharomyces cerevisiae*. Table 6 contains a list with further suitable microorganisms, wherein the underlying genera of the species stated there represent suitable examples. Alternatively, an aldoxime dehydratase can also be isolated from plants as overexpressing organisms and can be used in the sense of options i) or ii) given above in the context of a process according to the invention. For example *Musa* (in particular *M. acuminata* banana) and *Arabidopsis* (in particular *A. thaliana*) may come into consideration as overexpressing plants. Overexpressing microorganisms or plants can be determined by a person skilled in the art in a manner known in the prior art by screening for overexpressing representatives. Alternatively, overexpression can be induced by genetically engineered intensification of expression of a gene occurring naturally in the microorganisms or plants, which expresses an aldoxime dehydratase, for example by inserting stronger promoters to increase transcription.

According to a special embodiment, a reaction of an oxime of formula II takes place in the presence of a microorganism, wherein the microorganism is a bacterial strain, which functionally expresses aldoxime dehydratase, preferably PAOx. The bacterial strain can for example be selected from *Escherichia coli*, *Pseudomonas putida*, *Burkholderia glumae*, *Corynebacterium glutamicum*, *Bacillus subtilis* or *Zymomo-* nas mobilis. According to special embodiments, the bacterial strain is an *E. coli* strain. The microorganism is in particular a recombinant microorganism, into which a heterologous gene of an oxime dehydratase, in particular a gene for PAOx, has been inserted.

In a further special embodiment the microorganism carries an expression construct, which has a nucleic acid sequence coding for aldoxime dehydratase. The nucleic acid sequence can be partially or fully adapted to the codon usage of the microorganism. Adaptation is complete when all codons of all amino acids are altered so that optimum translation takes place in the microorganism envisaged, unless an optimal codon was already present. Adaptation is assumed to be partial if only the codons of selected amino acids are optimized, not those of all amino acids, or if not all the codons of in each case one amino acid occurring within the nucleic acid sequence are optimized.

According to another preferred embodiment of the process according to the invention, the microorganism expresses at least one chaperone, which supports the functional expression of aldoxime dehydratase, which can in particular be PAOx. Functional expression can in particular be supported by the chaperone supporting the correct folding of the expressed oxime dehydratase, in particular during or subsequent to translation. Through the expression of chaperones, advantageously the proportion of functional aldoxime dehydratase in the microorganism can be increased and the conversion of oxime to nitrile can be increased.

In the context of the process according to the invention, it can in particular be envisaged that the microorganism expresses one or more chaperones, which are selected from GroEL and GroES. A person skilled in the art knows further chaperones, which are divided into five broad families, namely the Hsp100/Clp family, the Hsp90 family, the Hsp70 family (with for example DnaK, DNAJ, Hsc62, Hsc56, and GrpE as representatives in *E. coli*), the Hsp60/GroEL family (with the GroEL already mentioned) and the family of small heat shock proteins (Hsp20). Chaperones can also be selected from these protein families. Combinations can also be formed, for example from the Dank/DnaJ/GrpE complex, the GroEL/ES complex and Trigger Factor, as described for example in O'Donnell and L is, MIT 7.88 Research Paper, 2006. The chaperone or chaperones can be expressed endogenously in the microorganism used, or expressed partially or completely by nucleic acid sequences introduced additionally into the microorganism. These nucleic acid sequences can be introduced into the genome of the microorganism, for example into a bacterial chromosome, or can be present extrachromosomally on expression constructs. If an aldoxime dehydratase is expressed by an extrachromosomal expression construct, for instance because a heterologous oxime dehydratase gene is to be expressed in a microorganism or because the expression of a chromosomal gene is to be supplemented by the additional expression of an extrachromosomal aldoxime dehydratase gene, the aldoxime dehydratase gene and the chaperone gene can be present on a common expression construct or on separate expression constructs.

A preferred embodiment of the process according to the invention comprises at least the following steps a), b) and d):
a) isolating a microorganism producing an enzyme with aldoxime dehydratase from a natural source or producing it by recombinant techniques,
b) multiplying said microorganism,
c) optionally isolating the enzyme with aldoxime dehydratase activity from the microorganism or preparing a protein fraction containing this enzyme, and
d) transferring the microorganism according to step b) or the enzyme according to step c) to a medium that contains an oxime of general formula (II).

In the process according to the invention, substrate, e.g. citronellal oxime, is brought into contact with the enzyme that possesses the activity of an aldoxime dehydratase in a medium and/or is incubated in such a way that reaction of the substrate takes place, e.g. of citronellal oxime to citronellal nitrile, in the presence of the enzyme. Preferably the medium is an aqueous reaction medium.

The pH of the aqueous reaction medium in which the process according to the invention is preferably carried out is advantageously maintained between pH 4 and 12, preferably between pH 4.5 and 9, especially preferably between pH 5 and 8.

The aqueous reaction media are preferably buffered solutions, which as a rule have a pH preferably from 5 to 8. The buffer used can be a citrate, phosphate, TRIS (tris(hydroxymethyl)-aminomethane) or MES (2-(N-morpholino)ethanesulfonic acid) buffer. Moreover, the reaction medium can contain further additives, e.g. detergents (for example taurodeoxycholate), FMN, ions, such as metal ions (e.g. $Fe^{2+}$ and $Sn^{2+}$) or anions such as $SO_3^{2-}$, and sodium azide. Detailed compositions of suitable reaction mixtures are also given in the following literature sources: Kato, Y. et al., Biochemistry (2000), 39, 800-809 and Xie, S.-X. et al., Biosci. Biotechnol. Biochem. (2001), 65(12), 2666-2672.

The substrate, for example citronellal oxime, is preferably used in a concentration of 2-200 mM, especially preferably 5-25 mM in the enzymatic reaction and can be supplemented continuously or discontinuously. However, the reaction can also be carried out with pure aldoxime (e.g. citronellal oxime) in the presence of only the enzyme-expressing, such as PAOx-expressing host organism (e.g. *E. coli*)—as described in example 2.

The enzymatic reaction of oxime to nitrile takes place as a rule at a reaction temperature below the deactivation temperature of the enzyme used and above −10° C. Preferably the process according to the invention is carried out at a temperature between 0° C. and 95° C., especially preferably at a temperature between 15° C. and 60° C., in particular between 20° C. and 40° C., e.g. at about 25° C. to 30° C.

A process according to the invention in which the reaction of oxime to nitrile takes place at a temperature in the range from 20 to 40° C. and/or a pH in the range from 4 to 10, preferably at pH 8, is especially preferred.

In addition to these single-phase aqueous systems, in another variant of the invention two-phase systems are also used. In addition to an aqueous phase, organic, non-water-miscible reaction media are used as second phase. As a result the reaction products accumulate in the organic phase. After the reaction, the product, e.g. citral nitrile, neral nitrile, geranial nitrile or citronellal nitrile, in the organic phase can easily be separated from the aqueous phase containing the biocatalyst.

A process according to the invention, characterized in that the production of nitriles, in particular citral nitrile, neral nitrile, geranial nitrile or citronellal nitrile, takes place in single-phase aqueous systems or in two-phase systems, is preferred.

The reaction product, e.g. citral nitrile, neral nitrile, geranial nitrile or citronellal nitrile, can be extracted with organic solvents and can optionally be distilled for purification.

Suitable organic solvents are for example aliphatic hydrocarbons, preferably with 5 to 8 carbon atoms, such as pentane, cyclopentane, hexane, cyclohexane, heptane, octane or cyclooctane, halogenated aliphatic hydrocarbons, preferably with one or two carbon atoms, such as dichloromethane, chloroform, carbon tetrachloride, dichloroethane or tetrachloroethane, aromatic hydrocarbons, such as benzene, toluene, the xylenes, chlorobenzene or dichlorobenzene, aliphatic acyclic and cyclic ethers or alcohols, preferably with 4 to 8 carbon atoms, such as ethanol, isopropanol, diethyl ether, methyl tert-butyl ether, ethyl tert-butyl ether, dipropyl ether, diisopropyl ether, dibutyl ether, tetrahydrofuran or esters such as ethyl acetate or n-butyl acetate or ketones such as methyl isobutyl ketone or dioxane or mixtures thereof. Especially preferably, the aforementioned heptane, methyl tert-butyl ether, diisopropyl ether, tetrahydrofuran, ethyl acetate are used.

The aldoxime dehydratases used according to the invention can be used in the process according to the invention as free or immobilized enzyme, as already described above.

For the process according to the invention, resting or growing, free or immobilized cells that contain nucleic acids, nucleic acid constructs or vectors coding for the aldoxime dehydratase can be used. Lysed cells, such as cell lysates or cell homogenates, can also be used. Lysed cells are for example cells that have been made permeable by a treatment for example with solvents, or cells that have been disrupted by an enzyme treatment, by a mechanical treatment (e.g. French press or ultrasound) or by some other process. The resultant raw extracts are advantageously suitable for the process according to the invention. Purified or partially purified enzymes can also be used for the process.

If free organisms or enzymes are used for the process according to the invention, these are preferably separated prior to extraction, for example by filtration or centrifugation.

The process according to the invention can be operated batchwise, semi-batchwise or continuously.

Experimental Section

If no special information is provided in the following examples, the following general information applies.

A. General Information

All materials and microorganisms used are products that are commercially available or are obtainable from stock-culture collections.

Unless stated otherwise, the cloning and expression of recombinant proteins are carried out by standard methods, as described for example in Sambrook, J., Fritsch, E. F. and Maniatis, T., Molecular Cloning: A Laboratory Manual, 2nd edition, Cold Spring Harbor Laboratory, Cold Spring Harbor Laboratory Press, Cold Spring Harbor, N.Y., 1989.

a) Bacterial Strains, Plasmids and Growing Conditions

All experiments were carried out with E. coli. E. coli TG10, a TG1 derivative without rhamnose isomerase, was used for the expression of PAOx.

b) Gas Chromatography

Measuring instrument: Agilent 6890 N
Column: Optima 5 Accent, length=30 m, I.D.=0.25 mm, O.D.=0.4 mm, film thickness 0.25 µm
  From Macherey&Nagel #725820.30
Flow: 1.0 ml/min at 13.5 PSI (at furnace temp. 80° C.)
Split: 1:50, split-flow: 50 ml/min, septum purge 3 ml/min (at furnace temp. 80° C.)
Carrier gas: helium
Injector: split/splitless with Split Liner siltec-deactivated (Restec #20713-214.5)
Injector temperature: 280° C.
Injection volume: 1 µl
Detector: FID with 300 ml/min air, 30 ml/min hydrogen and 30 ml/min make-up gas (helium)
Detector temperature: 320° C.

Temperature Program:
  Start: 60° C.
  Residence time 1: 0 min
  Temperature ramp 1: 15° C./min
  Final temperature 1: 320° C.
  Residence time 2: 5 min
  Total run time: 22.3 min
Evaluation: Empower-2-software according to areas-%

B. EXAMPLES

Example 1

Expression of PAOx in E. coli

In the present example the codon usage of the gene of phenylacetaldoxime dehydratase (PAOx) from Bacillus sp. strain OxB-1 was optimized for expression in E. coli. The new DNA sequence was synthesized and cloned into pDHE, a rhamnose-inducible expression vector. The GroEL/S-chaperones that are required for production of soluble PAOx were cloned into IPTG-inducible pAgro or pHSG vectors. Expression of PAOx took place in E. coli TG10, a TG1 derivative without rhamnose isomerase. TG10 cells that contained pAgro and pHSG (TG10+) were transformed with pDHE-PAOx and were cultivated in 2xYT for 5 h at 37° C. in the presence of ampicillin (pDHE), spectinomycin (pAgro) and chloramphenicol (pHSG). 5 mL of this culture was transferred to 500 mL of the same medium that contained 100 µM IPTG and 0.5 g/L rhamnose. Induction took place at 30° C. for a period of about 18 h. The cells were harvested by centrifugation and were used as catalysts in the transformation of citronellyl oxime to citronellyl nitrile. Optionally the cells were stored at −20° C. until use.

Example 2

Transformation of Citronellal Oxime to Citronellyl Nitrile by PAOx

Figure 2A:
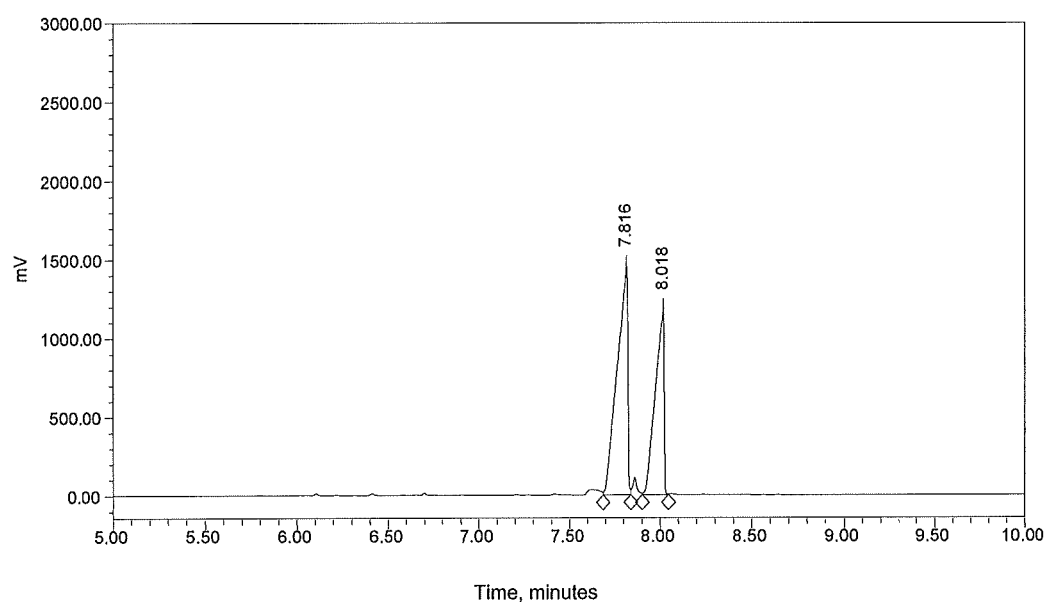
FIG. 2A: GC chromatogram of E/Z-citronellal oxime before biocatalytic reaction with PAOx (RT: 7.816 & 8.018 min).
Figure 2B:
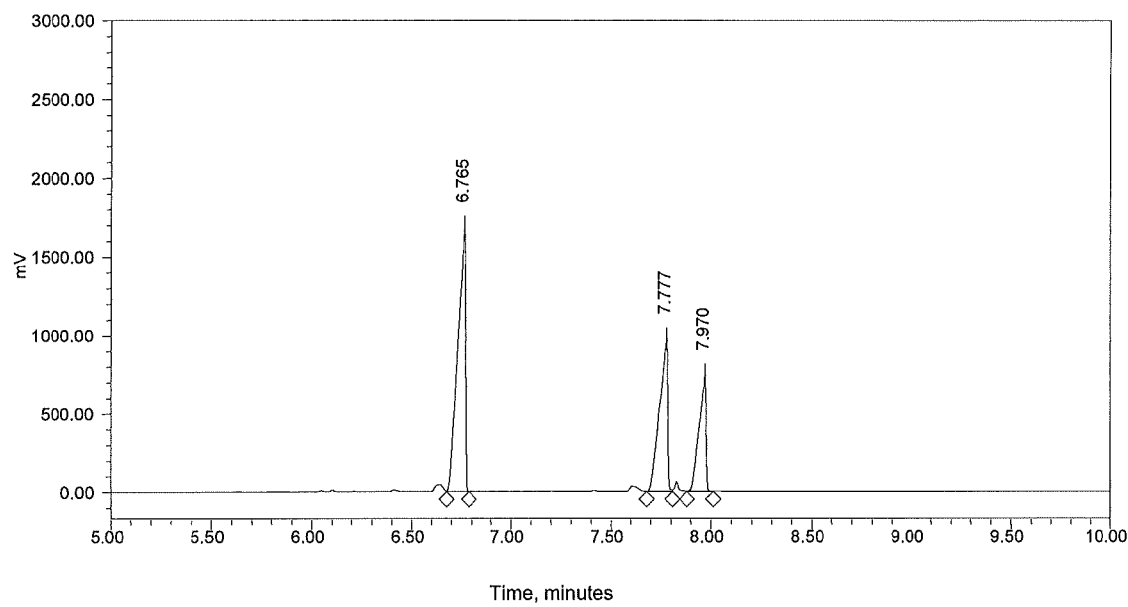
FIG. 2B: GC chromatogram of E/Z-citronellal oxime during biocatalytic reaction with PAOx (time: 18 h). Citronellyl nitrile is detectable as reaction product (RT: 6.765 min).
Figure 2C:
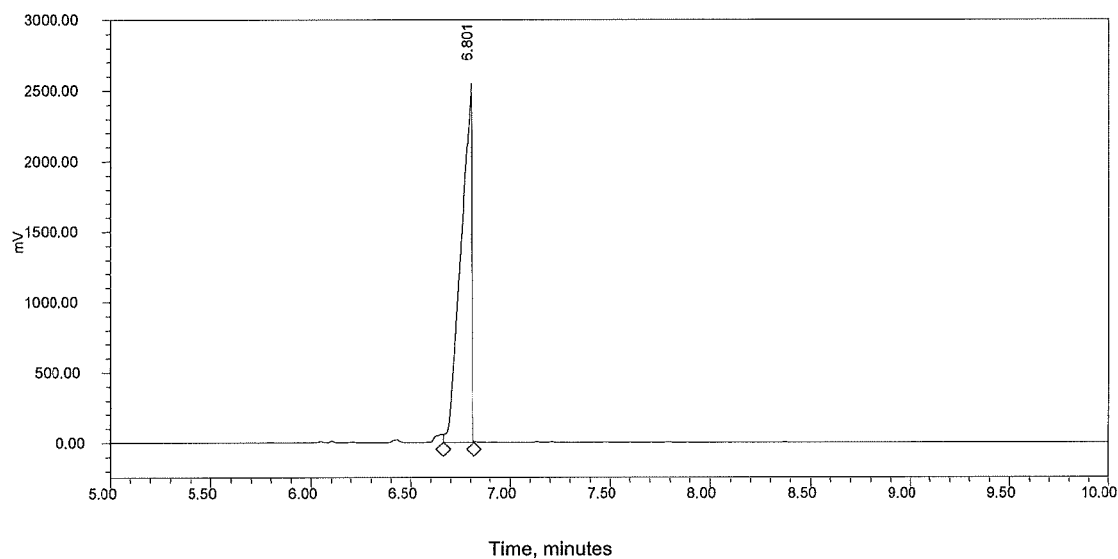
FIG. 2C: GC chromatogram of citronellyl nitrile that was formed during biocatalytic reaction with PAOx (time: 90 h). E/Z-citronellal oxime was converted to the nitrile completely.

The enzymatic transformation of citronellal oxime to the corresponding nitrile was carried out as follows: 50 mL of racemic R/S-E/Z citronellal oxime were mixed with 12.5 g E. coli TG10 that expressed phenylacetaldoxime dehydratase (PAOx). The reaction mixture was incubated at 30° C., with stirring. Samples of the reaction mixture (0.1 mL) were taken after 18 h and 90 h and were mixed with 0.5 mL of n-heptane. The organic phase was analyzed by gas chromatography (GC). The GC analysis was performed on an Agilent 6890 N (column: Optima 5 Accent, Macherey & Nagel; flow: 1 mL/min at 13.5 PSI, injection temp. 280° C.; detection temp. 320° C.; detector: FID; citronellal oxime retention time: 7.816 min & 8.018 min; citronellyl nitrile retention time: 6.765 min). After 90 h, the racemic R/S-E/Z citronellal oxime had been transformed quantitatively to the corresponding nitrile. The reaction that took place is shown in FIG. 1. The corresponding gas chromatograms before, during and after conversion are shown in FIG. 2A, FIG. 2B and FIG. 2C. A rough temporal course of the reaction, giving the percentage of the peak areas of the gas chromatograms, is shown in Table 5.

TABLE 5

| Time [h] | Citronellal oxime | Citronellal nitrile |
|---|---|---|
| 0 | 100.00 | 0.00 |
| 18 | 50.03 | 49.97 |
| 90 | 0.03 | 99.97 |

TABLE 6

Sequence data:

| SEQ ID NO | Source | Type | Remarks | |
|---|---|---|---|---|
| 1 | *Bacillus* s. OxB-1 | AA | PAOx | |
| 2 | *Bacillus* s. OxB-1 | NA | PAOx | Wild-type DNA for SEQ ID NO: 1 |
| 3 | artificial | NA | PAOx | SEQ ID NO: 1 codon-optimized for *E. coli* |
| 4 | *Arthrobacter aurescens* TC1 | AA | Aliphatic aldoxime dehydratase | |
| 5 | *Acinetobacter* sp. strain ADP1 | AA | Aliphatic aldoxime dehydratase | |
| 6 | *Acidovorax avenae* (ATCC 19860) | AA | Phenylacetaldoxime dehydratase | |
| 7 | *Actinosynnema mirum* (DSM 43827) | AA | Phenylacetaldoxime dehydratase | |
| 8 | *Bradyrhizobium* sp. BTAi1 | AA | Phenylacetaldoxime dehydratase | |
| 9 | *Burkholderia ambifaria* IOP40-10 | AA | Phenylacetaldoxime dehydratase | |
| 10 | *Burkholderia ambifaria* MC40-6 | AA | Phenylacetaldoxime dehydratase | |
| 11 | *Burkholderia cenocepacia* MC0-3 | AA | Phenylacetaldoxime dehydratase | |
| 12 | *Pantoea* sp. At-9b | AA | Phenylacetaldoxime dehydratase | |
| 13 | *Pseudomonas fluorescens* WH6 | AA | Phenylacetaldoxime dehydratase | |
| 14 | *Pseudomonas fluorescens* WH6 | AA | Phenylacetaldoxime dehydratase | |
| 15 | *Pseudomonas putida* F1 | AA | Phenylacetaldoxime dehydratase | |
| 16 | *Pseudomonas putida* strain BIRD-1 | AA | Phenylacetaldoxime dehydratase | |
| 17 | *Shewanella woodyi* ATCC 51908 | AA | Phenylacetaldoxime dehydratase | |
| 18 | *Sphingomonas wittichii* RW1 | AA | Phenylacetaldoxime dehydratase | |
| 19 | *Variovorax paradoxus* EPS | AA | Phenylacetaldoxime dehydratase | |
| 20 | *Variovorax paradoxus* S110 | AA | Phenylacetaldoxime dehydratase | |
| 21 | *Variovorax paradoxus* S110 | AA | Phenylacetaldoxime dehydratase | |
| 22 | *Xanthobacter autotrophicicus* Py2 | AA | Phenylacetaldoxime dehydratase | |
| 23 | *Gibberella zeae* | AA | Phenylacetaldoxime dehydratase | |
| 24 | *Pseudomonas chlororaphis* | AA | Aliphatic aldoxime dehydratase | |
| 25 | *Pseudomonas* sp. K-9 | AA | Aliphatic aldoxime dehydratase | |
| 26 | *Rhodococcus erythropolis* | AA | Aliphatic aldoxime dehydratase | |
| 27 | *Rhodococcus globerulus* | AA | Aliphatic aldoxime dehydratase | |
| 28 | *Arabidopsis thaliana* | AA | Indoleacetaldoxime dehydratase | |

NA: nucleic acid;
AA: amino acid

The following is a listing of usable sequences according to Table 6, which can be used directly for a process according to the invention or can be used as starting sequences, optionally also in the form of coding nucleic acid sequences that serve for the production of functional equivalents, which can then be used in a process according to the invention. The access numbers refer to specialist databases, e.g. NCBI (National Center for Biotechnology Information), GeneBank, or Swiss-Prot.

```
SEQ ID NO: 1; Access numbers: BAA90461; P82604 (UniProtKB/Swiss-Prot)
MKNMPENHNPQANAWTAEFPPEMSYVVFAQIGIQSKSLDHAAEHLGMMKKSFDLRTGP

KHVDRALHQGADGYQDSIFLAYWDEPETFKSWVADPEVQKWWSGKKIDENSPIGYWSEVTTI

PIDHFETLHSGENYDNGVSHFVPIKHTEVHEYWGAMRDRMPVSASSDLESPLGLQLPEPIVRE

SFGKRLKVTAPDNICLIRTAQNWSKCGSGERETYIGLVEPTLIKANTFLRENASETGCISSKLVY

EQTHDGEIVDKSCVIGYYLSMGHLERWTHDHPTHKAIYGTFYEMLKRHDFKTELALWHEVSVL

QSKDIELIYVNCHPSTGFLPFFEVTEIQEPLLKSPSVRIQ

SEQ ID NO: 2; Access number: AB028892 (NCBI)
ttgaaaaatatgccggaaaatcacaatccacaagcgaatgcctggactgccgaatttcctcctgaaatgagctatgtagtattt gcgcagattgggattcaaagcaagtctttggatcacgcagcggaacatttgggaatgatgaaaaagagtttcgatttgcggacaggc cccaaacatgtggatcgagccttgcatcaaggagccgatggataccaagattccatcttttttagcctactgggatgagcctgaaacattt aaatcatgggttgcggatcctgaagtacaaaagtggtggtcgggtaaaaaaatcgatgaaaatagtccaatcgggtattggagtgag gtaacgaccattccgattgatcactttgagactcttcattccggagaaaattacgataatggggtttcacactttgtaccgatcaagcatac agaagtccatgaatattgggagcaatgcgcgaccgcatgccggtgtctgccagtagtgatttggaaagcccccttggccttcaattac
```

-continued cggaacccattgtccgggagtctttcggaaaacggctaaaagtcacggcgccggataatatttgcttgattcgaaccgctcaaaattgg tctaaatgtggtagcggggaaagggaaacgtatataggactagtggaaccgaccctcataaaagcgaatacgtttcttcgtgaaaat gctagtgaaacaggctgtattagttcaaaattagtctatgaacagacccatgacggcgaaatagtagataaatcatgtgtcatcggata ttatctctccatgggcatcttgaacgctggacgcatgatcatccaacacataaagcgatctacggaaccttttatgagatgttgaaaag gcatgattttaagaccgaacttgctttatggcacgaggtttcggtgcttcaatccaaagatatcgagcttatctatgtcaactgccatccga gtactggatttcttccattctttgaagtgacagaaattcaagagcctttactgaaaagccctagcgtcaggatccagtga SEQ ID NO: 3;
atgaaaaacatgccagaaaaccacaacccgcaggctaacgcctggactgcagaattcccgccagagatgtcttacgttgtc ttcgcgcagattggcatccagtctaaaagcctggatcatgcagccgaacatctgggcatgatgaaaaatctttcgacctccgtactgg tccaaaacgttgatcgcgcactgcaccagggtgctgatggctatcaggactctatcttcctggcctactgggacgaaccagaaacc ttcaaaagctgggttgcagaccccagaagtgcagaaatggtggagcggtaaaaaaatcgatgaaaacagcccgatcggctattggtc tgaggttaccactatcccgattgaccacttcgagaccctgcactctggtgagaactatgacaacggcgtttcccacttcgtgccgatcaa acataccgaagtgcacgaatactggggtgctatgcgtgatcgtatgccggtgtctgcttcttccgatctggaaagcccgctgggtctcca gctgccagaaccgatcgtacgtgagagctttggtaaacgcctgaaagttaccgctccagacaacatctgcctgattcgtaccgcacag aactggtccaaatgtggttctggtgaacgcgaaacctacattggcctggtcgaaccgactctgatcaaagcgaacaccttcctgcgtg aaaacgcgtctgagaccggttgcattagctctaaactggtttacgagcagacccatgatggcgaaatcgtagataaatcctgtgtaatc ggctactatctgtccatgggtcatctggaacgctggactcacgaccacccaactcacaaagcgatttacggcacgttctacgaaatgct gaaacgtcacgactttaaaacggaactggcgctgtggcacgaagtaagcgttctgcagtctaaagacatcgagctgatctatgtcaa ctgccacccatccacgggttttctgccgttctttgaagtgaccgaaatccaggaaccactgctgaaatcccatccgtgcgtattcagtg a SEQ ID NO: 4, Access numbers: NCBI: YP_947647.1, GenBank: ABM07831.1
MAPDPSRQDPAIESSIPRHFTVKRTRPKRAGAGYAPPYPSYSVRFAEGVSNLVCAFLGV

QSRAPLSHEAKVASAGMWELCANEDGPMSREHAVHTDEQGFDNQVIIAYWDDVDAYGRWFK

KHRDALIGAGLEPSDYGRWIEAVTPEARGFETLYSSNTFPEGAARMATGGFTGEIQEHGYWGS

MRDRLPIAQTDALEPVGDPVVPRNPGIVRVEPHDNLAVIRSGQDWSLCDDAERASYFSHVEPQ

LKAGMDFLTTEGASIGCYANRYMTSSDGNGNVLEQSFGLSFWHSLEDMERWAESHPTHVAIF

RSAMTFLQANAGARLRLSHEVAVVSRDQQYYEYNNCHAGTGMLGARRPLGTATPGTRI

SEQ ID NO: 5; Access number: NCBI: YP_046290.1; GenBank: CAG68468.1
MESAIDKHLKCPRTLSRRIHDEYEPPFAMWVARADESLQQVVMAYFGVQFKSEQKAIAL

KAMQHIVQSFSLDNGPQNHDITHHTDNQGYENYIVVGYWRDPGAYCRWFRSTEVSHWWDSD

ERLNDGIGYFREIVIPRADQFETLYAFKEDLPGVGAVMDDISDDIQEHGYWGSARERFPISQTD

RMLANGELHIISGDPEKGGRVLVQGHDNITLIRSGQDWVNADEKERELYFNEMLPSLQAGMDF

LRDEGQALGCYSNRFVRNVDIDGNLLDIAYDIGYWRSLDKLERWAESHPTHLRIFTTFFKVVTG

LQNLRLYHEVSVSDAKNQVFEYINCHPQTGMMRDAQMT

SEQ ID NO: 6; Access number: F0QD95_ACIAP (UniProtKB/TrEMBL)
MESAIPPRLQCPRSLSRRVADDYQPPFPMWVARPQADLQQVVMAYFGIQYQGEAQKPR

ALAVLREWVAAFGAPDGPLRHDLTHHIDAQGYDNLIAVGYWRDPEAHRRWMQAPAQAGWW

NAPERLQEGLGYFREVSAPRAEQFETLYAFQDALPGVGGVMESTSGDIQEHGYWGSMRDRF

PASQVDRMQARGTLLIAEGDPAHGGRVVVRGHDNIALIRSGQDWMEAEAEERRLYLEDIEPTL

HAGMDFLRDQGAAVGCYSNRYVHNIDLDGRRLDQSYNIGHWRSVDLLERWAESHPTHLRIFG

TFFKVAAGLSKLRLYHEVSVSDAASQHFEYIQCHPATGMMRDARLQAPA

SEQ ID NO: 7, Access number: YP_003097901.1 (NCBI)
MSSLPLDDRATAHRPEGYDPRGGPGHEVRWSDDVTHLVVARFGVQTDDSAAGVKAIAR

VLELAAGESGPALVERVSDDDSEMAVCYWPDPEAHRAWWASGPVRDWWASLPVDGPIGHW

HETSVTPVEQFETLYSAEFAAGPSRFAGTGPTNLHDYDNSTLDRMPATAHRDLRQERAEEPTT

DLPPGESPRGRRVRLAEPSPSGLCWIRTAQEWSIAPDDQLASYRDGVEPAYRTAIAHLQDNPH

DTGCLSARLVGNLDANGARAAGAEAVVWWRGIGDLLRWAHDHKTHQDILNGFWEHVIAKFGP

GTRVRLWHEVHVLPEGALTAEYVNCHPGTGLLQTWPG

SEQ ID NO: 8, Access number: YP_001240697 (NCBI)
MESAIPPHLITTRCRHRRVDDDYKPPYPSFVARHGADVSRVVMAYFGVQYRAETPAAAS

TADFMVLVSRADGPSHWDLAHYVDQAGFANDVFVAYWDDVVRFDSWFEPARAAWTGPGAE

GGGRFIEVLRPAVERYETLFSSLGRPEGIAVIAEGMSGEVLEHAYWGGMRDRIPLSQTSEMRS

LGKPTLVQDGPRLRVIAQDNLCMIRSGQDWSDTDAAERRMYLDDVEPVLREGMDFLRDQGLS

IGCYANRYMRLRGADGALTEKSYGQSWWQSLSALERWAESHPTHVRIFGAAMKYLSSLGPAA

RLRLYHEVTVAAADEQFFEYRGCHAKTGMLAAAG

SEQ ID NO: 9, Access number: ZP_02891657 (NCBI)
MESAIDKHLVCPRTLSRRVADDYQPPFPMYVARASEDLSQVVMGYFGVQYRGADQRSA

ALAALRRIVADFDAPDGPGNHDLTQHTDNQGYDNLIAVGYWRDPDAYARWIASPAVAEWWTS

DARLADGIGYFREIVAPRAEQFETLYAFTADFPGVGAIMDGVSGEIEEHGYWGSMRDRFPISQT

DWMHADGELRIVAGDPARGGRVVVLAHDNIALIRSGQDWRAAQDDERRLYLDEIEPTLRSGM

EFLRDNGVDVGCYSNRYVRSIDLDGNLLDESYNIGHWRSLDRLERWAESHPTHLRIFVTFFRV

VTGLSKLRLYHEVSVFDAKHQVYEYVNCHPNTGMMRDAVAR

SEQ ID NO: 10; Access numbers: ACB68693 (GenBank), YP_001816246 (NCBI)
MESAIDKHLVCPRTLSRRVADDYQPPFPMYVARAAEDLSQVVMGYFGVQYRGADKRSV

ALAALRRIVADFDAPDGPGNHDLTQHTDNQGYDNLIAVGYWRDPDAYARWIASPAVAEWWAS

DARLADGIGYFREIVAPRAEQFETLYAFTNDFPGVGSIMDGVSGEIEEHGYWGSMRDRFPISQT

DWMHADGELRIVAGDPARGGRVVVLAHDNIALIRSGQDWRAAEDDERRLYLDEIEPTLRSGME

FLRDNGVDVGCYSNRYVRSIDLDGNLLDESYNIGHWRSLDRLERWAESHPTHLRIFVTFFRVV

TGLSKLRLYHEVSVFDAKHQVYEYVNCHPTTGMMRDAAAR

SEQ ID NO: 11, Access number: YP_001776877 (NCBI)
MESAIDKHLICPRTLSRRVADDYQPPFPMYVARAAEDLSQVVMGYFGVQYSGADKRAAA

MAALRRIVADFGGQDGPNNFDLTQHTDDEGYENLIAVGYWRDPAAYARWIASPALVEWWASD

ARLADGIGYFREIVAPRAEQFETLYAFTSDFPGVGAIMDGVSGEIEEHGYWGSMRDRFPISQTD

WMNANGELRIVDGDPARGGRVVVLAHDNIALIRSGQDWRAAESDERRLYLEEIEPTLRSGMEF

LRDNGKDVGCYSNRYVRSIDLDGNVLDESYNIGHWRSLDRLERWAESHPTHLRIFVTFFRVVT

GLSKLRLYHEVSVFDAKHQVYEYVNCHPRTGLMRDAVAIAR

SEQ ID NO: 12, Access number: YP_004119277 (NCBI)
MESAIDTHLKCPRTLSRRVHDDYQPPFPMFAGRADASLTQVVMAYLGVQFREEQRAAAI

TAMQHIVRSFSLDNGPGNHDVTFHTDNQGFGNFIVVGYWRDPAAYCRWLHQPAITGWWSSD

DRLRDGLGYFREIIAPRAEQFETLYAFKEALPGVGAVMDNLSGEIQEHGYWGSVRDRIPASQT

DWLQPDGELRIISGDPAAGGRVVVQGHDNITLIRSGQDWMDADEQERALYFTEMLPPLQAGM

DFLRDEGQTLGCYSNRFVRNVDIDGNVLDIAYDIGFWRSLDRLERWAESHPTHLRIFTTFFRVV

AGLQKLRLYHEVSVSDARFQTFEYINCHPQTGMLRDAVR

SEQ ID NO: 13, Access number: ZP_07774756 (NCBI)
MKPTTELQVVAGDPAKGGRVVVMGHDNLTLIRSGQDWADAEADERSLYLDEILPTLQDG

MDFLRDNGQPLGCYSNRFVRNIDLDGNFLDVSYNIGHWRSVEKLERWAESHPTHLRIFVTFFR

VAAGLKKLRLYHEVSVSDAKSQLFEYINCHPHTGMLRDAQAATA

SEQ ID NO: 14:, Access number: ZP_07774757 (NCBI)
MESAIDTHLKCPRTLSRRVPDEYQPPFPMWVARADEQLEQVVMAYLGVQYRGEAQREA

ALQAMRHIVGSFSLADGPQTHDLTHHTDSSGFDNLIVVGYWKDPGAHCRWLRSAPVNDWWA

SQDRLSDGLGYFREISAPRAEQFETLYAFQDNLPGVGAVMDATSGEIENTVTGARCATASPSP

RQTG

SEQ ID NO: 15; Access number: YP_001268042 (NCBI)
MESAIDKHLVCPRTLSRRVPDDYQPPFPMWVGRADEQLTQVVMAYLGVQYRGDGQRE

RALQAMREILGSFSLTDGPLTHDLTHHTDSSGYDNLMIVGYWKDAGAYCRWLRSPEVDGWW

SSPQRLNDGLGYYREITAPRAEQFETLYAFQNDLPGVGAIMDNTSGEIEEHGYWGSMRDRFPV

SQTDWMNPNGELRVVAGDPAKGGRVVVLGHDNIALIRSGQDWATAEAAERSLYLDEILPTLQD

GMDFLRDNGQPLGCYSNRFVRNIDADGNLLDMSYNIGHWRSLEKLERWAESHPTHLRIFVTFF

RVAAGLEKLRLYHEVSVSDASSQVFEYINCHPHTGMLRDAKVSSN

SEQ ID NO. 16, Access number: E4RFH2_PSEPB (UniProtKB/TrEMBL)
MESAIDKHLMCPRTLSRRVPDDYQPPFPMWVGRADEQLTQVVMAYLGVQYRGDSQRE

RALQAMREILGSFSLSDGPLTHDLTHHTDSSGYDNLMIVGYWKDTGAYCRWSRSPEVDGWW

SSPQRLNDGLGYYREITAPRAEQFETLYAFQSDLPGVGAIMDNTSGEIEEHGYWGSMRDRFPV

SQTDWMNPNGELRVVAGDPAKGGRVVVIGHDNIALIRSGQDWAAAEAAERSLYLDEILPTLQD

GMDFLRDNGQPLGCYSNRFVRNIDADGNVLDMSYNIGHWRSLEKLERWAESHPTHLRIFVTFF

RVAAGLEKLRLYHEVSVSDASSQVFEYINCHPHTGMLRDAKVSSN

SEQ ID NO: 17, Access number: YP_001758607 (NCBI)
MMNNMPKNWTPPAPAWTSLWKTDEENLVCGLFAIQGQHSAPLDDWAKKAFTGEFSPK

LLEQGMFTDKAGITNYLYIAYWFASDYKTWWQQSAANSWWASPLLDEGDISVWREVFTMPHQ

RFETLHSSENAHGAARLSPSLEGPMMEHGYSGAARDRIPCSSSQDIKNDNSIWEHLQVNVENK

SNRIKLSPPKNMCVIRSGQDWTHCEEDEKEYYLTNVHTVLKKGMDYLSNNPVKTHCASMRFIT

KTDGNWCSVEQTFGLGYGNDIYAFENWAKSHPTHIAIFDRFMGMVEKYNVDLKLQLWHEVTLI

PEQDCEFEYINCHGQTGLLCYINI

SEQ ID NO: 18, Access number: YP_001261493 (NCBI)
MDSSITPHLACPRSRPRRIADDYAPPYPAWSARIDPAIGQVVMASYGVQGRESGDVAAA

LAHVRALRATLDADVRHVDLARYVDEAGYDTLVLQPYWTDPEAFRRWEARADVAALLAAETGL

GHFREILTPTVERLETLYSTEDEMEGLGRALERRSPPVQEHAYWGSARDRFPIAQTDALEPAG

QLGFAADGAGRVTVRGHDNIAIIRSGQDWGPTGGEERRLYLAEIEPVLRAGMDFLRDRGGEC

GCYLNRYMRIVDMDGAPQEKSFGWSYWRSLGDMENWSEAHPSHLAIFGTFMRIVQQLNFDLK

LRLWHEVYVVTPDQQLYDYRNCHPDTGFLKQMPR

SEQ ID NO: 19, Access number: YP_004155682 (NCIB)
MESAIAEHLKCPRTHRRVEDDYTPPYPVWSARAPTSVTQVTMGYFGVQSRGPEMQG

RACAALMKIARDFALPDGPGHHDLAHYVDADGFDNMVAIAYWHDAAAFARWSATPAIDAWWR

SDERLNEGLGYFREIASPRVEHFETMFNTPDRFEGIGVVMGELSGELQEHGYWGSMRDRIPLS

QTDALSPSGTRAVVAGTPAPGQRVRIAGHENIAMIRSGQEWADTTGQERTLYLEDMEPVLREG

MDFLRDQGLGIGCYSNRYMHHLDAKGAPLQKSFGLSYWRSLADMERWAESHPTHVAIFGSFM

RYVQALNFQLQLRVYHEVSVLKADEQSYEYINCRARSGLMNGLAVT

SEQ ID NO: 20, Access number YP_002942593 (NCBI)
MESRDADARALLARVANTFAGVGGPASLGRGVATGAGGERSDIFYAYWNSSAEYASWL

TTPRVASLWTDDALLRGPIGLWRESMIIPVERNETNYSNDAAYDGIAQIDKEMRKTDVHGYWG

SARERIPASAHDTMPSAAPDFMGRPAASMETLGRRFRITLPGNTCVIRSFQDWSQAQAAEVD

WYLGNVEPVLRVGLDYLNGNRTEAKCYGMRYIREYDISGAIDLNRTSTFGYFESLQTLERWTH

THPTHLDIFRAAISMVQRFQGEVAVKLGHEVSVLPEGMLSAEYVNCARSTGFLPWFHED

SEQ ID NO: 21, Access number: YP_002944432
MESAIAEHLKCPRTRHRRVEDDYAPPYPAWSARAPGAVRQVVMGYFGVQSRGAGMQG

RACAALMKIAAGFALPDGPGHHDFAHHVDAAGCDNMVAIAYWNDPAAHARWCTAPEVDAWW

RSDERLADGLGYFREIVAPRAEHFETMFNTPDRLEGVGVVMGGVSGELQEHGYWGSMRDRIP

LSQTDAMAPSGTRAVIAGAPAPGQRVRIAGHENIAMIRSGQEWADTTGQERALYLGEMEPVLR

EGMDFLRDQGLHIGCYSNRYMQHLDAKGAPLEKSFGLSFWHSLADMERWAESHPTHVAIFGS

FMRYVQALNFQLQLRVYHEVSVLKADEQSYEYINCHAGSGLMNGLGEV

SEQ ID NO: 22, Access number: YP_001416464
MVFHVEYPRIVPERRPPGHEPAAPRFSLRWEQPVGLVVCAYFGLQGQDLAWDEQKAFF

DRLQTSFGTDGPVAHEIMRMHDETGAVNAILVAYWLDATAHARWERNSPFMAWFRDPARLEG

TRGVWRETMHVPYDRHETIYSTPSYVIGLARTPGATRVPITTNGYFGAMRDRMPVSAIDTLESP

LGAMPPRRAPDSHGRRLTAAFPLNLISIRSGQYWEGAGNEQTADYIDNLQPKLMRGMAHLSSH

PEQTGTLTLRIMTNLDAEGRPRAETSVHGYFLSMAHLEEWSRSHETHLDIYRHAIAMNRLYKEK

REVFTWHEVFALLPGAHAEYANCHGGTGLLPYFADA

SEQ ID NO: 23; Access number: Q2WG72 (NCBI, SwissProt)
MLRSRFPASHHFTVSVFGCQYHSEAPSVEKTELIGRFDKLIDSAAIHVEHLEQNDVPSKI

WMSYWESPQKFKQWWEKDDTASFWASLPDDAGFWRETFSLPATRAMYEGTGKDAYGFGH

CGSLIPLTTKTGYWGAYRSRMTPDFEGDTFSSPIPTYADQSVPADKIRPGRVRITDFPDNLCMV

VEGQHYADMGEREREYWNENFDGLTKQWVTNVVTAGHEQGMVIARACHGFAGEKKLGATN

GPVNGIFPGLDYVHQAQILIWQDISKMEHIGRYDQTHVKLRRDFMKAYGPGGEMEGGDLLLWV

DLGILKKDEIDAEYVGCYESTGFLKLDKGQFFKVESTAGSKLPSFFDEPIESKPIEW

SEQ ID NO: 24, Access number: Q7WSJ4 (NCBI, SwissProt)
MESAIDTHLKCPRTLSRRVPEEYQPPFPMWVARADEQLQQVVMGYLGVQYRGEAQRE

AALQAMRHIVSSFSLPDGPQTHDLTHHTDSSGFDNLMVVGYWKDPAAHCRWLRSAEVNDWW

TSQDRLGEGLGYFREISAPRAEQFETLYAFQDNLPGVGAVMDSTSGEIEEHGYWGSMRDRFPI

SQTDWMKPTNELQVVAGDPAKGGRVVIMGHDNIALIRSGQDWADAEAEERSLYLDEILPTLQD

GMDFLRDNGQPLGCYSNRFVRNIDLDGNFLDVSYNIGHWRSLEKLERWAESHPTHLRIFVTFF

RVAAGLKKLRLYHEVSVSDAKSQVFEYINCHPHTGMLRDAVVAPT

SEQ ID NO: 25, Access number: Q4W7T3 (NCBI, SwissProt)
MESAIDTHLKCPRTLSRRVPDEYQPPFAMWMARADEHLEQVVMAYFGVQYRGEAQRA

AALQAMRHIVESFSLADGPQTHDLTHHTDNSGFDNLIVVGYWKDPAAHCRWLRSAPVNAWWA

SEDRLNDGLGYFREISAPRAEQFETLYAFQDNLPGVGAVMDRISGEIEEHGYWGSMRDRFPIS

QTDWMKPTSELQVIAGDPAKGGRVVVLGHGNLTLIRSGQDWADAEAEERSLYLDEILPTLQDG

MDFLRDNGQPLGCYSNRFVRNIDLDGNFLDVSYNIGHWRSVEKLERWTESHPTHLRIFVTFFR

VAAGLKKLRLYHEVSVSDAKSQIFGYINCHPQTGMLRDAQVSPA

-continued

SEQ ID NO: 26, Access number: Q76K71 (NCBI, SwissProt)
MESAIGEHLQCPRTLTRRVPDTYTPPFPMWVGRADDALQQVVMGYLGVQFRDEDQRP

AALQAMRDIVAGFDLPDGPAHHDLTHHIDNQGYENLIVVGYWKDVSSQHRWSTSTPIASWWE

SEDRLSDGLGFFREIVAPRAEQFETLYAFQEDLPGVGAVMDGISGEINEHGYWGSMRERFPIS

QTDWMQASGELRVIAGDPAVGGRVVVRGHDNIALIRSGQDWADAEADERSLYLDEILPTLQSG

MDFLRDNGPAVGCYSNRFVRNIDIDGNFLDLSYNIGHWASLDQLERWSESHPTHLRIFTTFFRV

AAGLSKLRLYHEVSVFDAADQLYEYINCHPGTGMLRDAVTIAEH

SEQ ID NO: 27, Access number: Q76EV4 (NCBI, SwissProt)
MESAIGEHLQCPRTLTRRVPDTYTPPFPMWVGRADDTLHQVVMGYLGVQFRGEDQRP

AALRAMRDIVAGFDLPDGPAHHDLTHHIDNQGYENLIVVGYWKDVSSQHRWSTSPPVSSWWE

SEDRLSDGLGFFREIVAPRAEQFETLYAFQDDLPGVGAVMDGVSGEINEHGYWGSMRERFPIS

QTDWMQASGELRVVAGDPAVGGRVVVRGHDNIALIRSGQDWADAEADERSLYLDEILPTLQS

GMDFLRDNGPAVGCYSNRFVRNIDIDGNFLDLSYNIGHWASLDQLERWSESHPTHLRIFTTFFR

VAEGLSKLRLYHEVSVFDAADQLYEYINCHPGTGMLRDAVITAEH

SEQ ID NO: 28, Access number: O49342 (NCBI, SwissProt)
MEMILSISLCLTTLITLLLLRRFLKRTATKVNLPPSPWRLPVIGNLHQLSLHPHRSLRSLSLR

YGPLMLLHFGRVPILVVSSGEAAQEVLKTHDHKFANRPRSKAVHGLMNGGRDVVFAPYGEYW

RQMKSVCILNLLTNKMVESFEKVREDEVNAMIEKLEKASSSSSSENLSELFITLPSDVTSRVALG

RKHSEDETARDLKKRVRQIMELLGEFPIGEYVPILAWIDGIRGFNNKIKEVSRGFSDLMDKVVQE

HLEASNDKADFVDILLSIEKDKNSGFQVQRNDIKFMILDMFIGGTSTTSTLLEWTMTELIRSPKSM

KKLQDEIRSTIRPHGSYIKEKEVENMKYLKAVIKEVLRLHPSLPMILPRLLSEDVKVKGYNIAAGT

EVIINAWAIQRDTAIWGPDAEEFKPERHLDSGLDYHGKNLNYIPFGSGRRICPGINLALGLAEVT

VANLVGRFDWRVEAGPNGDQPDLTEAIGIDVCRKFPLIAFPSSVV

The disclosure of the publications mentioned herein is expressly referred to.

---

The invention claimed is:

1. A biocatalytic process for producing a nitrile of formula I

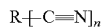 (I)

wherein

R is an unsaturated aliphatic hydrocarbon moiety with 8 to 19 carbon atoms; and n is 1;

the process comprising converting an oxime of general formula II

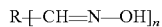 (II)

in which R and n have the meanings given above, wherein the compound of formula II is in stereoisomerically pure form or as a mixture of stereoisomers, to the nitrile of formula I in the presence of a phenylacetaldoxime dehydratase (PAOx) (EC 4.99.1.7) to a compound of formula I, wherein the compound of formula I is in stereoisomerically pure form or as a mixture of stereoisomers.

2. The process according to claim 1, wherein the PAOx is an enzyme from *Rhodococcus* sp., *Gibberella zeae* or *Bacillus* sp.

3. The process according to claim 1, wherein the PAOx has an amino acid sequence according to SEQ ID NO: 1 or an amino acid sequence at least 60% identical to SEQ ID NO. 1.

4. The process according to claim 1, wherein the oxime of formula II comprises 10 carbon atoms.

5. The process according to claim 1, wherein the compound of formula II is selected from the group consisting of citral oxime, neral oxime, geranial oxime, citronellal oxime and a partially or fully hydrogenated oxime compound thereof.

6. The process according to claim 5, wherein the compound of formula II is citronellal oxime of formula IIa

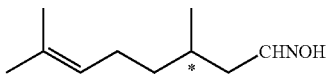 (IIa)

and the compound of formula I is citronellyl nitrile of formula Ia.

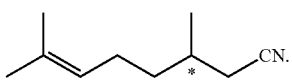 (Ia)

7. The process according to claim 1, wherein PAOx is secreted by or in a recombinant microorganism expressing functional PAOx.

8. The process according to claim 1, wherein the microorganism is free or immobilized.

9. The process according to claim 7, wherein the recombinant microorganism is a bacteria.

10. The process according to claim 7, wherein the microorganism additionally expresses at least one chaperone supporting the functional expression of the PAOx.

11. The process according to claim 10, wherein the chaperone is selected from the group consisting of GroEL and GroES.

12. The process according to claim 1, wherein the process is carried out in neat substrate as reaction medium.

13. The process according to claim 1, wherein R is singly or multiply branched.

14. The process according to claim 1, wherein R is singly or multiply substituted.

15. The process according to claim 1, wherein R is singly or multiply unsaturated.

16. The process according to claim 1, wherein PAOx is purified.

17. The process according to claim 1, wherein PAOx is in a cell lysate.

* * * * *

SEQUENCE LISTING

<160> NUMBER OF SEQ ID NOS: 28

<210> SEQ ID NO 1
<211> LENGTH: 351
<212> TYPE: PRT
<213> ORGANISM: Bacillus sp. OxB-1

<400> SEQUENCE: 1

Met Lys Asn Met Pro Glu Asn His Asn Pro Gln Ala Asn Ala Trp Thr
1               5                   10                  15

Ala Glu Phe Pro Pro Glu Met Ser Tyr Val Val Phe Ala Gln Ile Gly
            20                  25                  30

Ile Gln Ser Lys Ser Leu Asp His Ala Ala Glu His Leu Gly Met Met
        35                  40                  45

Lys Lys Ser Phe Asp Leu Arg Thr Gly Pro Lys His Val Asp Arg Ala
    50                  55                  60

Leu His Gln Gly Ala Asp Gly Tyr Gln Asp Ser Ile Phe Leu Ala Tyr
65                  70                  75                  80

Trp Asp Glu Pro Glu Thr Phe Lys Ser Trp Val Ala Asp Pro Glu Val
                85                  90                  95

Gln Lys Trp Trp Ser Gly Lys Lys Ile Asp Glu Asn Ser Pro Ile Gly
            100                 105                 110

Tyr Trp Ser Glu Val Thr Thr Ile Pro Ile Asp His Phe Glu Thr Leu
        115                 120                 125

His Ser Gly Glu Asn Tyr Asp Asn Gly Val Ser His Phe Val Pro Ile
    130                 135                 140

Lys His Thr Glu Val His Glu Tyr Trp Gly Ala Met Arg Asp Arg Met
145                 150                 155                 160

Pro Val Ser Ala Ser Asp Leu Glu Ser Pro Leu Gly Leu Gln Leu
                165                 170                 175

Pro Glu Pro Ile Val Arg Glu Ser Phe Gly Lys Arg Leu Lys Val Thr
            180                 185                 190

Ala Pro Asp Asn Ile Cys Leu Ile Arg Thr Ala Gln Asn Trp Ser Lys
        195                 200                 205

Cys Gly Ser Gly Glu Arg Glu Thr Tyr Ile Gly Leu Val Glu Pro Thr
    210                 215                 220

Leu Ile Lys Ala Asn Thr Phe Leu Arg Glu Asn Ala Ser Glu Thr Gly
225                 230                 235                 240

Cys Ile Ser Ser Lys Leu Val Tyr Glu Gln Thr His Asp Gly Glu Ile
                245                 250                 255

Val Asp Lys Ser Cys Val Ile Gly Tyr Tyr Leu Ser Met Gly His Leu
            260                 265                 270

Glu Arg Trp Thr His Asp His Pro Thr His Lys Ala Ile Tyr Gly Thr
        275                 280                 285

Phe Tyr Glu Met Leu Lys Arg His Asp Phe Lys Thr Glu Leu Ala Leu
    290                 295                 300

Trp His Glu Val Ser Val Leu Gln Ser Lys Asp Ile Glu Leu Ile Tyr
305                 310                 315                 320

Val Asn Cys His Pro Ser Thr Gly Phe Leu Pro Phe Phe Glu Val Thr
                325                 330                 335

Glu Ile Gln Glu Pro Leu Leu Lys Ser Pro Ser Val Arg Ile Gln
            340                 345                 350

<210> SEQ ID NO 2
<211> LENGTH: 1056
<212> TYPE: DNA
<213> ORGANISM: Bacillus sp. OxB-1

<400> SEQUENCE: 2
ttgaaaaata tgccggaaaa tcacaatcca caagcgaatg cctggactgc cgaatttcct      60
cctgaaatga gctatgtagt atttgcgcag attgggattc aaagcaagtc tttggatcac     120
gcagcggaac atttgggaat gatgaaaaag agtttcgatt gcggacaggg ccccaaacat     180
gtggatcgag ccttgcatca aggagccgat ggataccaag attccatctt tttagcctac     240
tgggatgagc ctgaaacatt taaatcatgg gttgcggatc ctgaagtaca aaagtggtgg     300
tcgggtaaaa aaatcgatga aaatagtcca atcgggtatt ggagtgaggt aacgaccatt     360
ccgattgatc actttgagac tcttcattcc ggagaaaatt acgataatgg ggtttcacac     420
tttgtaccga tcaagcatac agaagtccat gaatattggg gagcaatgcg cgaccgcatg     480
ccggtgtctg ccagtagtga tttggaaagc ccccttggcc ttcaattacc ggaacccatt     540
gtccgggagt ctttcggaaa acggctaaaa gtcacggcgc cggataatat ttgcttgatt     600
cgaaccgctc aaaattggtc taatgtggt agcggggaaa gggaaacgta tataggacta     660
gtggaaccga ccctcataaa agcgaatacg tttcttcgtg aaaatgctag tgaaacaggc     720
tgtattagtt caaaattagt ctatgaacag acccatgacg gcgaaatagt agataaatca     780

```
tgtgtcatcg gatattatct ctccatgggg catcttgaac gctggacgca tgatcatcca      840
acacataaag cgatctacgg aacctttat gagatgttga aaaggcatga ttttaagacc       900
gaacttgctt tatggcacga ggtttcggtg cttcaatcca agatatcga gcttatctat      960
gtcaactgcc atccgagtac tggatttctt ccattctttg aagtgacaga aattcaagag    1020
cctttactga aaagccctag cgtcaggatc cagtga                              1056
```

<210> SEQ ID NO 3
<211> LENGTH: 1056
<212> TYPE: DNA
<213> ORGANISM: artificial
<220> FEATURE:
<223> OTHER INFORMATION: DNA sequence coding for seq ID NO:1,
    codon-optimized for E.coli

<400> SEQUENCE: 3

```
atgaaaaaca tgccagaaaa ccacaacccg caggctaacg cctggactgc agaattcccg       60
ccagagatgt cttacgttgt cttcgcgcag attggcatcc agtctaaaag cctggatcat      120
gcagccgaac atctgggcat gatgaaaaaa tctttcgacc tccgtactgg tccaaaacac      180
gttgatcgcg cactgcacca gggtgctgat ggctatcagg actctatctt cctggcctac      240
tgggacgaac agaaaccttt caaaagctgg gttgcagacc cagaagtgca gaatggtgg       300
agcggtaaaa aaatcgatga aaacagcccg atcggctatt ggtctgaggt taccactatc      360
ccgattgacc acttcgagac cctgcactct ggtgagaact atgacaacgg cgtttcccac      420
ttcgtgccga tcaaacatac cgaagtgcac gaatactggg gtgctatgcg tgatcgtatg      480
ccggtgtctg cttcttccga tctggaaagc ccgctgggtc tccagctgcc agaaccgatc      540
gtacgtgaga gctttggtaa cgcctgaaa gttaccgctc agacaacat ctgcctgatt        600
cgtaccgcac agaactggtc caaatgtggt tctggtgaac gcgaaaccta cattggcctg      660
gtcgaaccga ctctgatcaa agcgaacacc ttcctgcgtg aaaacgcgtc tgagaccggt      720
tgcattagct ctaaactggt ttacgagcag accatgatg gcgaaatcgt agataaatcc       780
tgtgtaatcg gctactatct gtccatgggt catctggaac gctggactca cgaccaccca      840
actcacaaag cgatttacgg cacgttctac gaaatgctga acgtcacga cttaaaaacg      900
gaactggcgc tgtggcacga gtaagcgtt ctgcagtcta agacatcga gctgatctat       960
gtcaactgcc acccatccac gggttttctg ccgttcttg aagtgaccga atccaggaa      1020
ccactgctga atcccccatc cgtgcgtatt cagtga                             1056
```

<210> SEQ ID NO 4
<211> LENGTH: 366
<212> TYPE: PRT
<213> ORGANISM: Arthrobacter aurescens

<400> SEQUENCE: 4

Met Ala Pro Asp Pro Ser Arg Gln Asp Pro Ala Ile Glu Ser Ser Ile
1               5                   10                  15

Pro Arg His Phe Thr Val Lys Arg Thr Arg Pro Lys Arg Ala Gly Ala
            20                  25                  30

Gly Tyr Ala Pro Pro Tyr Pro Ser Tyr Ser Val Arg Phe Ala Glu Gly
        35                  40                  45

Val Ser Asn Leu Val Cys Ala Phe Leu Gly Val Gln Ser Arg Ala Pro
    50                  55                  60

Leu Ser His Glu Ala Lys Val Ala Ser Ala Gly Met Trp Glu Leu Cys
 65                  70                  75                  80

Ala Asn Glu Asp Gly Pro Met Ser Arg Glu His Ala Val His Thr Asp
                 85                  90                  95

Glu Gln Gly Phe Asp Asn Gln Val Ile Ile Ala Tyr Trp Asp Asp Val
            100                 105                 110

Asp Ala Tyr Gly Arg Trp Phe Lys Lys His Arg Asp Ala Leu Ile Gly
        115                 120                 125

Ala Gly Leu Glu Pro Ser Asp Tyr Gly Arg Trp Ile Glu Ala Val Thr
    130                 135                 140

Pro Glu Ala Arg Gly Phe Glu Thr Leu Tyr Ser Ser Asn Thr Phe Pro
145                 150                 155                 160

Glu Gly Ala Ala Arg Met Ala Thr Gly Gly Phe Thr Gly Glu Ile Gln
                165                 170                 175

Glu His Gly Tyr Trp Gly Ser Met Arg Asp Arg Leu Pro Ile Ala Gln
            180                 185                 190

Thr Asp Ala Leu Glu Pro Val Gly Asp Pro Val Val Pro Arg Asn Pro
        195                 200                 205

Gly Ile Val Arg Val Glu Pro His Asp Asn Leu Ala Val Ile Arg Ser
    210                 215                 220

Gly Gln Asp Trp Ser Leu Cys Asp Asp Ala Glu Arg Ala Ser Tyr Phe
225                 230                 235                 240

Ser His Val Glu Pro Gln Leu Lys Ala Gly Met Asp Phe Leu Thr Thr
                245                 250                 255

Glu Gly Ala Ser Ile Gly Cys Tyr Ala Asn Arg Tyr Met Thr Ser Ser
            260                 265                 270

Asp Gly Asn Gly Asn Val Leu Glu Gln Ser Phe Gly Leu Ser Phe Trp
        275                 280                 285

His Ser Leu Glu Asp Met Glu Arg Trp Ala Glu Ser His Pro Thr His
    290                 295                 300

Val Ala Ile Phe Arg Ser Ala Met Thr Phe Leu Gln Ala Asn Ala Gly
305                 310                 315                 320

Ala Arg Leu Arg Leu Ser His Glu Val Ala Val Val Ser Arg Asp Gln
                325                 330                 335

Gln Tyr Tyr Glu Tyr Asn Asn Cys His Ala Gly Thr Gly Met Leu Gly
            340                 345                 350

Ala Arg Arg Pro Leu Gly Thr Ala Thr Pro Gly Thr Arg Ile
        355                 360                 365

<210> SEQ ID NO 5
<211> LENGTH: 352
<212> TYPE: PRT
<213> ORGANISM: Acinetobacter sp. Stamm ADP1

<400> SEQUENCE: 5

Met Glu Ser Ala Ile Asp Lys His Leu Lys Cys Pro Arg Thr Leu Ser
1               5                   10                  15

Arg Arg Ile His Asp Glu Tyr Glu Pro Pro Phe Ala Met Trp Val Ala
            20                  25                  30

Arg Ala Asp Glu Ser Leu Gln Gln Val Val Met Ala Tyr Phe Gly Val
        35                  40                  45

Gln Phe Lys Ser Glu Gln Lys Ala Ile Ala Leu Lys Ala Met Gln His
    50                  55                  60

Ile Val Gln Ser Phe Ser Leu Asp Asn Gly Pro Gln Asn His Asp Ile
65                  70                  75                  80

Thr His His Thr Asp Asn Gln Gly Tyr Glu Asn Tyr Ile Val Val Gly
            85                  90                  95

Tyr Trp Arg Asp Pro Gly Ala Tyr Cys Arg Trp Phe Arg Ser Thr Glu
            100                 105                 110

Val Ser His Trp Trp Asp Ser Asp Glu Arg Leu Asn Asp Gly Ile Gly
            115                 120                 125

Tyr Phe Arg Glu Ile Val Ile Pro Arg Ala Asp Gln Phe Glu Thr Leu
            130                 135                 140

Tyr Ala Phe Lys Glu Asp Leu Pro Gly Val Gly Ala Val Met Asp Asp
145                 150                 155                 160

Ile Ser Asp Asp Ile Gln Glu His Gly Tyr Trp Gly Ser Ala Arg Glu
                165                 170                 175

Arg Phe Pro Ile Ser Gln Thr Asp Arg Met Leu Ala Asn Gly Glu Leu
            180                 185                 190

His Ile Ile Ser Gly Asp Pro Glu Lys Gly Arg Val Leu Val Gln
            195                 200                 205

Gly His Asp Asn Ile Thr Leu Ile Arg Ser Gly Gln Asp Trp Val Asn
    210                 215                 220

Ala Asp Glu Lys Glu Arg Glu Leu Tyr Phe Asn Glu Met Leu Pro Ser
225                 230                 235                 240

Leu Gln Ala Gly Met Asp Phe Leu Arg Asp Glu Gly Gln Ala Leu Gly
                245                 250                 255

Cys Tyr Ser Asn Arg Phe Val Arg Asn Val Asp Ile Asp Gly Asn Leu
            260                 265                 270

Leu Asp Ile Ala Tyr Asp Ile Gly Tyr Ile Ala Pro Trp Arg Ser Leu
            275                 280                 285

Asp Lys Leu Glu Arg Trp Ala Glu Ser His Pro Thr His Leu Arg Ile
290                 295                 300

Phe Thr Thr Phe Phe Lys Val Val Thr Gly Leu Gln Asn Leu Arg Leu
305                 310                 315                 320

Tyr His Glu Val Ser Val Ser Asp Ala Lys Asn Gln Val Phe Glu Tyr
                325                 330                 335

Ile Asn Cys His Pro Gln Thr Gly Met Met Arg Asp Ala Gln Met Thr
            340                 345                 350

<210> SEQ ID NO 6
<211> LENGTH: 353
<212> TYPE: PRT
<213> ORGANISM: Acidovorax avanae

<400> SEQUENCE: 6

Met Glu Ser Ala Ile Pro Pro Arg Leu Gln Cys Pro Arg Ser Leu Ser
1               5                   10                  15

Arg Arg Val Ala Asp Asp Tyr Gln Pro Pro Phe Pro Met Trp Val Ala
            20                  25                  30

Arg Pro Gln Ala Asp Leu Gln Gln Val Val Met Ala Tyr Phe Gly Ile
            35                  40                  45

Gln Tyr Gln Gly Glu Ala Gln Lys Pro Arg Ala Leu Ala Val Leu Arg
    50                  55                  60

Glu Trp Val Ala Ala Phe Gly Ala Pro Asp Gly Pro Leu Arg His Asp
65                  70                  75                  80

Leu Thr His His Ile Asp Ala Gln Gly Tyr Asp Asn Leu Ile Ala Val
            85                  90                  95

```
Gly Tyr Trp Arg Asp Pro Glu Ala His Arg Arg Trp Met Gln Ala Pro
                100                 105                 110

Ala Gln Ala Gly Trp Trp Asn Ala Pro Glu Arg Leu Gln Glu Gly Leu
            115                 120                 125

Gly Tyr Phe Arg Glu Val Ser Ala Pro Arg Ala Glu Gln Phe Glu Thr
        130                 135                 140

Leu Tyr Ala Phe Gln Asp Ala Leu Pro Gly Val Gly Gly Val Met Glu
145                 150                 155                 160

Ser Thr Ser Gly Asp Ile Gln Glu His Gly Tyr Trp Gly Ser Met Arg
                165                 170                 175

Asp Arg Phe Pro Ala Ser Gln Val Asp Arg Met Gln Ala Arg Gly Thr
            180                 185                 190

Leu Leu Ile Ala Glu Gly Asp Pro Ala His Gly Gly Arg Val Val Val
        195                 200                 205

Arg Gly His Asp Asn Ile Ala Leu Ile Arg Ser Gly Gln Asp Trp Met
210                 215                 220

Glu Ala Glu Ala Glu Arg Arg Leu Tyr Leu Glu Asp Ile Glu Pro
225                 230                 235                 240

Thr Leu His Ala Gly Met Asp Phe Leu Arg Asp Gln Gly Ala Ala Val
                245                 250                 255

Gly Cys Tyr Ser Asn Arg Tyr Val His Asn Ile Asp Leu Asp Gly Arg
            260                 265                 270

Arg Leu Asp Gln Ser Tyr Asn Ile Gly His Trp Arg Ser Val Asp Leu
        275                 280                 285

Leu Glu Arg Trp Ala Glu Ser His Pro Thr His Leu Arg Ile Phe Gly
290                 295                 300

Thr Phe Phe Lys Val Ala Ala Gly Leu Ser Lys Leu Arg Leu Tyr His
305                 310                 315                 320

Glu Val Ser Val Ser Asp Ala Ala Ser Gln His Phe Glu Tyr Ile Gln
                325                 330                 335

Cys His Pro Ala Thr Gly Met Met Arg Asp Ala Arg Leu Gln Ala Pro
            340                 345                 350

Ala

<210> SEQ ID NO 7
<211> LENGTH: 343
<212> TYPE: PRT
<213> ORGANISM: Actinosynnema mirum

<400> SEQUENCE: 7

Met Ser Ser Leu Pro Leu Asp Asp Arg Ala Thr Ala His Arg Pro Glu
1               5                   10                  15

Gly Tyr Asp Pro Arg Gly Gly Pro Gly His Glu Val Arg Trp Ser Asp
            20                  25                  30

Asp Val Thr His Leu Val Val Ala Arg Phe Gly Val Gln Thr Asp Asp
        35                  40                  45

Ser Ala Ala Gly Val Lys Ala Ile Ala Arg Val Leu Glu Leu Ala Ala
    50                  55                  60

Gly Glu Ser Gly Pro Ala Leu Val Glu Arg Val Ser Asp Asp Ser
65                  70                  75                  80

Glu Met Ala Val Cys Tyr Trp Pro Asp Pro Glu Ala His Arg Ala Trp
                85                  90                  95

Trp Ala Ser Gly Pro Val Arg Asp Trp Trp Ala Ser Leu Pro Val Asp
            100                 105                 110
```

```
Gly Pro Ile Gly His Trp His Glu Thr Ser Val Thr Pro Val Glu Gln
            115                 120                 125

Phe Glu Thr Leu Tyr Ser Ala Glu Phe Ala Ala Gly Pro Ser Arg Phe
        130                 135                 140

Ala Gly Thr Gly Pro Thr Asn Leu His Asp Tyr Asp Asn Ser Thr Leu
145                 150                 155                 160

Asp Arg Met Pro Ala Thr Ala His Arg Asp Leu Arg Gln Glu Arg Ala
                165                 170                 175

Glu Glu Pro Thr Thr Asp Leu Pro Gly Glu Ser Pro Arg Gly Arg
            180                 185                 190

Arg Val Arg Leu Ala Glu Pro Ser Pro Ser Gly Leu Cys Trp Ile Arg
        195                 200                 205

Thr Ala Gln Glu Trp Ser Ile Ala Pro Asp Asp Gln Leu Ala Ser Tyr
    210                 215                 220

Arg Asp Gly Val Glu Pro Ala Tyr Arg Thr Ala Ile Ala His Leu Gln
225                 230                 235                 240

Asp Asn Pro His Asp Thr Gly Cys Leu Ser Ala Arg Leu Val Gly Asn
                245                 250                 255

Leu Asp Ala Asn Gly Ala Arg Ala Ala Gly Ala Glu Ala Val Val Trp
            260                 265                 270

Trp Arg Gly Ile Gly Asp Leu Leu Arg Trp Ala His Asp His Lys Thr
        275                 280                 285

His Gln Asp Ile Leu Asn Gly Phe Trp Glu His Val Ile Ala Lys Phe
    290                 295                 300

Gly Pro Gly Thr Arg Val Arg Leu Trp His Glu Val His Val Leu Pro
305                 310                 315                 320

Glu Gly Ala Leu Thr Ala Glu Tyr Val Asn Cys His Pro Gly Thr Gly
                325                 330                 335

Leu Leu Gln Thr Trp Pro Gly
            340

<210> SEQ ID NO 8
<211> LENGTH: 340
<212> TYPE: PRT
<213> ORGANISM: Bradyrhizobium sp. BTAi1

<400> SEQUENCE: 8

Met Glu Ser Ala Ile Pro Pro His Leu Ile Thr Thr Arg Cys Arg His
1               5                   10                  15

Arg Arg Val Asp Asp Asp Tyr Lys Pro Pro Tyr Pro Ser Phe Val Ala
            20                  25                  30

Arg His Gly Ala Asp Val Ser Arg Val Val Met Ala Tyr Phe Gly Val
        35                  40                  45

Gln Tyr Arg Ala Glu Thr Pro Ala Ala Ala Ser Thr Ala Asp Phe Met
    50                  55                  60

Val Leu Val Ser Arg Ala Asp Gly Pro Ser His Trp Asp Leu Ala His
65                  70                  75                  80

Tyr Val Asp Gln Ala Gly Phe Ala Asn Asp Val Phe Ala Tyr Trp
                85                  90                  95

Asp Asp Val Val Arg Phe Asp Ser Trp Phe Glu Pro Ala Arg Ala Ala
            100                 105                 110

Trp Thr Gly Pro Gly Ala Glu Gly Gly Arg Phe Ile Glu Val Leu
        115                 120                 125

Arg Pro Ala Val Glu Arg Tyr Glu Thr Leu Phe Ser Ser Leu Gly Arg
    130                 135                 140
```

```
Pro Glu Gly Ile Ala Val Ile Ala Glu Gly Met Ser Gly Glu Val Leu
145                 150                 155                 160

Glu His Ala Tyr Trp Gly Gly Met Arg Asp Arg Ile Pro Leu Ser Gln
                165                 170                 175

Thr Ser Glu Met Arg Ser Leu Gly Lys Pro Thr Leu Val Gln Asp Gly
            180                 185                 190

Pro Arg Leu Arg Val Ile Ala Gln Asp Asn Leu Cys Met Ile Arg Ser
        195                 200                 205

Gly Gln Asp Trp Ser Asp Thr Asp Ala Ala Glu Arg Arg Met Tyr Leu
    210                 215                 220

Asp Asp Val Glu Pro Val Leu Arg Glu Gly Met Asp Phe Leu Arg Asp
225                 230                 235                 240

Gln Gly Leu Ser Ile Gly Cys Tyr Ala Asn Arg Tyr Met Arg Leu Arg
                245                 250                 255

Gly Ala Asp Gly Ala Leu Thr Glu Lys Ser Tyr Gly Gln Ser Trp Trp
                260                 265                 270

Gln Ser Leu Ser Ala Leu Glu Arg Trp Ala Glu Ser His Pro Thr His
            275                 280                 285

Val Arg Ile Phe Gly Ala Ala Met Lys Tyr Leu Ser Ser Leu Gly Pro
        290                 295                 300

Ala Ala Arg Leu Arg Leu Tyr His Glu Val Thr Val Ala Ala Ala Asp
305                 310                 315                 320

Glu Gln Phe Phe Glu Tyr Arg Gly Cys His Ala Lys Thr Gly Met Leu
                325                 330                 335

Ala Ala Ala Gly
            340

<210> SEQ ID NO 9
<211> LENGTH: 350
<212> TYPE: PRT
<213> ORGANISM: Burkholderia ambifaria IOP40-10

<400> SEQUENCE: 9

Met Glu Ser Ala Ile Asp Lys His Leu Val Cys Pro Arg Thr Leu Ser
1               5                   10                  15

Arg Arg Val Ala Asp Asp Tyr Gln Pro Pro Phe Pro Met Tyr Val Ala
                20                  25                  30

Arg Ala Ser Glu Asp Leu Ser Gln Val Val Met Gly Tyr Phe Gly Val
            35                  40                  45

Gln Tyr Arg Gly Ala Asp Gln Arg Ser Ala Ala Leu Ala Ala Leu Arg
    50                  55                  60

Arg Ile Val Ala Asp Phe Asp Ala Pro Asp Gly Pro Gly Asn His Asp
65                  70                  75                  80

Leu Thr Gln His Thr Asp Asn Gln Gly Tyr Asp Asn Leu Ile Ala Val
                85                  90                  95

Gly Tyr Trp Arg Asp Pro Asp Ala Tyr Ala Arg Trp Ile Ala Ser Pro
                100                 105                 110

Ala Val Ala Glu Trp Trp Thr Ser Asp Ala Arg Leu Ala Asp Gly Ile
            115                 120                 125

Gly Tyr Phe Arg Glu Ile Val Ala Pro Arg Ala Glu Gln Phe Glu Thr
    130                 135                 140

Leu Tyr Ala Phe Thr Ala Asp Phe Pro Gly Val Gly Ala Ile Met Asp
145                 150                 155                 160
```

Gly Val Ser Gly Glu Ile Glu Glu His Gly Tyr Trp Gly Ser Met Arg
                165                 170                 175

Asp Arg Phe Pro Ile Ser Gln Thr Asp Trp Met His Ala Asp Gly Glu
            180                 185                 190

Leu Arg Ile Val Ala Gly Asp Pro Ala Arg Gly Gly Arg Val Val Val
        195                 200                 205

Leu Ala His Asp Asn Ile Ala Leu Ile Arg Ser Gly Gln Asp Trp Arg
    210                 215                 220

Ala Ala Gln Asp Asp Glu Arg Arg Leu Tyr Leu Asp Glu Ile Glu Pro
225                 230                 235                 240

Thr Leu Arg Ser Gly Met Glu Phe Leu Arg Asp Asn Gly Val Asp Val
                245                 250                 255

Gly Cys Tyr Ser Asn Arg Tyr Val Arg Ser Ile Asp Leu Asp Gly Asn
            260                 265                 270

Leu Leu Asp Glu Ser Tyr Asn Ile Gly His Trp Arg Ser Leu Asp Arg
        275                 280                 285

Leu Glu Arg Trp Ala Glu Ser His Pro Thr His Leu Arg Ile Phe Val
    290                 295                 300

Thr Phe Phe Arg Val Val Thr Gly Leu Ser Lys Leu Arg Leu Tyr His
305                 310                 315                 320

Glu Val Ser Val Phe Asp Ala Lys His Gln Val Tyr Glu Tyr Val Asn
                325                 330                 335

Cys His Pro Asn Thr Gly Met Met Arg Asp Ala Val Ala Arg
            340                 345                 350

<210> SEQ ID NO 10
<211> LENGTH: 350
<212> TYPE: PRT
<213> ORGANISM: Burkholderia ambifaria MC40-6

<400> SEQUENCE: 10

Met Glu Ser Ala Ile Asp Lys His Leu Val Cys Pro Arg Thr Leu Ser
1               5                   10                  15

Arg Arg Val Ala Asp Asp Tyr Gln Pro Pro Phe Pro Met Tyr Val Ala
            20                  25                  30

Arg Ala Ala Glu Asp Leu Ser Gln Val Val Met Gly Tyr Phe Gly Val
        35                  40                  45

Gln Tyr Arg Gly Ala Asp Lys Arg Ser Val Ala Leu Ala Ala Leu Arg
    50                  55                  60

Arg Ile Val Ala Asp Phe Asp Ala Pro Asp Gly Pro Gly Asn His Asp
65                  70                  75                  80

Leu Thr Gln His Thr Asp Asn Gln Gly Tyr Asp Asn Leu Ile Ala Val
                85                  90                  95

Gly Tyr Trp Arg Asp Pro Asp Ala Tyr Ala Arg Trp Ile Ala Ser Pro
            100                 105                 110

Ala Val Ala Glu Trp Trp Ala Ser Asp Ala Arg Leu Ala Asp Gly Ile
        115                 120                 125

Gly Tyr Phe Arg Glu Ile Val Ala Pro Arg Ala Glu Gln Phe Glu Thr
    130                 135                 140

Leu Tyr Ala Phe Thr Asn Asp Phe Pro Gly Val Gly Ser Ile Met Asp
145                 150                 155                 160

Gly Val Ser Gly Glu Ile Glu Glu His Gly Tyr Trp Gly Ser Met Arg
                165                 170                 175

Asp Arg Phe Pro Ile Ser Gln Thr Asp Trp Met His Ala Asp Gly Glu
            180                 185                 190

```
Leu Arg Ile Val Ala Gly Asp Pro Ala Arg Gly Gly Arg Val Val Val
        195                 200                 205

Leu Ala His Asp Asn Ile Ala Leu Ile Arg Ser Gly Gln Asp Trp Arg
    210                 215                 220

Ala Ala Glu Asp Glu Arg Arg Leu Tyr Leu Asp Glu Ile Glu Pro
225                 230                 235                 240

Thr Leu Arg Ser Gly Met Glu Phe Leu Arg Asp Asn Gly Val Asp Val
                245                 250                 255

Gly Cys Tyr Ser Asn Arg Tyr Val Arg Ser Ile Asp Leu Asp Gly Asn
                260                 265                 270

Leu Leu Asp Glu Ser Tyr Asn Ile Gly His Trp Arg Ser Leu Asp Arg
                275                 280                 285

Leu Glu Arg Trp Ala Glu Ser His Pro Thr His Leu Arg Ile Phe Val
                290                 295                 300

Thr Phe Phe Arg Val Val Thr Gly Leu Ser Lys Leu Arg Leu Tyr His
305                 310                 315                 320

Glu Val Ser Val Phe Asp Ala Lys His Gln Val Tyr Glu Tyr Val Asn
                325                 330                 335

Cys His Pro Thr Thr Gly Met Met Arg Asp Ala Ala Arg
                340                 345                 350

<210> SEQ ID NO 11
<211> LENGTH: 352
<212> TYPE: PRT
<213> ORGANISM: Burkholderia cenocepacia MC0-3

<400> SEQUENCE: 11

Met Glu Ser Ala Ile Asp Lys His Leu Ile Cys Pro Arg Thr Leu Ser
1               5                   10                  15

Arg Arg Val Ala Asp Asp Tyr Gln Pro Pro Phe Pro Met Tyr Val Ala
                20                  25                  30

Arg Ala Ala Glu Asp Leu Ser Gln Val Val Met Gly Tyr Phe Gly Val
            35                  40                  45

Gln Tyr Ser Gly Ala Asp Lys Arg Ala Ala Met Ala Ala Leu Arg
    50                  55                  60

Arg Ile Val Ala Asp Phe Gly Gln Asp Gly Pro Asn Asn Phe Asp
65              70                  75                  80

Leu Thr Gln His Thr Asp Asp Glu Gly Tyr Glu Asn Leu Ile Ala Val
                85                  90                  95

Gly Tyr Trp Arg Asp Pro Ala Ala Tyr Ala Arg Trp Ile Ala Ser Pro
            100                 105                 110

Ala Leu Val Glu Trp Trp Ala Ser Asp Ala Arg Leu Ala Asp Gly Ile
        115                 120                 125

Gly Tyr Phe Arg Glu Ile Val Ala Pro Arg Ala Glu Gln Phe Glu Thr
    130                 135                 140

Leu Tyr Ala Phe Thr Ser Asp Phe Pro Gly Val Gly Ala Ile Met Asp
145                 150                 155                 160

Gly Val Ser Gly Glu Ile Glu Glu His Gly Tyr Trp Gly Ser Met Arg
                165                 170                 175

Asp Arg Phe Pro Ile Ser Gln Thr Asp Trp Met Asn Ala Asn Gly Glu
            180                 185                 190

Leu Arg Ile Val Asp Gly Asp Pro Ala Arg Gly Gly Arg Val Val Val
        195                 200                 205
```

```
Leu Ala His Asp Asn Ile Ala Leu Ile Arg Ser Gly Gln Asp Trp Arg
210                 215                 220

Ala Ala Glu Ser Asp Glu Arg Arg Leu Tyr Leu Glu Glu Ile Glu Pro
225                 230                 235                 240

Thr Leu Arg Ser Gly Met Glu Phe Leu Arg Asp Asn Gly Lys Asp Val
                245                 250                 255

Gly Cys Tyr Ser Asn Arg Tyr Val Arg Ser Ile Asp Leu Asp Gly Asn
            260                 265                 270

Val Leu Asp Glu Ser Tyr Asn Ile Gly His Trp Arg Ser Leu Asp Arg
        275                 280                 285

Leu Glu Arg Trp Ala Glu Ser His Pro Thr His Leu Arg Ile Phe Val
290                 295                 300

Thr Phe Phe Arg Val Val Thr Gly Leu Ser Lys Leu Arg Leu Tyr His
305                 310                 315                 320

Glu Val Ser Val Phe Asp Ala Lys His Gln Val Tyr Glu Tyr Val Asn
                325                 330                 335

Cys His Pro Arg Thr Gly Leu Met Arg Asp Ala Val Ala Ile Ala Arg
            340                 345                 350

<210> SEQ ID NO 12
<211> LENGTH: 348
<212> TYPE: PRT
<213> ORGANISM: Pantoea sp. At-9b

<400> SEQUENCE: 12

Met Glu Ser Ala Ile Asp Thr His Leu Lys Cys Pro Arg Thr Leu Ser
1               5                   10                  15

Arg Arg Val His Asp Asp Tyr Gln Pro Pro Phe Pro Met Phe Ala Gly
                20                  25                  30

Arg Ala Asp Ala Ser Leu Thr Gln Val Val Met Ala Tyr Leu Gly Val
            35                  40                  45

Gln Phe Arg Glu Glu Gln Arg Ala Ala Ala Ile Thr Ala Met Gln His
        50                  55                  60

Ile Val Arg Ser Phe Ser Leu Asp Asn Gly Pro Gly Asn His Asp Val
65                  70                  75                  80

Thr Phe His Thr Asp Asn Gln Gly Phe Gly Asn Phe Ile Val Val Gly
                85                  90                  95

Tyr Trp Arg Asp Pro Ala Ala Tyr Cys Arg Trp Leu His Gln Pro Ala
            100                 105                 110

Ile Thr Gly Trp Trp Ser Ser Asp Asp Arg Leu Arg Asp Gly Leu Gly
        115                 120                 125

Tyr Phe Arg Glu Ile Ile Ala Pro Arg Ala Glu Gln Phe Glu Thr Leu
    130                 135                 140

Tyr Ala Phe Lys Glu Ala Leu Pro Gly Val Gly Ala Val Met Asp Asn
145                 150                 155                 160

Leu Ser Gly Glu Ile Gln Glu His Gly Tyr Trp Gly Ser Val Arg Asp
                165                 170                 175

Arg Ile Pro Ala Ser Gln Thr Asp Trp Leu Gln Pro Asp Gly Glu Leu
            180                 185                 190

Arg Ile Ile Ser Gly Asp Pro Ala Ala Gly Arg Val Val Val Gln
        195                 200                 205

Gly His Asp Asn Ile Thr Leu Ile Arg Ser Gly Gln Asp Trp Met Asp
    210                 215                 220

Ala Asp Glu Gln Glu Arg Ala Leu Tyr Phe Thr Glu Met Leu Pro Pro
225                 230                 235                 240
```

```
Leu Gln Ala Gly Met Asp Phe Leu Arg Asp Glu Gly Gln Thr Leu Gly
                245                 250                 255

Cys Tyr Ser Asn Arg Phe Val Arg Asn Val Asp Ile Asp Gly Asn Val
            260                 265                 270

Leu Asp Ile Ala Tyr Asp Ile Gly Phe Trp Arg Ser Leu Asp Arg Leu
        275                 280                 285

Glu Arg Trp Ala Glu Ser His Pro Thr His Leu Arg Ile Phe Thr Thr
290                 295                 300

Phe Phe Arg Val Val Ala Gly Leu Gln Lys Leu Arg Leu Tyr His Glu
305                 310                 315                 320

Val Ser Val Ser Asp Ala Arg Phe Gln Thr Phe Glu Tyr Ile Asn Cys
                325                 330                 335

His Pro Gln Thr Gly Met Leu Arg Asp Ala Val Arg
            340                 345
```

<210> SEQ ID NO 13
<211> LENGTH: 166
<212> TYPE: PRT
<213> ORGANISM: Pseudomonas fluorescens WH6

<400> SEQUENCE: 13

```
Met Lys Pro Thr Thr Glu Leu Gln Val Val Ala Gly Asp Pro Ala Lys
1               5                   10                  15

Gly Gly Arg Val Val Met Gly His Asp Asn Leu Thr Leu Ile Arg
            20                  25                  30

Ser Gly Gln Asp Trp Ala Asp Ala Glu Ala Asp Glu Arg Ser Leu Tyr
        35                  40                  45

Leu Asp Glu Ile Leu Pro Thr Leu Gln Asp Gly Met Asp Phe Leu Arg
    50                  55                  60

Asp Asn Gly Gln Pro Leu Gly Cys Tyr Ser Asn Arg Phe Val Arg Asn
65                  70                  75                  80

Ile Asp Leu Asp Gly Asn Phe Leu Asp Val Ser Tyr Asn Ile Gly His
                85                  90                  95

Trp Arg Ser Val Glu Lys Leu Glu Arg Trp Ala Glu Ser His Pro Thr
            100                 105                 110

His Leu Arg Ile Phe Val Thr Phe Phe Arg Val Ala Ala Gly Leu Lys
        115                 120                 125

Lys Leu Arg Leu Tyr His Glu Val Ser Val Ser Asp Ala Lys Ser Gln
    130                 135                 140

Leu Phe Glu Tyr Ile Asn Cys His Pro His Thr Gly Met Leu Arg Asp
145                 150                 155                 160

Ala Gln Ala Ala Thr Ala
            165
```

<210> SEQ ID NO 14
<211> LENGTH: 186
<212> TYPE: PRT
<213> ORGANISM: Pseudomonas fluorescens WH6

<400> SEQUENCE: 14

```
Met Glu Ser Ala Ile Asp Thr His Leu Lys Cys Pro Arg Thr Leu Ser
1               5                   10                  15

Arg Arg Val Pro Asp Glu Tyr Gln Pro Pro Phe Pro Met Trp Val Ala
            20                  25                  30

Arg Ala Asp Glu Gln Leu Glu Gln Val Val Met Ala Tyr Leu Gly Val
        35                  40                  45
```

-continued

```
Gln Tyr Arg Gly Glu Ala Gln Arg Glu Ala Leu Gln Ala Met Arg
         50                  55                  60

His Ile Val Gly Ser Phe Ser Leu Ala Asp Gly Pro Gln Thr His Asp
 65                  70                  75                  80

Leu Thr His His Thr Asp Ser Ser Gly Phe Asp Asn Leu Ile Val Val
                 85                  90                  95

Gly Tyr Trp Lys Asp Pro Gly Ala His Cys Arg Trp Leu Arg Ser Ala
                100                 105                 110

Pro Val Asn Asp Trp Trp Ala Ser Gln Asp Arg Leu Ser Asp Gly Leu
            115                 120                 125

Gly Tyr Phe Arg Glu Ile Ser Ala Pro Arg Ala Glu Gln Phe Glu Thr
        130                 135                 140

Leu Tyr Ala Phe Gln Asp Asn Leu Pro Gly Val Gly Ala Val Met Asp
145                 150                 155                 160

Ala Thr Ser Gly Glu Ile Glu Asn Thr Val Thr Gly Ala Arg Cys Ala
                165                 170                 175

Thr Ala Ser Pro Ser Pro Arg Gln Thr Gly
            180                 185
```

<210> SEQ ID NO 15
<211> LENGTH: 352
<212> TYPE: PRT
<213> ORGANISM: Pseudomonas putida F1

<400> SEQUENCE: 15

```
Met Glu Ser Ala Ile Asp Lys His Leu Val Cys Pro Arg Thr Leu Ser
 1               5                  10                  15

Arg Arg Val Pro Asp Asp Tyr Gln Pro Pro Phe Pro Met Trp Val Gly
            20                  25                  30

Arg Ala Asp Glu Gln Leu Thr Gln Val Val Met Ala Tyr Leu Gly Val
        35                  40                  45

Gln Tyr Arg Gly Asp Gly Gln Arg Glu Arg Ala Leu Gln Ala Met Arg
     50                  55                  60

Glu Ile Leu Gly Ser Phe Ser Leu Thr Asp Gly Pro Leu Thr His Asp
 65                  70                  75                  80

Leu Thr His His Thr Asp Ser Ser Gly Tyr Asp Asn Leu Met Ile Val
                 85                  90                  95

Gly Tyr Trp Lys Asp Ala Gly Ala Tyr Cys Arg Trp Leu Arg Ser Pro
                100                 105                 110

Glu Val Asp Gly Trp Trp Ser Ser Pro Gln Arg Leu Asn Asp Gly Leu
            115                 120                 125

Gly Tyr Tyr Arg Glu Ile Thr Ala Pro Arg Ala Glu Gln Phe Glu Thr
        130                 135                 140

Leu Tyr Ala Phe Gln Asn Asp Leu Pro Gly Val Gly Ala Ile Met Asp
145                 150                 155                 160

Asn Thr Ser Gly Glu Ile Glu Glu His Gly Tyr Trp Gly Ser Met Arg
                165                 170                 175

Asp Arg Phe Pro Val Ser Gln Thr Asp Trp Met Asn Pro Asn Gly Glu
            180                 185                 190

Leu Arg Val Val Ala Gly Asp Pro Ala Lys Gly Gly Arg Val Val Val
        195                 200                 205

Leu Gly His Asp Asn Ile Ala Leu Ile Arg Ser Gly Gln Asp Trp Ala
    210                 215                 220
```

```
Thr Ala Glu Ala Ala Glu Arg Ser Leu Tyr Leu Asp Glu Ile Leu Pro
225                 230                 235                 240

Thr Leu Gln Asp Gly Met Asp Phe Leu Arg Asp Asn Gly Gln Pro Leu
            245                 250                 255

Gly Cys Tyr Ser Asn Arg Phe Val Arg Asn Ile Asp Ala Asp Gly Asn
        260                 265                 270

Leu Leu Asp Met Ser Tyr Asn Ile Gly His Trp Arg Ser Leu Glu Lys
    275                 280                 285

Leu Glu Arg Trp Ala Glu Ser His Pro Thr His Leu Arg Ile Phe Val
290                 295                 300

Thr Phe Phe Arg Val Ala Ala Gly Leu Glu Lys Leu Arg Leu Tyr His
305                 310                 315                 320

Glu Val Ser Val Ser Asp Ala Ser Ser Gln Val Phe Glu Tyr Ile Asn
                325                 330                 335

Cys His Pro His Thr Gly Met Leu Arg Asp Ala Lys Val Ser Ser Asn
            340                 345                 350

<210> SEQ ID NO 16
<211> LENGTH: 352
<212> TYPE: PRT
<213> ORGANISM: Pseudomonas putida Stamm BIRD-1

<400> SEQUENCE: 16

Met Glu Ser Ala Ile Asp Lys His Leu Met Cys Pro Arg Thr Leu Ser
1               5                   10                  15

Arg Arg Val Pro Asp Asp Tyr Gln Pro Pro Phe Pro Met Trp Val Gly
            20                  25                  30

Arg Ala Asp Glu Gln Leu Thr Gln Val Val Met Ala Tyr Leu Gly Val
        35                  40                  45

Gln Tyr Arg Gly Asp Ser Gln Arg Glu Arg Ala Leu Gln Ala Met Arg
    50                  55                  60

Glu Ile Leu Gly Ser Phe Ser Leu Ser Asp Gly Pro Leu Thr His Asp
65                  70                  75                  80

Leu Thr His His Thr Asp Ser Ser Gly Tyr Asp Asn Leu Met Ile Val
                85                  90                  95

Gly Tyr Trp Lys Asp Thr Gly Ala Tyr Cys Arg Trp Ser Arg Ser Pro
            100                 105                 110

Glu Val Asp Gly Trp Ser Ser Pro Gln Arg Leu Asn Asp Gly Leu
        115                 120                 125

Gly Tyr Tyr Arg Glu Ile Thr Ala Pro Arg Ala Glu Gln Phe Glu Thr
    130                 135                 140

Leu Tyr Ala Phe Gln Ser Asp Leu Pro Gly Val Gly Ala Ile Met Asp
145                 150                 155                 160

Asn Thr Ser Gly Glu Ile Glu Glu His Gly Tyr Trp Gly Ser Met Arg
                165                 170                 175

Asp Arg Phe Pro Val Ser Gln Thr Asp Trp Met Asn Pro Asn Gly Glu
            180                 185                 190

Leu Arg Val Val Ala Gly Asp Pro Ala Lys Gly Gly Arg Val Val Val
        195                 200                 205

Ile Gly His Asp Asn Ile Ala Leu Ile Arg Ser Gly Gln Asp Trp Ala
    210                 215                 220

Ala Ala Glu Ala Ala Glu Arg Ser Leu Tyr Leu Asp Glu Ile Leu Pro
225                 230                 235                 240

Thr Leu Gln Asp Gly Met Asp Phe Leu Arg Asp Asn Gly Gln Pro Leu
                245                 250                 255
```

```
Gly Cys Tyr Ser Asn Arg Phe Val Arg Asn Ile Asp Ala Asp Gly Asn
            260                 265                 270

Val Leu Asp Met Ser Tyr Asn Ile Gly His Trp Arg Ser Leu Glu Lys
            275                 280                 285

Leu Glu Arg Trp Ala Glu Ser His Pro Thr His Leu Arg Ile Phe Val
290                 295                 300

Thr Phe Phe Arg Val Ala Ala Gly Leu Glu Lys Leu Arg Leu Tyr His
305                 310                 315                 320

Glu Val Ser Val Ser Asp Ala Ser Ser Gln Val Phe Glu Tyr Ile Asn
                325                 330                 335

Cys His Pro His Thr Gly Met Leu Arg Asp Ala Lys Val Ser Ser Asn
                340                 345                 350
```

<210> SEQ ID NO 17
<211> LENGTH: 332
<212> TYPE: PRT
<213> ORGANISM: Shewanella woodyi ATCC 51908

<400> SEQUENCE: 17

```
Met Met Asn Asn Met Pro Lys Asn Trp Thr Pro Pro Ala Pro Ala Trp
1               5                   10                  15

Thr Ser Leu Trp Lys Thr Asp Glu Glu Asn Leu Val Cys Gly Leu Phe
            20                  25                  30

Ala Ile Gln Gly Gln His Ser Ala Pro Leu Asp Asp Trp Ala Lys Lys
        35                  40                  45

Ala Phe Thr Gly Glu Phe Ser Pro Lys Leu Leu Glu Gln Gly Met Phe
    50                  55                  60

Thr Asp Lys Ala Gly Ile Thr Asn Tyr Leu Tyr Ile Ala Tyr Trp Phe
65                  70                  75                  80

Ala Ser Asp Tyr Lys Thr Trp Gln Gln Ser Ala Ala Asn Ser Trp
                85                  90                  95

Trp Ala Ser Pro Leu Leu Asp Glu Gly Asp Ile Ser Val Trp Arg Glu
                100                 105                 110

Val Phe Thr Met Pro His Gln Arg Phe Glu Thr Leu His Ser Ser Glu
            115                 120                 125

Asn Ala His Gly Ala Ala Arg Leu Ser Pro Ser Leu Glu Gly Pro Met
        130                 135                 140

Met Glu His Gly Tyr Ser Gly Ala Ala Arg Asp Arg Ile Pro Cys Ser
145                 150                 155                 160

Ser Ser Gln Asp Ile Lys Asn Asp Asn Ser Ile Trp Glu His Leu Gln
                165                 170                 175

Val Asn Val Glu Asn Lys Ser Asn Arg Ile Lys Leu Ser Pro Pro Lys
            180                 185                 190

Asn Met Cys Val Ile Arg Ser Gly Gln Asp Trp Thr His Cys Glu Glu
        195                 200                 205

Asp Glu Lys Glu Tyr Tyr Leu Thr Asn Val His Thr Val Leu Lys Lys
    210                 215                 220

Gly Met Asp Tyr Leu Ser Asn Asn Pro Val Lys Thr His Cys Ala Ser
225                 230                 235                 240

Met Arg Phe Ile Thr Lys Thr Asp Gly Asn Trp Cys Ser Val Glu Gln
                245                 250                 255

Thr Phe Gly Leu Gly Tyr Gly Asn Asp Ile Tyr Ala Phe Glu Asn Trp
            260                 265                 270
```

```
Ala Lys Ser His Pro Thr His Ile Ala Ile Phe Asp Arg Phe Met Gly
            275                 280                 285

Met Val Glu Lys Tyr Asn Val Asp Leu Lys Leu Gln Leu Trp His Glu
        290                 295                 300

Val Thr Leu Ile Pro Glu Gln Asp Cys Glu Phe Glu Tyr Ile Asn Cys
305                 310                 315                 320

His Gly Gln Thr Gly Leu Leu Cys Tyr Ile Asn Ile
                325                 330

<210> SEQ ID NO 18
<211> LENGTH: 343
<212> TYPE: PRT
<213> ORGANISM: Sphingomonas wittichii RW1

<400> SEQUENCE: 18

Met Asp Ser Ser Ile Thr Pro His Leu Ala Cys Pro Arg Ser Arg Pro
1               5                   10                  15

Arg Arg Ile Ala Asp Asp Tyr Ala Pro Pro Tyr Pro Ala Trp Ser Ala
            20                  25                  30

Arg Ile Asp Pro Ala Ile Gly Gln Val Val Met Ala Ser Tyr Gly Val
        35                  40                  45

Gln Gly Arg Glu Ser Gly Asp Val Ala Ala Ala Leu Ala His Val Arg
    50                  55                  60

Ala Leu Arg Ala Thr Leu Asp Ala Asp Val Arg His Val Asp Leu Ala
65                  70                  75                  80

Arg Tyr Val Asp Glu Ala Gly Tyr Asp Thr Leu Val Leu Gln Pro Tyr
                85                  90                  95

Trp Thr Asp Pro Glu Ala Phe Arg Arg Trp Glu Ala Arg Ala Asp Val
            100                 105                 110

Ala Ala Leu Leu Ala Ala Glu Thr Gly Leu Gly His Phe Arg Glu Ile
        115                 120                 125

Leu Thr Pro Thr Val Glu Arg Leu Glu Thr Leu Tyr Ser Thr Glu Asp
    130                 135                 140

Glu Met Glu Gly Leu Gly Arg Ala Leu Glu Arg Arg Ser Pro Pro Val
145                 150                 155                 160

Gln Glu His Ala Tyr Trp Gly Ser Ala Arg Asp Arg Phe Pro Ile Ala
                165                 170                 175

Gln Thr Asp Ala Leu Glu Pro Ala Gly Gln Leu Gly Phe Ala Ala Asp
            180                 185                 190

Gly Ala Gly Arg Val Thr Val Arg Gly His Asp Asn Ile Ala Ile Ile
        195                 200                 205

Arg Ser Gly Gln Asp Trp Gly Pro Thr Gly Gly Glu Arg Arg Leu
    210                 215                 220

Tyr Leu Ala Glu Ile Glu Pro Val Leu Arg Ala Gly Met Asp Phe Leu
225                 230                 235                 240

Arg Asp Arg Gly Gly Glu Cys Gly Cys Tyr Leu Asn Arg Tyr Met Arg
                245                 250                 255

Ile Val Asp Met Asp Gly Ala Pro Gln Glu Lys Ser Phe Gly Trp Ser
            260                 265                 270

Tyr Trp Arg Ser Leu Gly Asp Met Glu Asn Trp Ser Glu Ala His Pro
        275                 280                 285

Ser His Leu Ala Ile Phe Gly Thr Phe Met Arg Ile Val Gln Gln Leu
    290                 295                 300

Asn Phe Asp Leu Lys Leu Arg Leu Trp His Glu Val Tyr Val Val Thr
305                 310                 315                 320
```

```
Pro Asp Gln Gln Leu Tyr Asp Tyr Arg Asn Cys His Pro Asp Thr Gly
            325                 330                 335

Phe Leu Lys Gln Met Pro Arg
            340

<210> SEQ ID NO 19
<211> LENGTH: 353
<212> TYPE: PRT
<213> ORGANISM: Variovorax paradoxus EPS

<400> SEQUENCE: 19

Met Glu Ser Ala Ile Ala Glu His Leu Lys Cys Pro Arg Thr Arg His
1               5                   10                  15

Arg Arg Val Glu Asp Asp Tyr Thr Pro Pro Tyr Pro Val Trp Ser Ala
            20                  25                  30

Arg Ala Pro Thr Ser Val Thr Gln Val Thr Met Gly Tyr Phe Gly Val
        35                  40                  45

Gln Ser Arg Gly Pro Glu Met Gln Gly Arg Ala Cys Ala Ala Leu Met
    50                  55                  60

Lys Ile Ala Arg Asp Phe Ala Leu Pro Asp Gly Pro Gly His His Asp
65                  70                  75                  80

Leu Ala His Tyr Val Asp Ala Asp Gly Phe Asp Asn Met Val Ala Ile
                85                  90                  95

Ala Tyr Trp His Asp Ala Ala Ala Phe Ala Arg Trp Ser Ala Thr Pro
            100                 105                 110

Ala Ile Asp Ala Trp Trp Arg Ser Asp Glu Arg Leu Asn Glu Gly Leu
        115                 120                 125

Gly Tyr Phe Arg Glu Ile Ala Ser Pro Arg Val Glu His Phe Glu Thr
    130                 135                 140

Met Phe Asn Thr Pro Asp Arg Phe Glu Gly Ile Gly Val Val Met Gly
145                 150                 155                 160

Glu Leu Ser Gly Glu Leu Gln Glu His Gly Tyr Trp Gly Ser Met Arg
                165                 170                 175

Asp Arg Ile Pro Leu Ser Gln Thr Asp Ala Leu Ser Pro Ser Gly Thr
            180                 185                 190

Arg Ala Val Val Ala Gly Thr Pro Ala Pro Gly Gln Arg Val Arg Ile
        195                 200                 205

Ala Gly His Glu Asn Ile Ala Met Ile Arg Ser Gly Gln Glu Trp Ala
    210                 215                 220

Asp Thr Thr Gly Gln Glu Arg Thr Leu Tyr Leu Glu Asp Met Glu Pro
225                 230                 235                 240

Val Leu Arg Glu Gly Met Asp Phe Leu Arg Asp Gln Gly Leu Gly Ile
                245                 250                 255

Gly Cys Tyr Ser Asn Arg Tyr Met His His Leu Asp Ala Lys Gly Ala
            260                 265                 270

Pro Leu Gln Lys Ser Phe Gly Leu Ser Tyr Trp Arg Ser Leu Ala Asp
        275                 280                 285

Met Glu Arg Trp Ala Glu Ser His Pro Thr His Val Ala Ile Phe Gly
    290                 295                 300

Ser Phe Met Arg Tyr Val Gln Ala Leu Asn Phe Gln Leu Gln Leu Arg
305                 310                 315                 320

Val Tyr His Glu Val Ser Val Leu Lys Ala Asp Glu Gln Ser Tyr Glu
                325                 330                 335
```

-continued

```
Tyr Ile Asn Cys Arg Ala Arg Ser Gly Leu Met Asn Gly Leu Ala Val
            340                 345                 350

Thr

<210> SEQ ID NO 20
<211> LENGTH: 305
<212> TYPE: PRT
<213> ORGANISM: Variovorax paradoxus S110

<400> SEQUENCE: 20

Met Glu Ser Arg Asp Ala Asp Ala Arg Ala Leu Leu Ala Arg Val Ala
1               5                   10                  15

Asn Thr Phe Ala Gly Val Gly Gly Pro Ala Ser Leu Gly Arg Gly Val
            20                  25                  30

Ala Thr Gly Ala Gly Gly Glu Arg Ser Asp Ile Phe Tyr Ala Tyr Trp
        35                  40                  45

Asn Ser Ser Ala Glu Tyr Ala Ser Trp Leu Thr Thr Pro Arg Val Ala
    50                  55                  60

Ser Leu Trp Thr Asp Asp Ala Leu Leu Arg Gly Pro Ile Gly Leu Trp
65                  70                  75                  80

Arg Glu Ser Met Ile Ile Pro Val Glu Arg Asn Glu Thr Asn Tyr Ser
                85                  90                  95

Asn Asp Ala Ala Tyr Asp Gly Ile Ala Gln Ile Asp Lys Glu Met Arg
            100                 105                 110

Lys Thr Asp Val His Gly Tyr Trp Gly Ser Ala Arg Glu Arg Ile Pro
        115                 120                 125

Ala Ser Ala His Asp Thr Met Pro Ser Ala Ala Pro Asp Phe Met Gly
    130                 135                 140

Arg Pro Ala Ala Ser Met Glu Thr Leu Gly Arg Arg Phe Arg Ile Thr
145                 150                 155                 160

Leu Pro Gly Asn Thr Cys Val Ile Arg Ser Phe Gln Asp Trp Ser Gln
                165                 170                 175

Ala Gln Ala Ala Glu Val Asp Trp Tyr Leu Gly Asn Val Glu Pro Val
            180                 185                 190

Leu Arg Val Gly Leu Asp Tyr Leu Asn Gly Asn Arg Thr Glu Ala Lys
        195                 200                 205

Cys Tyr Gly Met Arg Tyr Ile Arg Glu Tyr Asp Ile Ser Gly Ala Ile
    210                 215                 220

Asp Leu Asn Arg Thr Ser Thr Phe Gly Tyr Phe Glu Ser Leu Gln Thr
225                 230                 235                 240

Leu Glu Arg Trp Thr His Thr His Pro Thr His Leu Asp Ile Phe Arg
                245                 250                 255

Ala Ala Ile Ser Met Val Gln Arg Phe Gln Gly Glu Val Ala Val Lys
            260                 265                 270

Leu Gly His Glu Val Ser Val Leu Pro Glu Gly Met Leu Ser Ala Glu
        275                 280                 285

Tyr Val Asn Cys Ala Arg Ser Thr Gly Phe Leu Pro Trp Phe His Glu
    290                 295                 300

Asp
305

<210> SEQ ID NO 21
<211> LENGTH: 353
<212> TYPE: PRT
<213> ORGANISM: Variovorax paradoxus S110
```

<400> SEQUENCE: 21

Met Glu Ser Ala Ile Ala Glu His Leu Lys Cys Pro Arg Thr Arg His
1               5                   10                  15

Arg Arg Val Glu Asp Asp Tyr Ala Pro Pro Tyr Pro Ala Trp Ser Ala
            20                  25                  30

Arg Ala Pro Gly Ala Val Arg Gln Val Val Met Gly Tyr Phe Gly Val
        35                  40                  45

Gln Ser Arg Gly Ala Gly Met Gln Gly Arg Ala Cys Ala Ala Leu Met
    50                  55                  60

Lys Ile Ala Ala Gly Phe Ala Leu Pro Asp Gly Pro Gly His His Asp
65                  70                  75                  80

Phe Ala His His Val Asp Ala Ala Gly Cys Asp Asn Met Val Ala Ile
                85                  90                  95

Ala Tyr Trp Asn Asp Pro Ala Ala His Ala Arg Trp Cys Thr Ala Pro
            100                 105                 110

Glu Val Asp Ala Trp Trp Arg Ser Asp Glu Arg Leu Ala Asp Gly Leu
        115                 120                 125

Gly Tyr Phe Arg Glu Ile Val Ala Pro Arg Ala Glu His Phe Glu Thr
    130                 135                 140

Met Phe Asn Thr Pro Asp Arg Leu Glu Gly Val Gly Val Val Met Gly
145                 150                 155                 160

Gly Val Ser Gly Glu Leu Gln Glu His Gly Tyr Trp Gly Ser Met Arg
                165                 170                 175

Asp Arg Ile Pro Leu Ser Gln Thr Asp Ala Met Ala Pro Ser Gly Thr
            180                 185                 190

Arg Ala Val Ile Ala Gly Ala Pro Ala Pro Gly Gln Arg Val Arg Ile
        195                 200                 205

Ala Gly His Glu Asn Ile Ala Met Ile Arg Ser Gly Gln Glu Trp Ala
    210                 215                 220

Asp Thr Thr Gly Gln Glu Arg Ala Leu Tyr Leu Gly Glu Met Glu Pro
225                 230                 235                 240

Val Leu Arg Glu Gly Met Asp Phe Leu Arg Asp Gln Gly Leu His Ile
                245                 250                 255

Gly Cys Tyr Ser Asn Arg Tyr Met Gln His Leu Asp Ala Lys Gly Ala
            260                 265                 270

Pro Leu Glu Lys Ser Phe Gly Leu Ser Phe Trp His Ser Leu Ala Asp
        275                 280                 285

Met Glu Arg Trp Ala Glu Ser His Pro Thr His Val Ala Ile Phe Gly
    290                 295                 300

Ser Phe Met Arg Tyr Val Gln Ala Leu Asn Phe Gln Leu Gln Leu Arg
305                 310                 315                 320

Val Tyr His Glu Val Ser Val Leu Lys Ala Asp Glu Gln Ser Tyr Glu
                325                 330                 335

Tyr Ile Asn Cys His Ala Gly Ser Gly Leu Met Asn Gly Leu Gly Glu
            340                 345                 350

Val

<210> SEQ ID NO 22
<211> LENGTH: 347
<212> TYPE: PRT
<213> ORGANISM: Xanthobacter autotrophicus Py2

<400> SEQUENCE: 22

Met Val Phe His Val Glu Tyr Pro Arg Ile Val Pro Glu Arg Arg Pro
1               5                   10                  15

Pro Gly His Glu Pro Ala Ala Pro Arg Phe Ser Leu Arg Trp Glu Gln
            20                  25                  30

Pro Val Gly Leu Val Val Cys Ala Tyr Phe Gly Leu Gln Gly Gln Asp
        35                  40                  45

Leu Ala Trp Asp Glu Gln Lys Ala Phe Phe Asp Arg Leu Gln Thr Ser
50                  55                  60

Phe Gly Thr Asp Gly Pro Val Ala His Glu Ile Met Arg Met His Asp
65                  70                  75                  80

Glu Thr Gly Ala Val Asn Ala Ile Leu Val Ala Tyr Trp Leu Asp Ala
                85                  90                  95

Thr Ala His Ala Arg Trp Glu Arg Asn Ser Pro Phe Met Ala Trp Phe
            100                 105                 110

Arg Asp Pro Ala Arg Leu Glu Gly Thr Arg Gly Val Trp Arg Glu Thr
        115                 120                 125

Met His Val Pro Tyr Asp Arg His Glu Thr Ile Tyr Ser Thr Pro Ser
130                 135                 140

Tyr Val Ile Gly Leu Ala Arg Thr Pro Gly Ala Thr Arg Val Pro Ile
145                 150                 155                 160

Thr Thr Asn Gly Tyr Phe Gly Ala Met Arg Asp Arg Met Pro Val Ser
                165                 170                 175

Ala Ile Asp Thr Leu Glu Ser Pro Leu Gly Ala Met Pro Pro Arg Arg
            180                 185                 190

Ala Pro Asp Ser His Gly Arg Arg Leu Thr Ala Ala Phe Pro Leu Asn
        195                 200                 205

Leu Ile Ser Ile Arg Ser Gly Gln Tyr Trp Glu Gly Ala Gly Asn Glu
210                 215                 220

Gln Thr Ala Asp Tyr Ile Asp Asn Leu Gln Pro Lys Leu Met Arg Gly
225                 230                 235                 240

Met Ala His Leu Ser Ser His Pro Glu Gln Thr Gly Thr Leu Thr Leu
                245                 250                 255

Arg Ile Met Thr Asn Leu Asp Ala Glu Gly Arg Pro Arg Ala Glu Thr
            260                 265                 270

Ser Val His Gly Tyr Phe Leu Ser Met Ala His Leu Glu Glu Trp Ser
        275                 280                 285

Arg Ser His Glu Thr His Leu Asp Ile Tyr Arg His Ala Ile Ala Met
290                 295                 300

Asn Arg Leu Tyr Lys Glu Lys Arg Glu Val Phe Thr Trp His Glu Val
305                 310                 315                 320

Phe Ala Leu Leu Pro Gly Ala His Ala Glu Tyr Ala Asn Cys His Gly
                325                 330                 335

Gly Thr Gly Leu Leu Pro Tyr Phe Ala Asp Ala
            340                 345

<210> SEQ ID NO 23
<211> LENGTH: 363
<212> TYPE: PRT
<213> ORGANISM: Gibberella zeae

<400> SEQUENCE: 23

Met Leu Arg Ser Arg Phe Pro Ala Ser His His Phe Thr Val Ser Val
1               5                   10                  15

Phe Gly Cys Gln Tyr His Ser Glu Ala Pro Ser Val Glu Lys Thr Glu
            20                  25                  30

Leu Ile Gly Arg Phe Asp Lys Leu Ile Asp Ser Ala Ala Ile His Val
                35                  40                  45

Glu His Leu Glu Gln Asn Asp Val Pro Ser Lys Ile Trp Met Ser Tyr
 50                  55                  60

Trp Glu Ser Pro Gln Lys Phe Lys Gln Trp Trp Glu Lys Asp Asp Thr
 65                  70                  75                  80

Ala Ser Phe Trp Ala Ser Leu Pro Asp Asp Ala Gly Phe Trp Arg Glu
                 85                  90                  95

Thr Phe Ser Leu Pro Ala Thr Arg Ala Met Tyr Glu Gly Thr Gly Lys
                100                 105                 110

Asp Ala Tyr Gly Phe Gly His Cys Gly Ser Leu Ile Pro Leu Thr Thr
                115                 120                 125

Lys Thr Gly Tyr Trp Gly Ala Tyr Arg Ser Arg Met Thr Pro Asp Phe
                130                 135                 140

Glu Gly Asp Thr Phe Ser Ser Pro Ile Pro Thr Tyr Ala Asp Gln Ser
145                 150                 155                 160

Val Pro Ala Asp Lys Ile Arg Pro Gly Arg Val Arg Ile Thr Asp Phe
                165                 170                 175

Pro Asp Asn Leu Cys Met Val Val Glu Gly Gln His Tyr Ala Asp Met
                180                 185                 190

Gly Glu Arg Glu Arg Glu Tyr Trp Asn Glu Asn Phe Asp Gly Leu Thr
                195                 200                 205

Lys Gln Trp Val Thr Asn Val Val Thr Ala Gly His Glu Gln Gly Met
                210                 215                 220

Val Ile Ala Arg Ala Cys His Gly Phe Ala Gly Glu Lys Lys Leu Gly
225                 230                 235                 240

Ala Thr Asn Gly Pro Val Asn Gly Ile Phe Pro Gly Leu Asp Tyr Val
                245                 250                 255

His Gln Ala Gln Ile Leu Ile Trp Gln Asp Ile Ser Lys Met Glu His
                260                 265                 270

Ile Gly Arg Tyr Asp Gln Thr His Val Lys Leu Arg Arg Asp Phe Met
                275                 280                 285

Lys Ala Tyr Gly Pro Gly Gly Glu Met Glu Gly Asp Leu Leu Leu
                290                 295                 300

Trp Val Asp Leu Gly Ile Leu Lys Lys Asp Glu Ile Asp Ala Glu Tyr
305                 310                 315                 320

Val Gly Cys Tyr Glu Ser Thr Gly Phe Leu Lys Leu Asp Lys Gly Gln
                325                 330                 335

Phe Phe Lys Val Glu Ser Thr Ala Gly Ser Lys Leu Pro Ser Phe Phe
                340                 345                 350

Asp Glu Pro Ile Glu Ser Lys Pro Ile Glu Trp
                355                 360

<210> SEQ ID NO 24
<211> LENGTH: 352
<212> TYPE: PRT
<213> ORGANISM: Pseudomonas chlororaphis

<400> SEQUENCE: 24

Met Glu Ser Ala Ile Asp Thr His Leu Lys Cys Pro Arg Thr Leu Ser
1               5                   10                  15

Arg Arg Val Pro Glu Gly Tyr Gln Pro Pro Phe Pro Met Trp Val Ala
                20                  25                  30

```
Arg Ala Asp Glu Gln Leu Gln Val Val Met Gly Tyr Leu Gly Val
         35                  40                  45

Gln Tyr Arg Gly Glu Ala Gln Arg Glu Ala Leu Gln Ala Met Arg
 50                  55                  60

His Ile Val Ser Ser Phe Ser Leu Pro Asp Gly Pro Gln Thr His Asp
 65                  70                  75                  80

Leu Thr His His Thr Asp Ser Ser Gly Phe Asp Asn Leu Met Val Val
                 85                  90                  95

Gly Tyr Trp Lys Asp Pro Ala Ala His Cys Arg Trp Leu Arg Ser Ala
                100                 105                 110

Glu Val Asn Asp Trp Trp Thr Ser Gln Asp Arg Leu Gly Glu Gly Leu
                115                 120                 125

Gly Tyr Phe Arg Glu Ile Ser Ala Pro Arg Ala Glu Gln Phe Glu Thr
130                 135                 140

Leu Tyr Ala Phe Gln Asp Asn Leu Pro Gly Val Gly Ala Val Met Asp
145                 150                 155                 160

Ser Thr Ser Gly Glu Ile Glu Glu His Gly Tyr Trp Gly Ser Met Arg
                165                 170                 175

Asp Arg Phe Pro Ile Ser Gln Thr Asp Trp Met Lys Pro Thr Asn Glu
                180                 185                 190

Leu Gln Val Val Ala Gly Asp Pro Ala Lys Gly Gly Arg Val Val Ile
                195                 200                 205

Met Gly His Asp Asn Ile Ala Leu Ile Arg Ser Gly Gln Asp Trp Ala
210                 215                 220

Asp Ala Glu Ala Glu Arg Ser Leu Tyr Leu Asp Glu Ile Leu Pro
225                 230                 235                 240

Thr Leu Gln Asp Gly Met Asp Phe Leu Arg Asp Asn Gly Gln Pro Leu
                245                 250                 255

Gly Cys Tyr Ser Asn Arg Phe Val Arg Asn Ile Asp Leu Asp Gly Asn
                260                 265                 270

Phe Leu Asp Val Ser Tyr Asn Ile Gly His Trp Arg Ser Leu Glu Lys
                275                 280                 285

Leu Glu Arg Trp Ala Glu Ser His Pro Thr His Leu Arg Ile Phe Val
290                 295                 300

Thr Phe Phe Arg Val Ala Ala Gly Leu Lys Lys Leu Arg Leu Tyr His
305                 310                 315                 320

Glu Val Ser Val Ser Asp Ala Lys Ser Gln Val Phe Glu Tyr Ile Asn
                325                 330                 335

Cys His Pro His Thr Gly Met Leu Arg Asp Ala Val Ala Pro Thr
                340                 345                 350

<210> SEQ ID NO 25
<211> LENGTH: 352
<212> TYPE: PRT
<213> ORGANISM: Pseudomonas sp. K-9

<400> SEQUENCE: 25

Met Glu Ser Ala Ile Asp Thr His Leu Lys Cys Pro Arg Thr Leu Ser
  1               5                  10                  15

Arg Arg Val Pro Asp Glu Tyr Gln Pro Phe Ala Met Trp Met Ala
                 20                  25                  30

Arg Ala Asp Glu His Leu Glu Gln Val Val Met Ala Tyr Phe Gly Val
         35                  40                  45

Gln Tyr Arg Gly Glu Ala Gln Arg Ala Ala Leu Gln Ala Met Arg
 50                  55                  60
```

His Ile Val Glu Ser Phe Ser Leu Ala Asp Gly Pro Gln Thr His Asp
65                  70                  75                  80

Leu Thr His His Thr Asp Asn Ser Gly Phe Asp Asn Leu Ile Val Val
            85                  90                  95

Gly Tyr Trp Lys Asp Pro Ala Ala His Cys Arg Trp Leu Arg Ser Ala
        100                 105                 110

Pro Val Asn Ala Trp Trp Ala Ser Glu Asp Arg Leu Asn Asp Gly Leu
    115                 120                 125

Gly Tyr Phe Arg Glu Ile Ser Ala Pro Arg Ala Glu Gln Phe Glu Thr
130                 135                 140

Leu Tyr Ala Phe Gln Asp Asn Leu Pro Gly Val Gly Ala Val Met Asp
145                 150                 155                 160

Arg Ile Ser Gly Glu Ile Glu Glu His Gly Tyr Trp Gly Ser Met Arg
                165                 170                 175

Asp Arg Phe Pro Ile Ser Gln Thr Asp Trp Met Lys Pro Thr Ser Glu
            180                 185                 190

Leu Gln Val Ile Ala Gly Asp Pro Ala Lys Gly Arg Val Val Val
        195                 200                 205

Leu Gly His Gly Asn Leu Thr Leu Ile Arg Ser Gly Gln Asp Trp Ala
210                 215                 220

Asp Ala Glu Ala Glu Arg Ser Leu Tyr Leu Asp Glu Ile Leu Pro
225                 230                 235                 240

Thr Leu Gln Asp Gly Met Asp Phe Leu Arg Asp Asn Gly Gln Pro Leu
            245                 250                 255

Gly Cys Tyr Ser Asn Arg Phe Val Arg Asn Ile Asp Leu Asp Gly Asn
        260                 265                 270

Phe Leu Asp Val Ser Tyr Asn Ile Gly His Trp Arg Ser Val Glu Lys
    275                 280                 285

Leu Glu Arg Trp Thr Glu Ser His Pro Thr His Leu Arg Ile Phe Val
290                 295                 300

Thr Phe Phe Arg Val Ala Ala Gly Leu Lys Lys Leu Arg Leu Tyr His
305                 310                 315                 320

Glu Val Ser Val Ser Asp Ala Lys Ser Gln Ile Phe Gly Tyr Ile Asn
                325                 330                 335

Cys His Pro Gln Thr Gly Met Leu Arg Asp Ala Gln Val Ser Pro Ala
            340                 345                 350

<210> SEQ ID NO 26
<211> LENGTH: 353
<212> TYPE: PRT
<213> ORGANISM: Rhodococcus erythropolis

<400> SEQUENCE: 26

Met Glu Ser Ala Ile Gly Glu His Leu Gln Cys Pro Arg Thr Leu Thr
1               5                   10                  15

Arg Arg Val Pro Asp Thr Tyr Thr Pro Phe Pro Met Trp Val Gly
            20                  25                  30

Arg Ala Asp Asp Ala Leu Gln Gln Val Val Met Gly Tyr Leu Gly Val
        35                  40                  45

Gln Phe Arg Asp Glu Asp Gln Arg Pro Ala Leu Gln Ala Met Arg
    50                  55                  60

Asp Ile Val Ala Gly Phe Asp Leu Pro Asp Gly Pro Ala His His Asp
65                  70                  75                  80

```
Leu Thr His His Ile Asp Asn Gln Gly Tyr Glu Asn Leu Ile Val Val
                85                  90                  95

Gly Tyr Trp Lys Asp Val Ser Ser Gln His Arg Trp Ser Thr Ser Thr
            100                 105                 110

Pro Ile Ala Ser Trp Trp Glu Ser Glu Asp Arg Leu Ser Asp Gly Leu
            115                 120                 125

Gly Phe Phe Arg Glu Ile Val Ala Pro Arg Ala Glu Gln Phe Glu Thr
            130                 135                 140

Leu Tyr Ala Phe Gln Glu Asp Leu Pro Gly Val Gly Ala Val Met Asp
145                 150                 155                 160

Gly Ile Ser Gly Glu Ile Asn Glu His Gly Tyr Trp Gly Ser Met Arg
            165                 170                 175

Glu Arg Phe Pro Ile Ser Gln Thr Asp Trp Met Gln Ala Ser Gly Glu
            180                 185                 190

Leu Arg Val Ile Ala Gly Asp Pro Ala Val Gly Gly Arg Val Val Val
            195                 200                 205

Arg Gly His Asp Asn Ile Ala Leu Ile Arg Ser Gly Gln Asp Trp Ala
            210                 215                 220

Asp Ala Glu Ala Asp Glu Arg Ser Leu Tyr Leu Asp Glu Ile Leu Pro
225                 230                 235                 240

Thr Leu Gln Ser Gly Met Asp Phe Leu Arg Asp Asn Gly Pro Ala Val
            245                 250                 255

Gly Cys Tyr Ser Asn Arg Phe Val Arg Asn Ile Asp Ile Asp Gly Asn
            260                 265                 270

Phe Leu Asp Leu Ser Tyr Asn Ile Gly His Trp Ala Ser Leu Asp Gln
            275                 280                 285

Leu Glu Arg Trp Ser Glu Ser His Pro Thr His Leu Arg Ile Phe Thr
            290                 295                 300

Thr Phe Phe Arg Val Ala Ala Gly Leu Ser Lys Leu Arg Leu Tyr His
305                 310                 315                 320

Glu Val Ser Val Phe Asp Ala Ala Asp Gln Leu Tyr Glu Tyr Ile Asn
            325                 330                 335

Cys His Pro Gly Thr Gly Met Leu Arg Asp Ala Val Thr Ile Ala Glu
            340                 345                 350

His

<210> SEQ ID NO 27
<211> LENGTH: 353
<212> TYPE: PRT
<213> ORGANISM: Rhodococcus globerulus

<400> SEQUENCE: 27

Met Glu Ser Ala Ile Gly Glu His Leu Gln Cys Pro Arg Thr Leu Thr
1               5                   10                  15

Arg Arg Val Pro Asp Thr Tyr Thr Pro Pro Phe Pro Met Trp Val Gly
            20                  25                  30

Arg Ala Asp Asp Thr Leu His Gln Val Val Met Gly Tyr Leu Gly Val
            35                  40                  45

Gln Phe Arg Gly Glu Asp Gln Arg Pro Ala Ala Leu Arg Ala Met Arg
50                  55                  60

Asp Ile Val Ala Gly Phe Asp Leu Pro Asp Gly Pro Ala His His Asp
65                  70                  75                  80

Leu Thr His His Ile Asp Asn Gln Gly Tyr Glu Asn Leu Ile Val Val
                85                  90                  95
```

```
Gly Tyr Trp Lys Asp Val Ser Gln His Arg Trp Ser Thr Ser Pro
                100                 105                 110

Pro Val Ser Ser Trp Trp Glu Ser Glu Asp Arg Leu Ser Asp Gly Leu
            115                 120                 125

Gly Phe Phe Arg Glu Ile Val Ala Pro Arg Ala Glu Gln Phe Glu Thr
130                 135                 140

Leu Tyr Ala Phe Gln Asp Asp Leu Pro Gly Val Gly Ala Val Met Asp
145                 150                 155                 160

Gly Val Ser Gly Glu Ile Asn Glu His Gly Tyr Trp Gly Ser Met Arg
                165                 170                 175

Glu Arg Phe Pro Ile Ser Gln Thr Asp Trp Met Gln Ala Ser Gly Glu
            180                 185                 190

Leu Arg Val Val Ala Gly Asp Pro Ala Val Gly Gly Arg Val Val Val
        195                 200                 205

Arg Gly His Asp Asn Ile Ala Leu Ile Arg Ser Gly Gln Asp Trp Ala
    210                 215                 220

Asp Ala Glu Ala Asp Glu Arg Ser Leu Tyr Leu Asp Glu Ile Leu Pro
225                 230                 235                 240

Thr Leu Gln Ser Gly Met Asp Phe Leu Arg Asp Asn Gly Pro Ala Val
                245                 250                 255

Gly Cys Tyr Ser Asn Arg Phe Val Arg Asn Ile Asp Ile Asp Gly Asn
            260                 265                 270

Phe Leu Asp Leu Ser Tyr Asn Ile Gly His Trp Ala Ser Leu Asp Gln
275                 280                 285

Leu Glu Arg Trp Ser Glu Ser His Pro Thr His Leu Arg Ile Phe Thr
        290                 295                 300

Thr Phe Phe Arg Val Ala Glu Gly Leu Ser Lys Leu Arg Leu Tyr His
305                 310                 315                 320

Glu Val Ser Val Phe Asp Ala Ala Asp Gln Leu Tyr Glu Tyr Ile Asn
                325                 330                 335

Cys His Pro Gly Thr Gly Met Leu Arg Asp Ala Val Ile Thr Ala Glu
            340                 345                 350

His

<210> SEQ ID NO 28
<211> LENGTH: 497
<212> TYPE: PRT
<213> ORGANISM: Arabidopsis thaliana

<400> SEQUENCE: 28

Met Glu Met Ile Leu Ser Ile Ser Leu Cys Leu Thr Thr Leu Ile Thr
1               5                   10                  15

Leu Leu Leu Leu Arg Arg Phe Leu Lys Arg Thr Ala Thr Lys Val Asn
            20                  25                  30

Leu Pro Pro Ser Pro Trp Arg Leu Pro Val Ile Gly Asn Leu His Gln
        35                  40                  45

Leu Ser Leu His Pro His Arg Ser Leu Arg Ser Leu Ser Leu Arg Tyr
    50                  55                  60

Gly Pro Leu Met Leu Leu His Phe Gly Arg Val Pro Ile Leu Val Val
65                  70                  75                  80

Ser Ser Gly Glu Ala Ala Gln Glu Val Leu Lys Thr His Asp His Lys
                85                  90                  95

Phe Ala Asn Arg Pro Arg Ser Lys Ala Val His Gly Leu Met Asn Gly
            100                 105                 110
```

```
Gly Arg Asp Val Val Phe Ala Pro Tyr Gly Glu Tyr Trp Arg Gln Met
        115                 120                 125

Lys Ser Val Cys Ile Leu Asn Leu Leu Thr Asn Lys Met Val Glu Ser
130                 135                 140

Phe Glu Lys Val Arg Glu Asp Glu Val Asn Ala Met Ile Glu Lys Leu
145                 150                 155                 160

Glu Lys Ala Ser Ser Ser Ser Ser Glu Asn Leu Ser Glu Leu Phe
            165                 170                 175

Ile Thr Leu Pro Ser Asp Val Thr Ser Arg Val Ala Leu Gly Arg Lys
                180                 185                 190

His Ser Glu Asp Glu Thr Ala Arg Asp Leu Lys Lys Arg Val Arg Gln
        195                 200                 205

Ile Met Glu Leu Leu Gly Glu Phe Pro Ile Gly Glu Tyr Val Pro Ile
    210                 215                 220

Leu Ala Trp Ile Asp Gly Ile Arg Gly Phe Asn Asn Lys Ile Lys Glu
225                 230                 235                 240

Val Ser Arg Gly Phe Ser Asp Leu Met Asp Lys Val Val Gln Glu His
                245                 250                 255

Leu Glu Ala Ser Asn Asp Lys Ala Asp Phe Val Asp Ile Leu Leu Ser
            260                 265                 270

Ile Glu Lys Asp Lys Asn Ser Gly Phe Gln Val Gln Arg Asn Asp Ile
        275                 280                 285

Lys Phe Met Ile Leu Asp Met Phe Ile Gly Gly Thr Ser Thr Thr Ser
    290                 295                 300

Thr Leu Leu Glu Trp Thr Met Thr Glu Leu Ile Arg Ser Pro Lys Ser
305                 310                 315                 320

Met Lys Lys Leu Gln Asp Glu Ile Arg Ser Thr Ile Arg Pro His Gly
                325                 330                 335

Ser Tyr Ile Lys Glu Lys Glu Val Glu Asn Met Lys Tyr Leu Lys Ala
            340                 345                 350

Val Ile Lys Glu Val Leu Arg Leu His Pro Ser Leu Pro Met Ile Leu
        355                 360                 365

Pro Arg Leu Leu Ser Glu Asp Val Lys Val Lys Gly Tyr Asn Ile Ala
    370                 375                 380

Ala Gly Thr Glu Val Ile Ile Asn Ala Trp Ala Ile Gln Arg Asp Thr
385                 390                 395                 400

Ala Ile Trp Gly Pro Asp Ala Glu Glu Phe Lys Pro Glu Arg His Leu
                405                 410                 415

Asp Ser Gly Leu Asp Tyr His Gly Lys Asn Leu Asn Tyr Ile Pro Phe
            420                 425                 430

Gly Ser Gly Arg Arg Ile Cys Pro Gly Ile Asn Leu Ala Leu Gly Leu
        435                 440                 445

Ala Glu Val Thr Val Ala Asn Leu Val Gly Arg Phe Asp Trp Arg Val
    450                 455                 460

Glu Ala Gly Pro Asn Gly Asp Gln Pro Asp Leu Thr Glu Ala Ile Gly
465                 470                 475                 480

Ile Asp Val Cys Arg Lys Phe Pro Leu Ile Ala Phe Pro Ser Ser Val
                485                 490                 495

Val
```